US011873483B2

(12) United States Patent
Nicol et al.

(10) Patent No.: US 11,873,483 B2
(45) Date of Patent: Jan. 16, 2024

(54) PROTEOMIC ANALYSIS WITH NUCLEIC ACID IDENTIFIERS

(71) Applicants: THE BROAD INSTITUTE, INC., Cambridge, MA (US); ÉCOLE SUPERIEURE DE PHYSIQUE ET DE CHIMIE INDUSTRIELLES DE LA VILLE DE PARIS (ESPCI PARIS TECH), Paris (FR)

(72) Inventors: Robert Nicol, Cambridge, MA (US); Andrew David Griffiths, Paris (FR); Baptiste Saudemont, Fontenay-aux-Roses (FR); Timothy V. Kirk, Paris (FR)

(73) Assignees: The Broad Institute, Inc., Cambridge, MA (US); ÉCOLE SUPERIEURE DE PHYSIQUE ET DE CHIMIE INDUSTRIELLES DE LA VILLE DE PARIS (ESPCI PARIS TECH), Paris (FR)

( * ) Notice: Subject to any disclaimer, the term of this patent is extended or adjusted under 35 U.S.C. 154(b) by 370 days.

(21) Appl. No.: 15/557,442

(22) PCT Filed: Mar. 11, 2016

(86) PCT No.: PCT/US2016/022201
§ 371 (c)(1),
(2) Date: Sep. 11, 2017

(87) PCT Pub. No.: WO2016/145409
PCT Pub. Date: Sep. 15, 2016

(65) Prior Publication Data
US 2018/0112212 A1 Apr. 26, 2018

Related U.S. Application Data

(60) Provisional application No. 62/131,804, filed on Mar. 11, 2015.

(51) Int. Cl.
C12P 19/34 (2006.01)
C12N 15/10 (2006.01)
G01N 33/68 (2006.01)
C12Q 1/6816 (2018.01)

(52) U.S. Cl.
CPC ........ *C12N 15/1075* (2013.01); *C12Q 1/6816* (2013.01); *G01N 33/6845* (2013.01); *G01N 2458/10* (2013.01)

(58) Field of Classification Search
USPC ... 435/6.1, 6.11, 7.1, 91.1, 91.2, 91.51, 183; 436/94, 501; 536/23.1, 24.3, 24.33, 25.3
See application file for complete search history.

(56) References Cited

U.S. PATENT DOCUMENTS

| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,683,195 A | 7/1987 | Mullis et al. |
| 4,683,202 A | 7/1987 | Mullis et al. |
| 5,427,930 A | 6/1995 | Birkenmeyer et al. |
| 5,744,311 A | 4/1998 | Fraiser et al. |
| 5,866,336 A | 2/1999 | Nazarenko et al. |
| 6,025,134 A | 2/2000 | Sooknanan |
| 6,027,889 A | 2/2000 | Barany et al. |
| 6,033,880 A | 3/2000 | Haff et al. |
| 6,033,881 A | 3/2000 | Himmler et al. |
| 6,524,456 B1 | 2/2003 | Ramsey et al. |
| 6,617,145 B2 | 9/2003 | Boone et al. |
| 7,041,481 B2 | 5/2006 | Anderson et al. |
| 7,129,091 B2 | 10/2006 | Ismagilov et al. |
| 7,708,949 B2 | 5/2010 | Stone et al. |
| RE41,780 E | 9/2010 | Anderson et al. |
| 8,273,573 B2 | 9/2012 | Ismagilov et al. |
| 8,304,193 B2 | 11/2012 | Ismagilov et al. |
| 8,329,407 B2 | 12/2012 | Ismagilov et al. |
| 8,658,430 B2 | 2/2014 | Miller et al. |

(Continued)

FOREIGN PATENT DOCUMENTS

| EP | 0 320 308 A2 | 6/1989 |
| EP | 2047910 A2 | 4/2009 |

(Continued)

OTHER PUBLICATIONS

"Phenotype", "Genotype" and "Post-translational modifications" from Wikipedia. Printed on May 7, 2021.*
International Search Report and Written Opinion for PCT Application No. PCT/US2016/022201, dated Jun. 3, 2016, 10 pages.
El Debs, et al., "Functional Single-Cell Hybridoma Screening Using Droplet-Based Microfluidics", Proceedings of the National Academy of Sciences of the United States of America, Jul. 2, 2012, 11570-11575.
Mazutis, et al., "Single-Cell Analysis and Sorting Using Droplet-Based Microfluidics", Nature Protocols, vol. 8, No. 5, Apr. 4, 2013, 870-891.

(Continued)

*Primary Examiner* — Frank W Lu
(74) *Attorney, Agent, or Firm* — Brent Nix, Esq.; Johnson, Marcou, Isaacs & Nix, LLC

(57) ABSTRACT

The disclosure provides methods and compositions useful for labeling of target molecules with origin-specific nucleic acid identifiers (for example, barcodes), which can be used subsequently to identify, quantify, or otherwise characterize a feature or activity of target molecules originating from a particular discreet volume. Such target molecules can include polypeptides expressed by cells, in which nucleic acid molecules encoding the polypeptides are labeled with the same, or matched, origin-specific nucleic acid identifiers.

30 Claims, 39 Drawing Sheets

(56) References Cited

U.S. PATENT DOCUMENTS

| | | | |
|---|---|---|---|
| 8,822,148 | B2 | 9/2014 | Ismagliov |
| 8,835,358 | B2 | 9/2014 | Fodor et al. |
| 8,871,444 | B2 | 10/2014 | Ahn et al. |
| 8,889,083 | B2 | 11/2014 | Ismagilov et al. |
| 9,089,844 | B2 | 7/2015 | Hiddessen et al. |
| 9,126,160 | B2 | 9/2015 | Ness et al. |
| 9,216,392 | B2 | 12/2015 | Hindson et al. |
| 9,249,460 | B2 | 2/2016 | Pushkarev et al. |
| 9,290,808 | B2 | 3/2016 | Fodor et al. |
| 9,290,809 | B2 | 3/2016 | Fodor et al. |
| 9,315,857 | B2 | 4/2016 | Fu et al. |
| 9,347,059 | B2 | 5/2016 | Saxonov |
| 9,388,465 | B2 | 7/2016 | Hindson et al. |
| 9,500,664 | B2 | 11/2016 | Ness et al. |
| 9,567,631 | B2 | 2/2017 | Hindson et al. |
| 9,567,645 | B2 | 2/2017 | Fan et al. |
| 9,567,646 | B2 | 2/2017 | Fan et al. |
| 9,598,736 | B2 | 3/2017 | Fan et al. |
| 9,636,682 | B2 | 5/2017 | Hiddessen et al. |
| 9,637,799 | B2 | 5/2017 | Fan et al. |
| 9,644,204 | B2 | 5/2017 | Hindson et al. |
| 9,649,635 | B2 | 5/2017 | Hiddessen et al. |
| 9,689,024 | B2 | 6/2017 | Hindson et al. |
| 9,695,468 | B2 | 7/2017 | Hindson et al. |
| 9,708,654 | B2 | 7/2017 | Hunicke-Smith et al. |
| 9,708,659 | B2 | 7/2017 | Fodor et al. |
| 9,816,121 | B2 | 11/2017 | Agresti et al. |
| 9,816,137 | B2 | 11/2017 | Fodor et al. |
| 9,826,137 | B2 | 11/2017 | Yokomizo |
| 9,845,502 | B2 | 12/2017 | Fodor et al. |
| 9,856,530 | B2 | 1/2018 | Hindson et al. |
| 9,885,034 | B2 | 2/2018 | Saxonov |
| 2002/0172965 | A1 | 11/2002 | Kamb et al. |
| 2005/0172476 | A1 | 8/2005 | Stone et al. |
| 2006/0078888 | A1 | 4/2006 | Griffiths et al. |
| 2007/0195127 | A1 | 8/2007 | Ahn et al. |
| 2008/0003142 | A1 | 1/2008 | Link et al. |
| 2008/0014589 | A1 | 1/2008 | Link et al. |
| 2009/0042737 | A1 | 2/2009 | Katz et al. |
| 2010/0002241 | A1 | 1/2010 | Hirose |
| 2010/0022414 | A1 | 1/2010 | Link et al. |
| 2010/0137163 | A1 | 6/2010 | Link et al. |
| 2010/0172803 | A1 | 7/2010 | Stone et al. |
| 2011/0319298 | A1 | 12/2011 | Benner et al. |
| 2012/0122714 | A1 | 5/2012 | Samuels et al. |
| 2012/0219947 | A1 | 8/2012 | Yurkovetsky et al. |
| 2012/0220494 | A1 | 8/2012 | Samuels et al. |
| 2013/0274117 | A1 | 10/2013 | Church et al. |
| 2014/0031243 | A1 | 1/2014 | Cai et al. |
| 2014/0155295 | A1 | 6/2014 | Hindson et al. |
| 2014/0235506 | A1 | 8/2014 | Hindson et al. |
| 2014/0357500 | A1 | 12/2014 | Vigneault et al. |
| 2015/0005199 | A1 | 1/2015 | Hindson et al. |
| 2015/0011430 | A1 | 1/2015 | Saxonov |
| 2018/0030515 | A1 | 2/2018 | Regev et al. |
| 2018/0112212 | A1 | 4/2018 | Nicol et al. |

FOREIGN PATENT DOCUMENTS

| | | |
|---|---|---|
| EP | 3 268 462 A1 | 1/2018 |
| WO | 90/01069 A1 | 2/1990 |
| WO | 02099078 A2 | 12/2002 |
| WO | 2004002627 A2 | 1/2004 |
| WO | 2004016767 A2 | 2/2004 |
| WO | 2005003291 A2 | 1/2005 |
| WO | 2007089541 A2 | 8/2007 |
| WO | 2009036379 A2 | 3/2009 |
| WO | 2013116698 A2 | 8/2013 |
| WO | 2013188872 A1 | 12/2013 |
| WO | 2014026032 A2 | 2/2014 |
| WO | 2014/047556 A1 | 3/2014 |
| WO | 2014047561 A1 | 3/2014 |
| WO | 2014/143158 A1 | 9/2014 |
| WO | 2016040476 A1 | 3/2016 |
| WO | 2016/145409 A1 | 9/2016 |

OTHER PUBLICATIONS

"Supplemental European Search Report issued in EPO Application No. 16762675.3", dated Jul. 13, 18, 1-7.

Davidson, et al., "Directed Evolution of Proteins in Vitro Using Compartmentalization in Emulsions", Current Protocols in Molecular Biology, John Wiley & Sons, May 1, 2001, 1-12.

Lu, et al., "In vitro Selection of Proteins via Emulsion Compartments", Methods, vol. 60, No. 1, Mar. 1, 2013, 75-80.

Rothe, et al., "Novel Proteins in Emulsions Using in vitro Compartmentalization", Trends in Biotechnology, vol. 24, No. 12, Dec. 1, 2006, 587-592.

Rothberg, et al., "An integrated semiconductor device enabling non-optical genome sequencing", Nature, vol. 475, pp. 348-352, Jul. 21, 2011.

Shimkus, et al., "A chemically cleavable biotinylated nucleotide: usefulness in the recovery of protein-DNA complexes from avidin affinity columns.", Proc Natl Acad Sci U S A., vol. 82, No. 9, pp. 2593-2597, May 1985.

Song, et al., "A Microfluidic System for Controlling Reaction Networks in Time", Angew. Chem. Int. Ed. 2003, vol. 42, No. 7, pp. 767-772.

Soumillon, et al., "Characterization of Directed Differentiation by High-Throughput Single-Cell RNA-Seq", BioRxiv, pp. 1-13, Preprint: Mar. 5, 2014.

Spies, et al., "Genome-wide reconstruction of complex structural variants using read clouds", Nat Methods, vol. 14, No. 9, pp. 915-920, Sep. 2017.

Stoeckius, et al., "Large-scale simultaneous measurement of epitopes and transcriptomes in single cells", Nature Methods, vol. 14, No. 9, pp. 865-868, Sep. 2017.

Taylor, et al., "A scalable high-throughput method for RNA-Seq analysis of thousands of single cells", illumina I Bio-Rad, 2016.

Tewhey, et al., "Microdroplet-based PCR enrichment for large-scale targeted sequencing", Nature Biotechnology, vol. 27, No. 11, pp. 1025-1031, Nov. 1, 2009.

The Broad Institute, Inc., "Communication Pursuant to Rule 164(2)(b) and Article 94(3) EPC", Jul. 11, 2018, 12 pages.

Tice, et al., "Formation of Droplets and Mixing in Multiphase Microfluidics at Low Values of the Reynolds and the Capillary Numbers", Langmuir, vol. 19, No. 22, pp. 9127-9132, Published on Web: Aug. 12, 2003.

Wilson, "Ape1 abasic endonuclease activity is regulated by magnesium and potassium concentrations and is robust on alternative DNA structures.", J Mol Biol., vol. 345, No. 5, pp. 1003-1014, Feb. 4, 2005.

Wu, et al., "Termination of DNA synthesis by N6-alkylated, not 3'-O-alkylated, photocleavable 2'-deoxyadenosine triphosphates", Nucleic Acids Res., vol. 35, No. 19, pp. 6339-6349, Sep. 18, 2007.

Yan, et al., "Intestinal enteroendocrine lineage cells possess homeostatic and injury-inducible stem cell activity", Cell Stem Cell, vol. 21, No. 1, pp. 78-90, Jul. 6, 2017.

Yan, et al., "Non-equivalence of Wnt and R-spondin ligands during Lgr5+ intestinal stem cell self-renewal", Nature, vol. 545, No. 7653, pp. 238-242, May 11, 2017.

Zhang, et al., "Massively Parallel Single-Molecule and Single-Cell Emulsion Reverse Transcription Polymerase Chain Reaction Using Agarose Droplet Microfluidics", Anal. Chem., vol. 84, No. 8, pp. 3599-3606, Published: Mar. 27, 2012.

Zheng, et al., "Massively parallel digital transcriptional profiling of single cells", Nature Communications, vol. 8, Article No. 14049, pp. 1-12, Published: Jan. 16, 2017.

Metzker, "Sequencing technologies—the next generation", Nature Reviews, Genetics, vol. 11, pp. 31-46, Published online: Dec. 8, 2009.

"2017 Top 10 Innovations", 2017 Top 10 Innovations, The Scientist, pp. 1-11, Dec. 1, 2017.

"Acrylamide Product Information Sheet", Sigma Aldrich 1996 Product Information Sheet, A8887, pp. 1-2, 1996.

"American Cell Biology Meeting Program 2017", The 2017 ASCB EMBO Meeting, pp. 1-198, Dec. 2017.

(56) References Cited

OTHER PUBLICATIONS

"An Introduction to Linked-Read Technology for a More Comprehensive Genome and Exome Analysis", 10X Genomics Technical Note, pp. 1-5, 2016.
Bio-Rad and Illumina to Co-Develop Comprehensive Solution for Single-Cell Genomics, "Scalable, High-Throughput Platform to Offer Unprecedented Insight into Gene Expression of Individual Cells," Bio-Rad Newsroom, pp. 1-2, Jan. 11, 2016.
"Bio-Rad ddSEQ Single-Cell Isolator Instruction Manual", Bio-Rad, Catalog #12004336, pp. 1-24, 2017.
"Bio-Rad Laboratories, Inc. Form 10-K for the year ended Dec. 31, 2016", pp. 1-92.
"Bio-Rad Life Science Research Product Catalog", Bio-Rad Life Science Research 2017 Product Catalog, pp. 1-500, 2017.
"Boston Medical Center/ Boston University School of Medicine Department of Medicine Newsletter", pp. 1-20, 2017.
"Cancer Moonshot", National Cancer Institute, pp. 1-4, Jan. 8, 2019.
"ChromiumTM Genome Reagent Kits v2 User Guide," Multiplex Kit, 96 rxns, PN-120262, 10X Genomics, pp. 1-71, 2016.
"ChromiumTM Single Cell 3' Reagent Kits Quick Reference Cards", ChromiumTM Single Cell 3' Chip Kit PN-120232, 10X Genomics, pp. 1-10, 2016.
"ChromiumTM Chromium Single Cell 3' Reagent Kits Safety Data Sheets", ChromiumTM Single Cell 3' Gel Bead Kit PN-120231, 10X Genomics, pp. 1-10, Jul. 11, 2016.
"ChromiumTM Chromium Single Cell 3' Reagent Kits v2 Safety Data Sheets," Chromium Single Cell 3' Gel Bead Kit v2, 16 runs, PN-120235, 10X Genomics, pp. 1-10, Oct. 7, 2016.
"Chromium Single Cell 3' Reagent Kits v3 with Feature Barcoding technology for CRISPR Screening", Chromium Single Cell 3' GEM, Library & Gel Bead Kit v3, 4 rxns PN-1000092, 10X Genomics, pp. 1-70, CG000184 | Rev A, 2018.
"ChromiumTM Single Cell 3' Reagent Kits v2 Quick Reference Cards," ChromiumTM Single Cell 3' Library & Gel Bead Kit, 4 rxns PN-120267, 10X Genomics, CG000075 | Rev C, pp. 1-10, 2017.
"ChromiumTM Single Cell 3' Reagent Kits Safety Data Sheets," ChromiumTM Single Cell 3' Library Kit, 10X Genomics, PN-120230, pp. 1-139, May 25, 2016.
"ChromiumTM Single Cell 3' Reagent Kits v2 Safety Data Sheets," ChromiumTM Single Cell 3' Library Kit v2 16 rxns, PN-120234, 10X Genomics, pp. 1-121, Oct. 7, 2016.
"Chromium Single Cell 3' Reagent Kits v2 User Guide," Chromium Single Cell 3' Library & Gel Bead Kit v2, 16 rxns PN-120237, 10X Genomics, pp. 1-74, 2018.
"ChromiumTM Single Cell V(D)J Reagent Kits User Guide," ChromiumTM Single Cell 5' Library & Gel Bead Kit, 16 rxns PN-1000006, 10X Genomics, pp. 1-73, 2017.
"Chromium Single Cell 3' Reagent Kits v2 User Guide", Chromium Single Cell A Chip Kit, 16 rxns PN-1000009, 10X Genomics, pp. 1-74, CG00052 | Rev E, 2018.
"Chromium Single Cell 3' Reagent Kits v2 Safety Data Sheets," Chromium Single Cell A Chip Kit, 48 runs, 10X Genomics, PN-120236, Oct. 6, 2016.
"Chromium Single Cell ATAC Reagent Kits," Chromium Single Cell ATAC Library & Gel Bead Kit, 16 rxns PN-1000110, 10X Genomics, CG000168 | Rev A, pp. 1-47, 2018.
"Chromium Single Cell DNA Reagent Kits", Chromium Single Cell DNA Library & Gel Bead Kit, 16 rxns PN-1000040, 10X Genomics, CG000153 | Rev B, pp. 1-65, 2018.
"ChromiumTM Controller Training Kit User Guide", 10X Genomics, CG00021 | Rev B, pp. 1-27, (Product ID 120244), 2016.
"ChromiumTM Training Kits Safety Data Sheets", ChromiumTM Training Reagents and Gel Bead Kit, 10X Genomics, PN-120238, Rev A, pp. 1-33, May 24, 2016.
"DdSEQ™ Cartridge Holder", Bio-Rad ddSEQ™ Cartridge Holder #12004739, 2016.
"DdSEQ™ Single-Cell Isolator—Accessories", ddSEQ™ Single-Cell Isolator—Accessories—Bio-Rad, pp. 1-2, 2016.
"DdSEQ™ Single-Cell Isolator—Ordering", ddSEQ™ Single-Cell Isolator Bio-Rad, 2016.
"DdSEQ™ Single-Cell Isolator by Bio-Rad", Bio-Rad, pp. 1-8, Select Science, 2019.
"DdSEQ™ Single-Cell Isolator by Bio-Rad", ddSEQ™ Single-Cell Isolator, Bio-Rad, pp. 1-2, 2016.
"DdSEQ™ Test Cartridges", Bio-Rad ddSEQ™ Test Cartridges #12003862, 2016.
"Deoxyribonuclease I from bovine pancreas", Sigma-Aldrich Deoxyribonuclease I from bovine pancreas, CAS No. 9003-98-9, 2018.
"DNase I (RNase-free)", New England Biolabs, Inc. (NEB), pp. 1-6, 2018.
"DTT 1,4-Dithiothreitol", Sigma-Aldrich, CAS No. 3483-12-3, pp. 1-4, 2015.
Office Action issued by the European Patent Office in Application No. 15767655.2 dated Apr. 17, 2018, 4 pages.
Office Action issued by the European Patent Office in Application No. 15767655.2 dated Jul. 11, 2018, 12 pages.
Banga, J.P., "SDS-Polyacrylamide Gel Electrophoresis (SDS-PAGE)", Encyclopedia of Immunology ISBN:0-12-226765-6, pp. 2143-2144, 1998.
"Generation of Human Tumor Atlases-Cancer Moonshot Recommendation", National Cancer Institute, pp. 1-4, Jan. 8, 2019.
"Genome Analysis Core", pp. 1-2, Georgia Institute of Technology, 2019.
"Georgia Tech—Shared User Management System", pp. 1-12, Georgia Institute of Technology, 2015.
"Hydrophobic Interaction Chromatography", Amersham Pharmacia Biotech 2000, Edition AB, pp. 1-104, ISBN 91-970490-4-2, 2000.
"Illumina and Bio-Rad Launch Solution for Single-Cell Genomic Sequencing to Enable Robust Study of Complex Diseases", Bio-Rad, pp. 1-2, Jan. 9, 2017.
"Illumina and Bio-Rad Launch Solution for Single-Cell Genomic Sequencing to Enable Robust Study of Complex Diseases", 69th AACC Annual Scientific Meeting Press Program, Article ID: 678428, pp. 1-6, Jul. 25, 2017.
"Illumina Bio-Rad SureCell WTA 3' Library Prep Reference Guide", Illumina, Document # 1000000021452 v01, pp. 1-53, Jun. 2017.
"Illumina SureCell WTA 3' Checklist", Illumina, Document # 1000000021454 v00, pp. 1-6, Feb. 2017.
"Illumina® | Bio-Rad® Single Cell Sequencing", illumina I Bio-Rad, pp. 1-37, 2015.
"Illumina® Bio-Rad® SureCellTM WTA 3' Library Prep Kit for the ddSEQTM System", illumina I Bio-Rad, pp. 1-4, 2015.
"Infoporte—Cores", Infoporte | Version: 7.1.1 | © 2019 The University of North Carolina at Chapel Hill.
"The Instrument—Chromium Controller Compatible Solutions", 10X Genomics, pp. 1-7, 2019.
"International Preliminary Report on Patentability for PCT Application No. PCT/US2016/022201", dated Sep. 12, 2017, 1-5.
"European Office Action issued in European Application No. 16762675.3", dated Mar. 18, 2019, 5 pages.
Anna, et al., "Formation of Dispersions Using Flow Focusing in Microchannels", Applied Physics Letters, vol. 82, No. 3, Jan. 20, 2003, 364-366.
Baret, et al., "Fluorescence-activated Droplet Sorting (Fads): Efficient Microfluidic Cell Sorting Based On Enzymatic Activity", Lab on a Chip, vol. 9, No. 13, Jul. 7, 2009, 1850-1858.
Chabert, et al., "Droplet Fusion By Alternating Current (AC) Field Electrocoalescence In Microchannels", Electrophoresis, vol. 26, No. 19, Oct. 2005, 3706-3715.
Frenz, et al., "Reliable Microfluidic On-chip Incubation of Droplets in Delay-lines", Lab on a Chip, vol. 9, No. 10, May 21, 2009, 1344-1348.
Guo, et al., "Droplet Microfluidics for High-throughput Biological Assays", Lab on a Chip, vol. 12, No. 12, Jun. 21, 2012, 2146-2155.
Weis, et al., "Detection of Rare Mrnas via Quantitative RT-PCR", Trends in Genetics, vol. 8, No. 8, Aug. 1992, 263-264.
Kim, et al., "Fabrication of Monodisperse Gel Shells and Functional Microgels in Microfluidic Devices", Angewandte Chemie International Edition, vol. 46, No. 11, 2007, 1819-1822.

(56) References Cited

OTHER PUBLICATIONS

Koster, et al., "Drop-based Microfluidic Devices for Encapsulation of Single Cells", Lab on a Chip, vol. 8, No. 7, Jul. 2008, 1110-1115.
Kozlov, et al., "Efficient Strategies for the Conjugation of Oligonucleotides to Antibodies Enabling Highly Sensitive Protein Detection", Biopolymers, vol. 73, No. 5, Apr. 5, 2004, 621-630.
Link, et al., "Geometrically Mediated Breakup of Drops in Microfluidic Devices", Physical Review Letters, vol. 92, No. 5, Feb. 6, 2004, 5 pages.
Parker, et al., "Mrna: Detection by In Situ and Northern Hybridization", Methods in Molecular Biology, vol. 106, 1999, 247-283.
Shiroguchi, et al., "Digital RNA Sequencing Minimizes Sequence Dependent Bias and Amplification Noise with Optimized Single-Molecule Barcodes", Proceedings of the National Academy of Sciences, vol. 109, No. 4, Jan. 24, 2012, 1347-1352.
Shukla, et al., "Phage Display Selection for Cell-specific Ligands: Development of a Screening Procedure Suitable for Small Tumor Specimens", Journal of Drug Targeting, vol. 13, No. 1, Jan. 2005, 7-18.
Teh, et al., "Droplet Microfluidics", Lab on a Chip, vol. 8, No. 2, Feb. 2008, 198-220.
Theberge, et al., "Microdroplets in Microfluidics: An Evolving Platform for Discoveries in Chemistry and Biology", Angewandte Chemie International Edition in English, vol. 49, No. 34, Aug. 9, 2010, 5846-5868.
"Markman Order In re Certain Microfluidic Systems and Components Thereof and Products Containing Same", Docket Alarm, pp. 1-6, Oct. 31, 2018.
"Molecular and Genomics Core Facility Equipment", Molecular and Genomics Core Facility, pp. 1-7, 2018.
"N,N'-Methylenebis(acrylamide)", 146072 Sigma-Aldrich, CAS No. 110-26-9, 2018.
"Neuroscience 2017 Program", Society for Neuroscience, pp. 1-2, 2017.
"Notice of Intent to Certify Sole Source", Sole Source Certification No. SS5098 for Bio-Rad ddSeq Single Cell Isolation System and associated accessories, pp. 1-5, Jun. 5, 2017.
"Nucleic Acid Sample Preparation for Downstream Analyses", GE Healthcare Life Sciences Manual, pp. 1-168, 2009.
"Omniscript Reverse Transcription Handbook", Qiagen, pp. 1-32, Oct. 2010.
"Phosphate-buffered saline (PBS)", pdb.rec8247-, Cold Spring Harbor Protocols (2006).
"Powerful New Tool for Genome Analysis", Georgia Tech Bioinformatics, pp. 1-3, Nov. 14, 2017.
"Q Sepharose High Performance SP Sepharose High Performance", GE Healthcare, Data File 18-1172-88 AB, pp. 1-8, Apr. 2006.
"Research Highlights: Human Cell Atlas", Human Cell Atlas | Broad Institute, pp. 1-4, Jan. 8, 2019.
"Restriction Endonucleases Technical Guide", BioLabs Inc., pp. 1-24, Aug. 2015.
"Reverse Transcription Reaction Setup—Seven Important Considerations", ThermoFisher Scientific, pp. 1-15, 2018.
"Sequencing Power for Every Scale Systems for every application. For every lab.", Illumina, pp. 1-70, 2016.
"Single-Cell RNA Data Analysis Workflow RNA analysis from single cells using the Illumina Bio-Rad Single-Cell Sequencing Solution with the BaseSpace® SureCellTM RNA Single-Cell App.", illumina | Bio-Rad, pp. 1-4, 2017.
"Single-cell RNAseq (Biorad/Illumina ddSEQ)", UNC School of Medicine, pp. 1-3, 2018.
"SITC 2017 Scientific Highlights—Nov. 11", The Sentinel—The Official Blog of the Society for Immunotherapy of Cancer (SITC)., pp. 1-4, Nov. 12, 2017.
"SureCell WTA 3' Library Prep Kit Support, Questions & Answers", Illumina, pp. 1-4, 2019.
"SureCell WTA 3' Library Prep Kit for the ddSEQ System", Ilumina, pp. 1-6, 2019.
"The Illumina Bio-Rad Single Cell Sequencing Solution", illumina | Bio-Rad, pp. 1-3, 2018.

"The Illumina Bio-Rad Single-Cell Sequencing Solution Robust and scalable single-cell sequencing", illumina | Bio-Rad, pp. 1-4, 2016.
"Top 10 Innovations 2015", The Scientist, pp. 1-12, Dec. 1, 2015.
"Transcriptor Reverse Transcriptase", Roche, Ver. 13, pp. 1-13, Jun. 2017.
"Types of Restriction Endonucleases", pp. 1-2, 2018.
U.S. Office Action issued in copending U.S. Appl. No. 15/453,405, filed Aug. 28, 2018, dated Aug. 28, 2018, 16 pages.
"University of Mississippi Medical Center, Molecular and Genomics Core Facility, Service Home", pp. 1-2, 2018.
"Genomics Resources Core Facility", Weill Cornell Medicine, pp. 1-5, 2018.
Abate, et al., "Beating Poisson encapsulation statistics using close-packed ordering", Lab Chip, vol. 9, pp. 2628-2631, Accepted: Jul. 24, 2009.
Adamson, et al., "A multiplexed single-cell CRISPR screening platform enables systematic dissection of the unfolded protein response", Cell., vol. 167, Issue 7, pp. 1867-18822, Dec. 15, 2016.
International Search Report and Written Opinion issued in International Application No. PCT/US2015/049178, dated Feb. 22, 2016, 18 pages.
Andersen, et al., "A Quantitative Study of the Human Cerebellum with Unbiased Stereological Techniques", The Journal of comparative neurology, vol. 326, Issue 4, pp. 549-560, Dec. 22, 1992.
Ascoli, et al., "Petilla Terminology: Nomenclature of Features of GABAergic Interneurons of the Cerebral Cortex", Nature reviews Neuroscience, vol. 9, pp. 557-568, Jul. 2008.
International Preliminary Report on Patentability issues in International Application No. PCT/US2015/049178, dated Mar. 23, 2017, 12 pages.
Barany, Francis, "Genetic Disease Detection and DNA Amplification Using Cloned Thermostable Ligase", PNAS, vol. 88, Issue 1, pp. 189-193, Jan. 1991.
Barany, Francis, "The Ligase Chain Reaction in a PCR World", PCR Methods and Applications, vol. 1, pp. 5-16, 1991.
Bar-Joseph, et al., "Genome-Wide Transcriptional Analysis of the Human Cell Cycle Identifies Genes Differentially Regulated in Normal and Cancer Cells", PNAS, vol. 105, Issue 3, pp. 955-960, Jan. 22, 2008.
Barres, et al., "Immunological, Morphological, and Electrophysiological Variation Among Retinal Ganglion Cells Purified by Panning", Neuron, vol. 1, Issue 9, pp. 791-803, Nov. 1988.
Beer, et al., "On-Chip Single-Copy Real-Time Reverse-Transcription PCR in Isolated Picoliter Droplets", Analytical Chemistry, vol. 80, Issue 6, pp. 1854-1858, Mar. 15, 2008.
Bentley, et al., "Accurate whole human genome sequencing using reversible terminator chemistry.", Nature, 456 (7218), pp. 53-59, Nov. 6, 2008.
Berman, et al., "Mapping the Stereotyped Behaviour of Free Moving Fruit Flies", Journal of the Royal Society Interface, vol. 11, Issue 99, 20140672, pp. 1-12, Aug. 20, 2014.
Binladen, et al., "The Use of Coded PCR Primers Enables High-Throughput Sequencing of Multiple Homolog Amplification Products by 454 Parallel Sequencing", PLOS One; vol. 2, Issue 2: e197, pp. 1-9, Feb. 14, 2007.
Bitinaite, et al., "USER™ friendly DNA engineering and cloning method by uracil excision", Nucleic Acids Res., vol. 35, No. 6, pp. 1992-2002, Publised online Mar. 6, 2007.
Black, Chris, "The ChromiumTM System: Linked Read and Single Cell RNA-Seq Applications Powered by GemCode Technology", 10X Genomics, pp. 1-57, Jul. 17, 2017.
Bochet, Christian G., "Photolabile protecting groups and linkers", J. Chem. Soc., Perkin Trans. 1, 2002,0, pp. 125-142, First published as an Advance Article on the Web: Dec. 13, 2001.
Brennecke, et al., "Accounting for Technical Noise in Single-Cell RNA-seq Experiments", Nature methods, vol. 10, Issue 11, 1093-1095, Sep. 22, 2013.
Bringer, et al., "Microfluidic Systems for Chemical Kinetics that Rely on Chaotic Mixing in Droplets", Philosophical Transactions of the Royal Society a Mathematical Physical and Engineering Sciences, vol. 362, Issue 1818, pp. 1087-1104, Jun. 2004.

(56) References Cited

OTHER PUBLICATIONS

Britten, et al., "Repeated Sequences in DNA. Hundreds of Thousands of Copies of DNA Sequences have been Incorporated into the Genomes of Higher Organisms", Science, vol. 161, Issue 3841, pp. 529-540, Aug. 9, 1968.
Brouzes, et al., "Droplet Microfluidic Technology for Single-Cell High-Throughput Screening", Proceedings of the National Academy of Sciences, vol. 106, No. 34, pp. 14195-14200, Aug. 25, 2009.
Brown, et al., "Chemical Synthesis and Cloning of a Tyrosine tRNA Gene", Methods in Enzymology, vol. 68, pp. 109-151, 1979.
Buettner, et al., "Computational Analysis of Cell-to-Cell Heterogeneity in Single-Cell RNA-Sequencing Data Reveals Hidden Subpopulations of Cells", Nature Biotechnology, vol. 33, Issue 2, pp. 155-160, Feb. 2015.
Chung, et al., "Statistical Significance of Variables Driving Systematic Variation in High-Dimensional Data", Bioinformatics, vol. 31, No. 4, pp. 545-554, Advance Access publication: Oct. 21, 2014.
Collins, "Biomedical Research Highlighted in Science's 2018 Breakthroughs", NIH Director's Blog, pp. 1-9, Jan. 8, 2019.
Corbo, et al., "A Typology of Photoreceptor Gene Expression Patterns in the Mouse", PNAS, vol. 104, Issue 29, p. 12069-12074, Jul. 17, 2007.
Cuatrecasas, Pedro, "Protein Purification by Affinity Chromatography", J Biol Chem, vol. 245, Issue 12, pp. 3059-3065, Jun. 25, 1970.
Damha, et al., "An improved procedure for derivatization of controlled-pore glass beads for solid-phase oligonucleotide synthesis", Nucleic Acids Res., vol. 18, No. 13, pp. 3813-3821, Accepted: May 17, 1990.
Descamps, et al., "Gelatinase B/matrix Metalloproteinase-9 Pprovokes Cataract by Cleaving Lens BetaB 1 Crystallin", The FASEB Journal, vol. 19, Issue 1, pp. 29-35, Jan. 2005.
Ding, et al., "Progress Towards a Systematic Comparison of Single Cell RNA-Seq Methods", Broad Institute, Feb. 12, 2019.
Dixit, et al., "Perturb-Seq: Dissecting Molecular Circuits with Scalable Single-Cell RNA Profiling of Pooled Genetic Screens", Cell, vol. 167, Issue 7, pp. 1853-1866, Dec. 15, 2016.
Dobin, et al., "STAR: Ultrafast Universal RNA-seq Aligner", Bioinformatics, vol. 29, Issue 1, pp. 15-21, Advance Access publication: Oct. 25, 2012.
Dressman, et al., "Transforming single DNA molecules into fluorescent magnetic particles for detection and enumeration of genetic variations", PNAS, vol. 100, No. 15, pp. 8817-8822, Jul. 22, 2003.
Droege, et al., "The Genome Sequencer FLX System—longer reads, more applications, straight forward bioinformatics and more complete data sets.", J Biotechnol., vol. 136, Issues 1-2, pp. 3-10, Accepted: Mar. 31, 2008.
Edd, et al., "Controlled Encapsulation of Single Cells into Monodisperse Picoliter Drops", Lab Chip, vol. 8, Issue 8, pp. 1262-1264, Aug. 2008.
Ester, et al., "A Density-Based Algorithm for Discovering Clusters in Large Spatial Databases with Noise", pp. 226-231, KDD-96, 1996.
Farmer, et al., "Defining epithelial cell dynamics and lineage relationships in the developing lacrimal gland", Development, The Company of Biologists, vol. 144, Issue 13, pp. 2517-2528, Accepted: May 31, 2017.
Feigenspan, et al., "Expression of Neuronal Connexin36 in All Amacrine Cells of the Mammalian Retina", The Journal of Neuroscience, vol. 21, Issue 1, pp. 230-239, Jan. 1, 2001.
Gao, et al., "Secondary structure effects on DNA hybridization kinetics: a solution versus surface comparison", Nucleic Acids Research, 2006, vol. 34, No. 11, pp. 3370-3377, Accepted: May 27, 2006.
Glatthar, et al., "A New Photocleavable Linker in Solid-Phase Chemistry for Ether Cleavage", Org. Lett. 2000, vol. 2, No. 15, pp. 2315-2317.
Greenfieldboyce, "Biological cartographers seek to map the trillions of cells in the human body", NPR, pp. 1-5, Jan. 5, 2019.
Greer, et al., "Linked read sequencing resolves complex genomic rearrangements in gastric cancer metastases", Genome Medicine, vol. 9, No. 57, pates 1-17, 2017.
Gueroult, et al., "How Cations Can Assist DNase I in DNA Binding and Hydrolysis", PLOS Comput Biol., vol. 6, Issue 11:e1001000, pp. 1-11, Nov. 18, 2010.
Haber, et al., "A single-cell survey of the small intestinal epithelium", Nature, vol. 551, No. 7680, pp. 333-339, Nov. 16, 2017.
Hamady, et al., "Error-correcting barcoded primers for pyrosequencing hundreds of samples in multiplex", Nature Methods, vol. 5, No. 3, pp. 235-237, Mar. 2008.
Hamady, et al., "Microbial community profiling for human microbiome projects: Tools, techniques, and challenges", Genome Res., vol. 19, No. 7, pp. 1141-1152, ISSN 1088-9051/09, Jul. 2009.
He, et al., "High-resolution crystal structures reveal plasticity in the metal binding site of apurinic/apyrimidinic endonuclease I.", Biochemistry, vol. 53, No. 41, pp. 6520-6529, Published: Sep. 24, 2014.
Hoffmann, et al., "DNA bar coding and pyrosequencing to identify rare HIV drug resistance mutations", Nucleic Acids Res., vol. 35, No. 13, e91, pp. 1-8, Published online: Jun. 18, 2007.
Holmberg, et al., "The biotin-streptavidin interaction can be reversibly broken using water at elevated temperatures.", Electrophoresis, vol. 26, No. 3, pp. 501-510, Feb. 2005.
Islam, et al., "Quantitative single-cell RNA-seq with unique molecular identifiers", Nature Methods, , vol. 11, No. 2, pp. 163-166, Feb. 2014.
Kaiser, et al., "Huge trove of British biodata is unlocking secrets of depression, sexual orientation, and more", Science | AAAS, pp. 1-12, Jan. 3, 2019.
Kovall, et al., "Structural, functional, and evolutionary relationships between exonuclease and the type II restriction endonucleases", Proc Natl Acad Sci U S A., vol. 95, No. 14, pp. 7893-7897, Jul. 1998.
Kumaresan, et al., "High-Throughput Single Copy DNA Amplification and Cell Analysis in Engineered Nanoliter Droplets", Anal. Chem., vol. 80, No. 10, pp. 3522-3529, May 15, 2008.
Kutnjak, et al., "Calorimetric study of octylcyanobiphenyl liquid crystal confined to a controlled-pore glass.", Physical Review E, The American Physical Society, p. 021705-1-021705-12, Published: Aug. 22, 2003.
Litosh, et al., "Improved nucleotide selectivity and termination of 3'-OH unblocked reversible terminators by molecular tuning of 2-nitrobenzyl alkylated HOMedU triphosphates.", Nucleic Acids Res., vol. 39, No. 6, pp. 1-13, Published online: Jan. 11, 2011.
Macosko, et al., "Highly Parallel Genome-Wide Expression Profiling of Individual Cells Using Nanoliter Droplets", Cell, vol. 161, No. 5, pp. 1202-1214, May 21, 2015.
Malone, et al., "Bringing Renal Biopsy Interpretation Into the Molecular Age With Single-Cell RNA Sequencing", Seminars in Nephrology, vol. 38, Issue 1, pp. 1-17, Author Manuscript; available in PMC: Jan. 1, 2019.
Margulies, et al., "Genome Sequencing in Open Microfabricated High Density Picoliter Reactors", Nature, vol. 437, No. 7057, pp. 376-380, Sep. 15, 2005.
McKenna, et al., "The Macaque Gut Microbiome in Health, Lentiviral Infection, and Chronic Enterocolitis", PLoS Pathog., vol. 4, Issue 2, e20, pp. 0001-0012, Feb. 8, 2008.
Metzker, "Emerging technologies in DNA sequencing.", Genome Res., vol. 15, No. 12, pp. 1767-1776, Dec. 2005.
Miller, et al., "Basic Concepts of Microarrays and Potential Applications in Clinical Microbiology", Clinical Microbiology Reviews, vol. 22, No. 4, pp. 611-633, Oct. 2009.
Mol, et al., "DNA-bound structures and mutants reveal abasic DNA binding by APE1 and DNA repair coordination.", Nature, vol. 403, No. 6768, pp. 451-456, Jan. 27, 2000.
Narasimhan, et al., "Health and population effects of rare gene knockouts in adult humans with related parents", Science, vol. 352, No. 6284, pp. 474-477, Apr. 22, 2016.
Nguyen, "Optical detection for droplet size control in microfluidic droplet-based analysis systems", Nguyen et al., Optical detection for droplet size control in microfluidic droplet-based analysis systems, 117 Sensors and Actuators B 117, pp. 431-436, Available online: Jan. 18, 2006.

(56) References Cited

OTHER PUBLICATIONS

Novak, et al., "Single cell multiplex gene detection and sequencing with microfluidically generated agarose emulsions", Angew. Chem. Int. Ed., pp. 1-11, 2010.

Novak, et al., "Single Cell Multiplex Gene Detection and Sequencing with Microfluidically Generated Agarose Emulsions", Agnew. Chem. Int. Ed., pp. 390-395, Jan. 10, 2011.

Pal, et al., "Construction of developmental lineage relationships in the mouse mammary gland by single-cell RNA profiling", Nature Communications, vol. 8, Article No. 1627, pp. 1-14, Nov. 20, 2017.

Parameswaran, et al., "A pyrosequencing-tailored nucleotide barcode design unveils opportunities for large-scale sample multiplexing", Nucleic Acids Res., vol. 35, No. 19, e130, pp. 1-9, Published online: Oct. 11, 2007.

Pennisi, "Development Cell by Cell", Science, vol. 362, Issue 6421, pp. 1344-1345, Dec. 21, 2018.

Perona, "Type II restriction endonucleases.", Methods, vol. 28, No. 3, pp. 353-364, Accepted: Jul. 30, 2002.

Peterson, et al., "The effect of surface probe density on DNA hybridization", Nucleic Acids Res., vol. 29, No. 24, pp. 5163-5168, Dec. 15, 2001.

Qi, et al., "Digital analysis of the expression levels of multiple colorectal cancer-related genes by multiplexed digital-PCR coupled with hydrogel bead-array.", Analyst, vol. 136, No. 11, pp. 2252-2259, Accepted: Mar. 11, 2011.

Final Office Action for U.S. Appl. No. 15/453,405, issued by the U.S. Patent Office dated Mar. 27, 2019, 17 pages.

Office Action from corresponding Chinese application No. 201680027423.X dated Dec. 22, 2021, all enclosed pages cited.

Office Action from corresponding Chinese application No. 201680027423.X dated Mar. 4, 2022, all enclosed pages cited.

\* cited by examiner

Each bead carries a clonal population of a randomly constructed, multi-part index sequence (D/C/B/A) plus sequences that enable gene specific capture/amplification and Illumina library construction Each bead carries a clonal population of a randomly constructed, multi-part index sequence (D/C/B/A) plus sequences that enable gene specific capture/amplification and illumina library construction and a second population of antibody or protein capture sequences

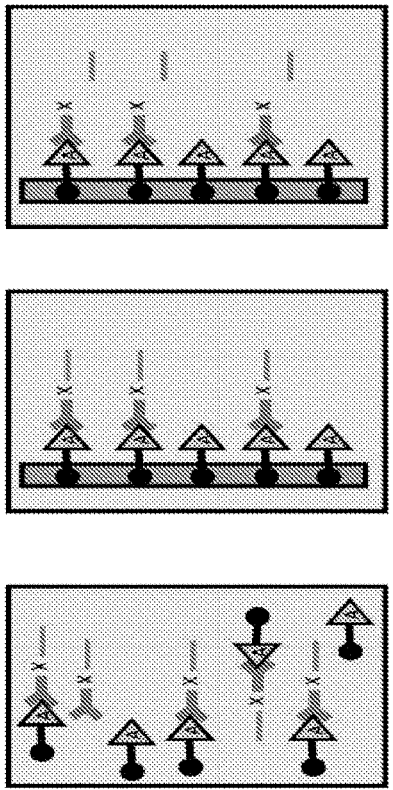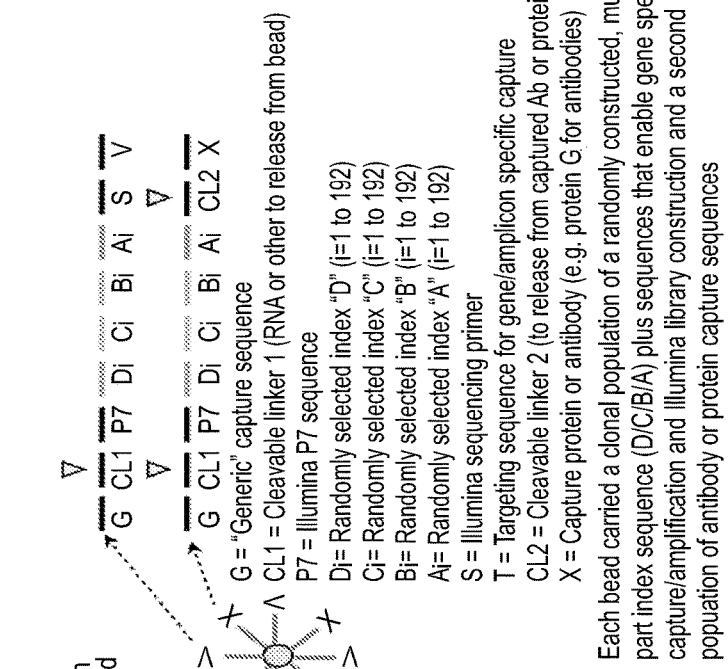
Fig. 5

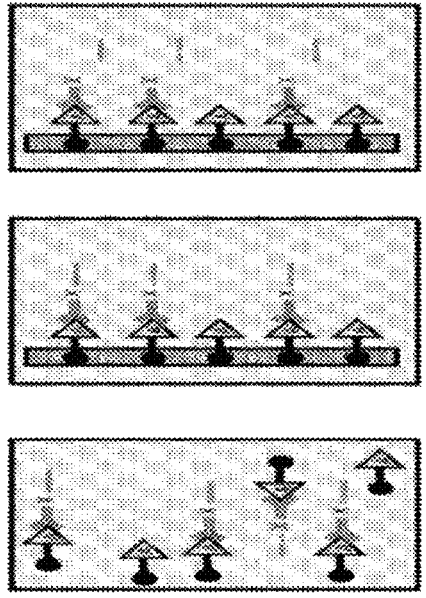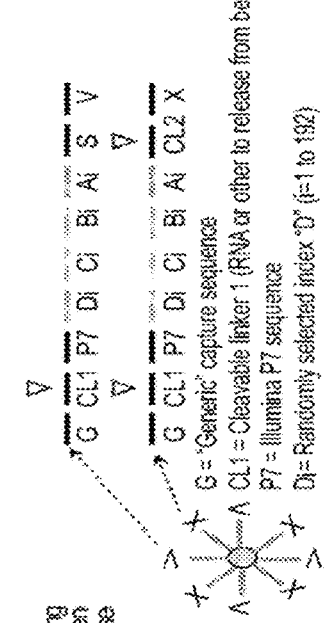
Fig. 7

Tagged antigen stucture

GP120 — B — Strep — B — SBS3-Tag-ASP

SBS3-Tag-ASP (top)
SBS3-Tag-ASP (bottom)

Fig. 8

Protein Capture and DNA Polymerisation

Labelled Antibody Structure
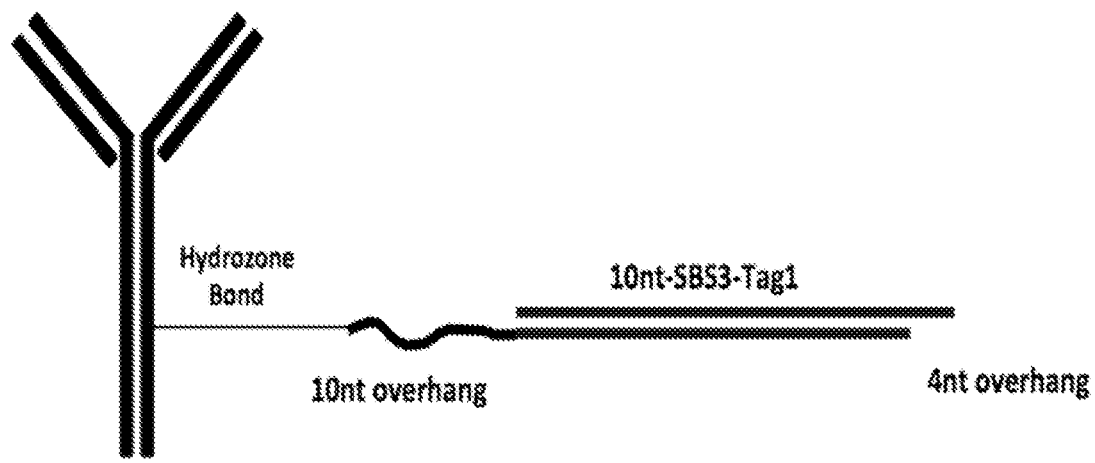
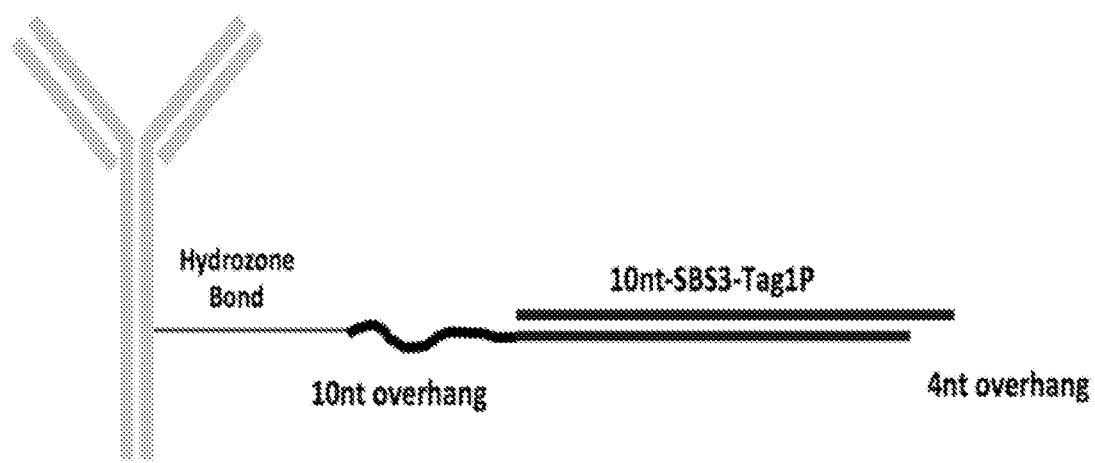
Fig. 25

RT integrity and pairing yield

Expected Heavy and Light chain pairs (with respect to used cell lines)

| | Heavy chains CDR3 amino-acid sequence | Light chains CDR3 amino-acid sequence |
|---|---|---|
| Cell line 1 | CARRETYDEKGFAYW | CQQHYSTPPTF |
| Cell line 2 | CVRMDDYDAMDYW | CHQWNSYPHTF |
| Cell line 3 | CARDTMLTPFDYW | CMQLLEYPLTF |

Sequencing data analysis results on barcode clusters with >40 reads for heavy and light chain (each)

| Heavy chain | Light chain | number of barcoded pairs | % of barcoded pairs with this Heavy chain CDR3 |
|---|---|---|---|
| CARRETYDEKGFAYW | CQQHYSTPPTF | 3431 | 67,25% |
| CARRETYDEKGFAYW | CHQWNSYPHTF | 29 | 0,57% |
| CARRETYDEKGFAYW | CMQLLEYPLTF | 10 | 0,20% |
| CVRMDDYDAMDYW | CQQHYSTPPTF | 81 | 1,59% |
| CVRMDDYDAMDYW | CHQWNSYPHTF | 1217 | 23,85% |
| CVRMDDYDAMDYW | CMQLLEYPLTF | 8 | 0,16% |
| CARDTMLTPFDYW | CQQHYSTPPTF | 42 | 0,82% |
| CARDTMLTPFDYW | CHQWNSYPHTF | 13 | 0,25% |
| CARDTMLTPFDYW | CMQLLEYPLTF | 271 | 5,31% |
| | Correctly paired | 4919 | 96,41% |

Fig. 35

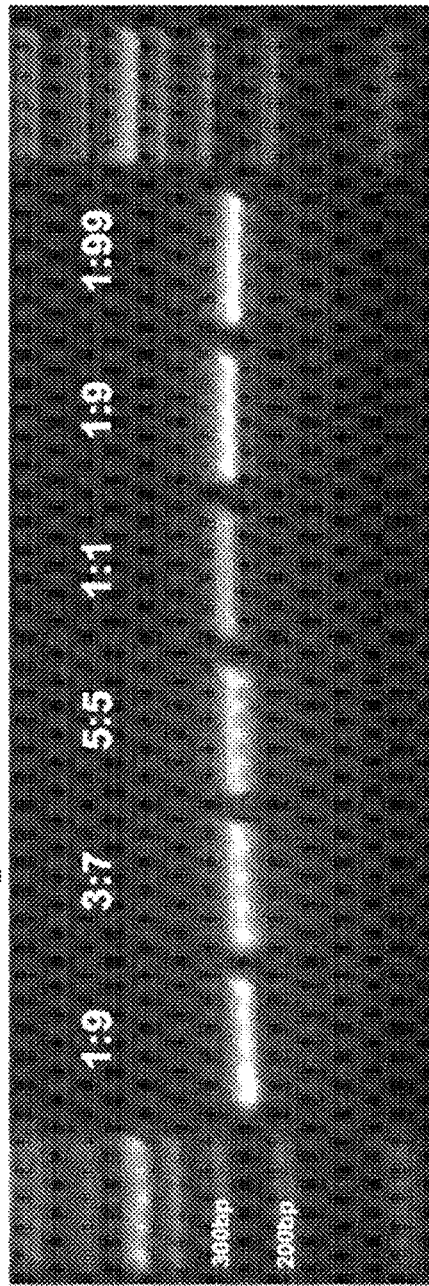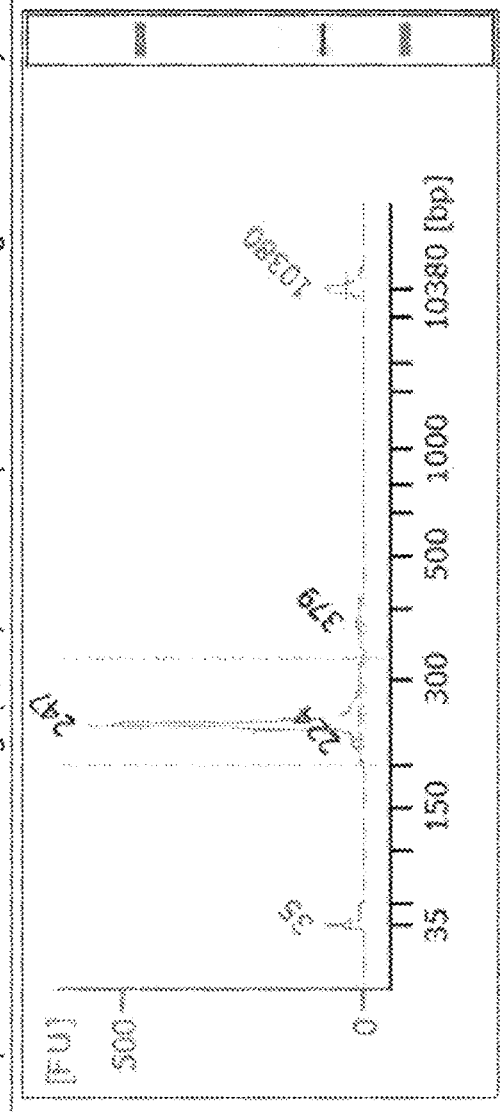
Fig. 38

PROTEOMIC ANALYSIS WITH NUCLEIC ACID IDENTIFIERS

CROSS-REFERENCE TO RELATED APPLICATIONS

The present application is a 35 U.S.C. § 371 national stage application of International Patent Application No. PCT/US2016/022201 filed on Mar. 11, 2016, which claims the benefit of U.S. Provisional Patent Application No. 62/131,804 filed Mar. 11, 2015. The entire contents of the above-referenced applications are hereby incorporated in their entirety herein.

FIELD OF THE DISCLOSURE

The present disclosure relates to methods and compositions for the specific labeling of molecules with indexable nucleic acid identifiers that can couple the genotype of a cell or acellular system to at least one phenotype of the cell or acellular system. The methods and compositions allow for multiplex analysis of diverse coupled genotypes and phenotypes while maintaining information about sample or subsample origin.

BACKGROUND

Modern genetic engineering methods allow for rapid and inexpensive production of nucleic acid constructs and variants. High complexity pools of permutations of genetic designs can be constructed in high-throughput fashion, thus providing enormous potential for exploration of a given design space. However, analysis of such large and complex pools of genetic variants requires that individual variants be readily distinguishable from one another after, for example, assessment of encoded molecule properties. Methods for achieving this have been lacking. A need thus exists for methods of connecting specific encoded molecular phenotypes with corresponding genotypes of high complexity variant pools.

SUMMARY

The disclosure provides methods and compositions for high-throughput labeling of target molecules with specific nucleic acid barcodes (for example, origin-specific nucleic acid barcodes). The identity, quantity, and/or activity of target molecules and/or target nucleic acids originating from a particular sample, or portion thereof, can be determined by identifying the sequence of the origin-specific nucleic acid barcodes, optionally in combination with additional barcodes. Using this information the properties of the molecules can be determined. For example, the disclosed methods and compositions can be used to determine the affinity and/or specificity of a molecule, such as an antibody or antigen. Other aspects of the disclosed methods and compositions allow for the pairing of genotype characteristics to phenotype characteristics of a cell or sample, wherein alteration observed in target molecules and/or target nucleic acids can be tracked and/or associated with the sample of origin, and/or the differential test conditions, and/or the test agent being contacted, and the like.

Disclosed is a method of assigning a set of target molecules to specific compartment, while maintaining information about the origin of the target molecules, for example the origin of the compartment or discrete volume from which they were from or segregated into, which can be tied back to such information, for example including but not limited to, the conditions to which the molecules in that compartment were subjected to, the method includes: providing a sample comprising cells, or an acellular system; segregating single cells or a portion of the acellular system from the sample into individual compartments or discrete volumes, wherein each compartment or discrete volume further includes an origin-specific barcode, wherein the origin-specific barcode comprises a unique nucleic acid identification sequence that maintains or carries information about the origin of the cell or acellular system (such as compartment or volume origin) in the sample, for example the specific compartment; labeling the target molecules in individual compartments with the origin-specific barcodes present in the individual compartments to create origin-labeled target molecules, wherein the origin-labeled target molecules from each individual compartments comprise at least one of the same, or matched, unique indexing nucleic acid identification sequence(s); optionally processing the target molecules either individually or in a multiplex system; and detecting the nucleotide sequence of the origin-specific barcodes, thereby assigning the set of target molecules to a specific individual compartment, while maintaining information about compartment origin of the target molecules.

Also disclosed is a method of assigning the set of target molecules to target nucleic acids in the sample or set of samples while maintaining information about origin of the target molecules and target nucleic acids, wherein the sample comprises cells, or an acellular system, the method including: providing a sample comprising cells, or an acellular system; segregating single cells or a portion of the acellular system from the sample into individual compartments, wherein each individual compartment further includes an origin-specific barcode, the barcode comprising a unique nucleic acid identification sequence that maintains or carries information about the origin (such as compartment origin) of the cell or acellular system in the sample; labeling the target molecules and the target nucleic acids in the individual compartments with the origin-specific barcodes present in the individual compartments to create origin-labeled target molecules and origin-labeled target nucleic acids, wherein the origin-labeled target molecules from each individual compartment comprise the same, or matched, unique indexing nucleic acid identification sequence; optionally processing the target molecules either individually or in a multiplex system; and detecting the nucleotide sequence of the origin-specific barcodes, thereby assigning the set of target molecules to a target nucleic acids, while maintaining information about sample origin of the target molecules, such as the compartment origin.

Further disclosed is a method of determining a test agent's specificity for target molecules, comprising: assigning a set of target molecules to compartments; contacting the cells expressing target molecules, prior to segregation, with a pool of test agents labeled with a test agent specific barcode; isolating the target molecules bound to test agents; and determine the sequence of the test agent specific barcodes and the sequence of the origin specific barcode, thereby identifying the test agents bound to the target molecules.

Further disclosed is a method of determining a target molecules affinity and/or specificity for a test agent, comprising: assigning a set of target molecules to compartments; contacting the labeled target molecules with a test agent bound with a detectable label; isolating the labeled target molecules bound to the test agent using the detectable label; determine the sequence of origin-specific barcode on the isolated target molecules; and quantifying the origin-specific barcodes associated with the isolated target molecules, thereby determining the affinity of the test agent for the target molecules.

Further disclosed is a method of determining the expression of target molecules on the surface of a set of cells, comprising: assigning a set of target molecules to compartments; contacting the sample cells to be segregated with a set of test agents each labeled with a unique test agent barcode; determining the sequence of origin-specific barcode and the test agent specific barcode on the test agents bound to the cell, thereby determining the expression of molecules on the surface of the set of cells.

Further disclosed is a method of identifying a protein having a specific activity of interest from a population of cells, comprising: assigning a set of target molecules to compartments; isolating the target molecules having the specific activity of interest; identifying the origin-specific barcodes of the isolated target molecules having the specific activity interest.

Further disclosed is a barcode labeling complex, comprising a solid or semi-solid substrate, and a plurality of barcoding elements reversibly coupled thereto, wherein each of the barcoding elements comprises an indexing nucleic acid identification sequence and one or more of a nucleic acid capture sequence that specifically binds to target nucleic acids and a specific binding agent that specifically binds to the target molecules.

As will become apparent, this present disclosure provides several advantages over existing technology. For example, determination of inter-molecular affinity (for example, between an antibody and an antigen) using established approaches requires expensive and laborious assays (for example, ELISA). Furthermore, inter-molecular interactions may be assessed between a first protein and a second protein, a protein and a nucleic acid, and/or a first nucleic acid and a second nucleic acid using the methods and compositions of the invention. The methods of the present disclosure facilitate inter-molecular affinity determination by taking advantage of the speed, low cost, and capacity for multiplexing, and compatibility with next generation sequencing. This provides substantial benefits in, for example, designing high-value drugs or affinity binding reagents, as well as numerous other applications.

The foregoing and other objects and features of the disclosure will become more apparent from the following detailed description, which proceeds with reference to the accompanying figures.

BRIEF DESCRIPTION OF THE DRAWINGS

FIG. 5 is a schematic showing an exemplary analysis of affinity of labeled antibodies. After breakage of the emulsion, the labeled antibodies can be exposed to bulk antigen and captured, for example, on a column. Origin-specific barcodes can then be cleaved from the captured antibodies and sequenced. The origin-specific barcodes labeling unbound antibodies can be cleaved and sequenced separately. Sequencing and quantitative determination of the abundance of antibodies that remain bound versus unbound antibodies can be used to normalize concentration. Furthermore, this sequence information can be combined with RNA-Seq information from the origin-specific barcode labeled nucleic acids (for example, mRNAs or cDNAs), thereby coupling genotype information to phenotype information.

FIG. 7 is a schematic showing an exemplary analysis of affinity of binding moieties (for example, antibodies) labeled, for example, according to the scheme shown in FIG. 3. After breakage of the emulsion, the labeled specific binding agent-cell surface antigen complexes can be captured using a cell wall-specific affinity column. Origin-specific barcodes from each of the bound and unbound fractions can be separately cleaved and sequenced. Sequencing and quantitative determination of the abundance of antibodies that remain bound versus unbound antibodies can be used to normalize concentration. Furthermore, this sequence information can be combined with RNA-Seq information from the origin-specific barcode labeled nucleic acids (for example, mRNAs or cDNAs), thereby coupling genotype information to phenotype information.

FIG. 8 is a schematic of a tagged antigen structure. The structure includes streptavidin bound by a single antigen labeled with biotin and three biotin labeled nucleic acids that include nucleic acid barcodes, such as those described herein.

FIG. 25 is a schematic of a labeled antibody structure.

FIG. 35 shows the results for the analysis of the sequencing data. Expected heavy chain and light chain sequence pairs are shown on the top and the number and percentage of correct pairs obtained in the sequencing data is shown below. (SEQ ID NO: 34-57)

FIG. 38 shows the agarose gel with the amplified RT-in-drops product and the quality control analysis on Agilent's bioanalyzer made before sequencing.

DETAILED DESCRIPTION

I. Terms

Figure 1:
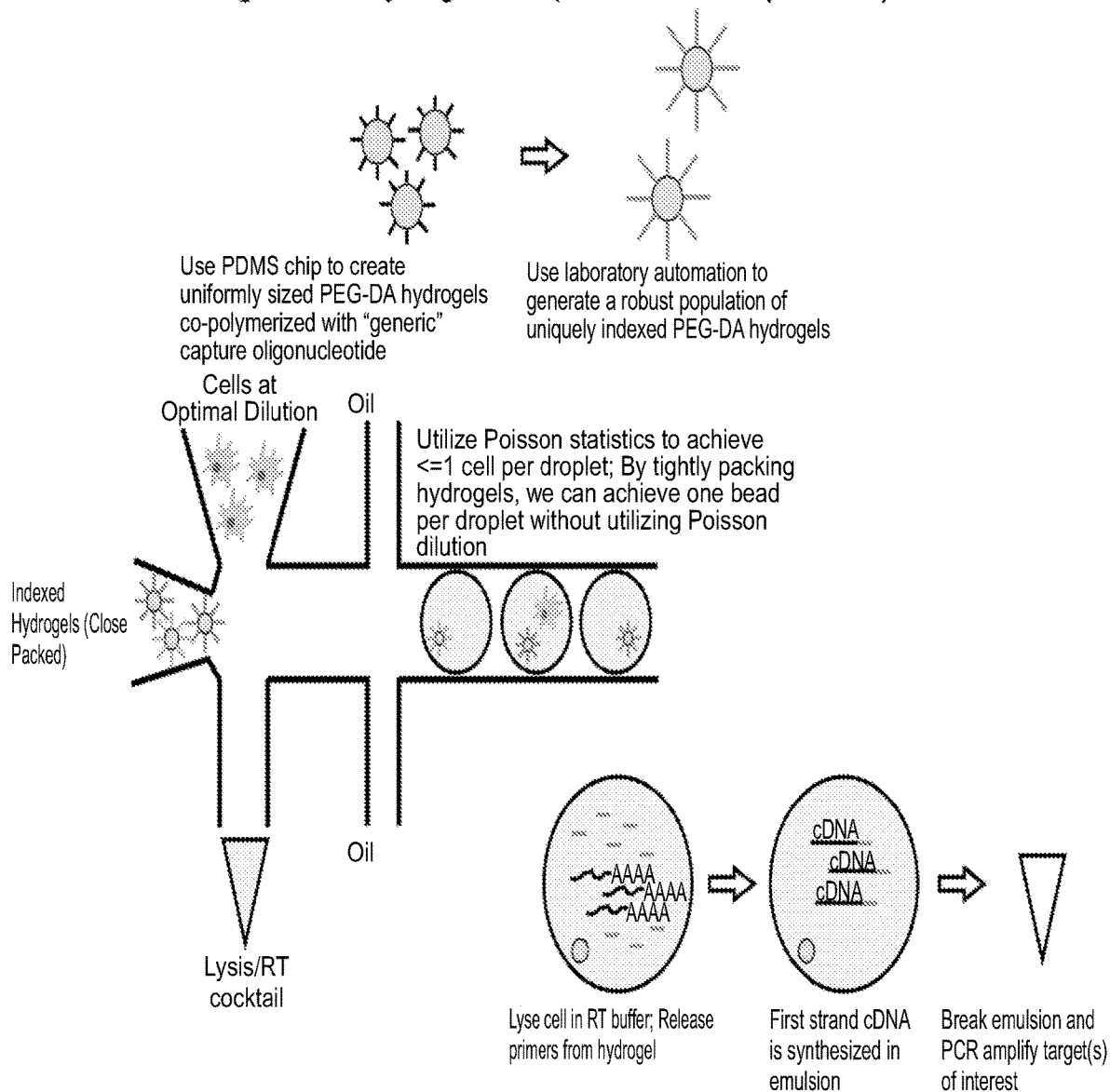
FIG. 1 is a schematic showing an exemplary method of labeling a set of amplicons from a set of cells.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

As used herein, the singular forms "a," "an," and "the," refer to both the singular as well as plural, unless the context clearly indicates otherwise. For example, the term "an origin-specific barcode" includes single or plural origin-specific barcodes and can be considered equivalent to the phrase "at least one origin-specific barcode."

As used herein, the term "comprises" means "includes." Thus, "an origin-specific barcode" means "including an origin-specific barcode" without excluding other elements.

Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Amplification: To increase the number of copies of a nucleic acid molecule, such as a nucleic acid molecule that includes an indexable nucleic acid identifier, such as an origin-specific barcode as described herein. The resulting amplification products are typically called "amplicons." Amplification of a nucleic acid molecule (such as a DNA or RNA molecule) refers to use of a technique that increases the number of copies of a nucleic acid molecule (including fragments). In some examples, an amplicon is a nucleic acid from a cell, or acellular system, such as mRNA or DNA that has been amplified.

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881), repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Antibody: A polypeptide ligand comprising at least a light chain and/or heavy chain immunoglobulin variable region (or fragment thereof) which specifically recognizes and binds an epitope of an antigen, such as a protein, or a fragment thereof. Antibodies can include a heavy and a light chain, each of which has a variable region, termed the variable heavy (VH) region and the variable light (VL) region. The term also includes recombinant forms such as chimeric antibodies (for example, humanized murine antibodies), heteroconjugate antibodies (such as, bispecific antibodies). An antibody or fragment thereof may be multispecific, for example, bispecific. Antibodies include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, an immunoconjugate, or a protein scaffold with antibody-like properties, such as fibronectin or ankyrin repeats. The antibody can have any of the following isotypes: IgG (for example, IgG1, IgG2, IgG3, and IgG4), IgM, IgA (for example, IgA1, IgA2, and IgAsec), IgD, or IgE.

In most mammals, including humans, whole antibodies have at least two heavy (H) chains and two light (L) chains connected by disulfide bonds. Each heavy chain includes a heavy chain variable region ($V_H$) and a heavy chain constant region ($C_H$). However, single chain $V_{HH}$ variants, such as found in camelids, and fragments thereof, are also included. The heavy chain constant region includes three domains, $C_H1$, $C_H2$, and $C_H3$ and a hinge region between $C_H1$ and $C_H2$. Each light chain includes a light chain variable region ($V_L$) and a light chain constant region. The light chain constant region includes the domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Included are intact immunoglobulins and the variants and portions of them well known in the art, such as Fab fragments, Fab' fragments, F(ab)'2 fragments, single chain Fv proteins ("scFv"), and disulfide stabilized Fv proteins ("dsFv") Fd, Feb, or SMIP. An antibody fragment may be, for example, a diabody, triabody, affibody, nanobody, aptamer, domain antibody, linear antibody, single-chain antibody, or multispecific antibodies formed from antibody fragments. Examples of antibody fragments include: (i) a Fab fragment: a monovalent fragment consisting of $V_L$, $V_H$, $C_L$, and $C_H1$ domains; (ii) a F(ab')$_2$ fragment: a bivalent fragment including two Fab fragments linked by a disulfide bridge at the hinge region; (iii) a Fd fragment: a fragment consisting of $V_H$ and $C_H1$ domains; (iv) a Fv fragment: a fragment consisting of the $V_L$ and $V_H$ domains of a single arm of an antibody; (v) a dAb fragment: a fragment including $V_H$ and $V_L$ domains; (vi) a dAb fragment: a fragment consisting of a $V_H$ domain or a $V_{HH}$ domain (such a Nanobody™); (vii) a dAb fragment: a fragment consisting of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, for example, by a synthetic linker that enables them to be made as a single protein chain in which the $V_L$ and $V_H$ regions pair to form monovalent molecules (known as single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more variable regions or constant regions derived from a first species and one or more variable regions or constant regions derived from a second species. Chimeric antibodies may be constructed, for example, by genetic engineering. A chimeric antibody may include immunoglobulin gene segments belonging to different species (for example, from a mouse and a human).

A human antibody refers to a specific binding agent having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, for example, mutations. A variation or additional amino acid may be introduced, for example, by human manipulation. A human antibody of the present disclosure is not chimeric.

Antibodies may be humanized, meaning that an antibody that includes one or more complementarity determining regions (for example, at least one CDR) substantially derived from a non-human immunoglobulin or antibody is manipulated to include at least one immunoglobulin domain having a variable region that includes a variable framework region substantially derived from a human immunoglobulin or antibody.

Antigen or Immunogen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In specific examples, an antigen is derived from HIV, such as a gp120, gp140, gp160 polypeptide or antigenic fragment thereof, such as a gp120 outer domain.

A "target epitope" is a specific epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody of interest.

Biotin-16-UTP: A biologically active analog of uridine-5"-triphosphate that is readily incorporated into RNA during an in vitro transcription reaction by RNA polymerases such as T7, T3, or SP6 RNA Polymerases. In some examples, biotin-16-UTP is incorporated into an origin-specific barcode (or any other barcode) during reverse transcription from a probe DNA template, for example during in vitro transcription with an RNA Polymerase, such as T7, T3, or SP6 RNA Polymerase.

Capture moieties: Molecules or other substances that when attached to another molecule, such as a nucleic acid barcode disclosed herein, allow for the capture of the targeting probe through interactions of the capture moiety and something that the capture moiety binds to, such as a particular surface and/or molecule, such as a specific binding molecule that is capable of specifically binding to the capture moiety. In specific examples, a capture moiety is biotin and a capture moiety specific binding agent is avidin or streptavidin.

Contacting: Placement in direct physical association, including both in solid or liquid form, for example contacting a sample with a nucleic acid barcode.

Conditions sufficient to detect: Any environment that permits the detection of the desired activity, for example, that permits detection and/or quantification of a nucleic acid, such as a nucleic acid barcode, a transcription product, and/or amplification product thereof.

Control: A reference standard. A control can be a known value or range of values indicative of basal levels or amounts or present in a tissue or a cell or populations thereof (such as a normal non-cancerous cell). A control can also be a cellular or tissue control, for example a tissue from a non-diseased state and/or exposed to different environmental conditions. A difference between a test sample and a control can be an increase or conversely a decrease. The difference can be a qualitative difference or a quantitative difference, for example a statistically significant difference.

Covalently linked: Refers to a covalent linkage between atoms by the formation of a covalent bond characterized by the sharing of pairs of electrons between atoms. In one example, a covalent link is a bond between an oxygen and a phosphorous, such as phosphodiester bonds in the backbone of a nucleic acid strand. In another example, a covalent link is one between nucleic acid barcode and a solid or semisolid substrate, such a bead, for example a hydrogel bead.

Detect: To determine if an agent (such as a signal or particular nucleic acid, such a nucleic acid barcode, or protein) is present or absent. In some examples, this can further include quantification in a sample, or a fraction of a sample, such as a particular cell or cells.

Detectable label: A compound or composition that is conjugated directly or indirectly to another molecule to facilitate detection of that molecule. Specific, non-limiting examples of labels include fluorescent tags, enzymatic linkages, and radioactive isotopes. In some examples, a label is attached to an antibody or nucleic acid to facilitate detection of the molecule antibody or nucleic acid specifically binds. In specific examples, a detectable label comprises a nucleic acid barcode, such as an origin-specific barcode.

DNA sequencing: The process of determining the nucleotide order of a given DNA molecule. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELIOSCOPE®). In some embodiments, the identity of a nucleic acid is determined by DNA or RNA sequencing. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELIOSCOPE®); Moleculo sequencing (see Voskoboynik et al. eLife 2013 2: e00569 and U.S. patent application Ser. No. 13/608,778, filed Sep. 10, 2012); DNA nanoball sequencing; Single molecule real time (SMRT) sequencing; Nanopore DNA sequencing; Sequencing by hybridization; Sequencing with mass spectrometry; and Microfluidic Sanger sequencing.

In some embodiments, DNA sequencing is performed using a chain termination method developed by Frederick Sanger, and thus termed "Sanger based sequencing" or "SB S." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing."

"Pyrosequencing" is an array based method, which has been commercialized by 454 Life Sciences. In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

Compartment: A discrete volume or discrete space, such as a container, receptacle, or other arbitrary defined volume or space that can be defined by properties that prevent and/or inhibit migration of target molecules, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof that can contain a target molecule and a indexable nucleic acid identifier (for example nucleic acid barcode). By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents maybe passed in our through the discrete volume, while other material, such as target molecules, maybe maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain embodiments, the compartment is an aqueous droplet in a water-in-oil emulsion.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or it's analog) and the DNA or RNA target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Isolated: An "isolated" biological component (such a nucleic acid) has been substantially separated or purified away from other biological components in the cell of the organism in which the component naturally occurs, for example, extra-chromatin DNA and RNA, proteins and organelles. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Level of expression: may refer to levels of RNA expression, levels of protein expression, or both.

Nucleic acid (molecule or sequence): A deoxyribonucleotide or ribonucleotide polymer including without limitation, cDNA, mRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein.

The major building blocks for polymeric nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major building blocks for polymeric nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

In some examples, nucleotides include those nucleotides containing modified bases, modified sugar moieties, and modified phosphate backbones, for example as described in U.S. Pat. No. 5,866,336 to Nazarenko et al. Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others. Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphorodiamidate, a methylphosphonate, an alkyl phosphotriester, or a formacetal or analog thereof.

Nucleic acid barcode, barcode, unique molecular identifier, or UMI: A short sequence of nucleotides (for example, DNA, RNA, or combinations thereof) that is used as an identifier for an associated molecule, such as a target molecule and/or target nucleic acid. A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. One or more nucleic acid barcodes and/or UMIs can be attached, or "tagged," to a target molecule and/or target nucleic acid. This attachment can be direct (for example, covalent or noncovalent binding of the barcode to the target molecule) or indirect (for example, via an additional molecule, for example, a specific binding agent, such as an antibody (or other protein) or a barcode receiving adaptor (or other nucleic acid molecule). Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular compartment (for example a discrete volume), having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of) the same molecule as) individual members of a particular set of identical, specific (for example, discrete volume-, physical property-, or treatment condition-specific) nucleic acid barcodes. Thus, for example, each member of a set of origin-specific nucleic acid barcodes, having identical or matched barcode sequences, may be associated with (for example, covalently bound to or a component of the same molecule as) a distinct or different UMI.

Nucleic acid capture sequence: A nucleic acid sequence that specifically binds another nucleic acid, such as target nucleic acids and/or a barcode, such as a origin-specific barcode, or target molecule identification barcode and the like. A nucleic acid capture sequence (for example, a DNA, RNA, or hybrid molecule) may recognize a target nucleic acid molecule (for example, a DNA or RNA molecule) by hybridization or base-pairing interactions. Such capture sequence can be a single-stranded or have an overhang portion including nucleic acid sequences that can hybridize to sequences of target nucleic acid molecules. In some instances, a nucleic acid capture sequence can be attached to a nucleic acid barcode, for example by ligation, or by synthesizing both the nucleic acid specific binding agent and barcode as a single, contiguous nucleic acid. The length of sequences required for hybridization can vary depending, for example, on nucleotide content and conditions used but, in general, can be at least 4, 8, 12, 16, 20, 25, 30, 40, 50, 75, or 100 nucleotides in length.

Primers: Short nucleic acid molecules, such as a DNA oligonucleotide, for example sequences of at least 15 nucleotides, which can be annealed to a complementary nucleic acid molecule by nucleic acid hybridization to form a hybrid between the primer and the nucleic acid strand. A primer can be extended along the nucleic acid molecule by a polymerase enzyme. Therefore, primers can be used to amplify a nucleic acid molecule, wherein the sequence of the primer is specific for the nucleic acid molecule, for example so that the primer will hybridize to the nucleic acid molecule under very high stringency hybridization conditions. The specificity of a primer increases with its length. Thus, for example, a primer that includes 30 consecutive nucleotides will anneal to a sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a nucleic acid molecule. Particular lengths of primers that can be used to practice the methods of the present disclosure, include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, MA).

Methods for preparing and using primers are described in, for example, Sambrook et al. (1989) *Molecular Cloning: A Laboratory Manual*, Cold Spring Harbor, New York; Ausubel et al. (1987) *Current Protocols in Molecular Biology*, Greene Publ. Assoc. & Wiley-Intersciences. In one example, a primer includes a label.

Probe: An isolated nucleic acid capable of hybridizing to a specific nucleic acid (such as a nucleic acid barcode or target nucleic acid). A detectable label or reporter molecule can be attached to a probe. Typical labels include radioactive isotopes, enzyme substrates, co-factors, ligands, chemiluminescent or fluorescent agents, haptens, and enzymes. In some example, a probe is used to isolate and/or detect a specific nucleic acid.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

Probes are generally about 15 nucleotides in length to about 160 nucleotides in length, such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 contiguous nucleotides complementary to the specific nucleic acid molecule, such as 50-140 nucleotides, 75-150 nucleotides, 60-70 nucleotides, 30-130 nucleotides, 20-60 nucleotides, 20-50 nucleotides, 20-40 nucleotides, or 20-30 nucleotides.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215: 403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

Specific Binding Agent: An agent that binds substantially or preferentially only to a defined target such as a polypeptide protein, enzyme, polysaccharide, oligonucleotide, DNA, RNA, recombinant vector or a small molecule. In an example, a "capture moiety specific binding agent" is capable of binding to a capture moiety that is linked to a nucleic acid, such as a nucleic acid barcode.

A nucleic acid-specific binding agent binds substantially only to the defined nucleic acid, such as RNA, or to a specific region within the nucleic acid. In some embodiments a specific binding agent is a nucleic acid barcode, that specifically binds to a target nucleic acid of interest.

A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Support: A solid or semisolid substrate to which something can be attached, such as a nucleic acid barcode, for example an origin-specific barcode. The attachment can be a removable attachment. Non-limiting examples of a support useful in the methods of the disclosure include a hydrogel, cell, bead, column, filter, slide surface, or interior wall of a compartment, such as a well in a microtiter plate, or vessel. In certain embodiments, the support is a hydrogel (such as a hydrogel bead) to which one or more origin-specific barcodes is coupled. A origin-specific barcodes reversibly coupled to a support can be detached from the support, for example enzymatic cleavage of a cleavage site on the origin-specific barcode. A support may be present in a compartment as set forth herein. In certain embodiments, the support is a hydrogel bead present in an emulsion droplet.

Target Molecule: A molecule, or in some examples a molecular complex, about which information is desired, for example origin, expression, type and the like. In some embodiments, a target molecule is labeled according to the methods disclosed herein. Examples of target molecules include, but are not limited to, peptides, polypeptides, proteins, antibodies, antibody fragments, amino acids, nucleic acids (such as RNA and DNA), nucleotides, carbohydrates, polysaccharides, lipids, small molecules, organic molecules, inorganic molecules, and complexes thereof. In some examples, a plurality of target molecules can be present in a sample, such as a sample that has been separated into a compartment such as a discrete volume or space (for example, multiple copies of the same target molecule or more than one distinct target molecule). In certain embodiments, a target nucleic acid molecule (for example, an RNA molecule) encodes a polypeptide target molecule (for example, a protein) present in the compartment. In particular embodiments, the polypeptide target molecule and the nucleic acid target molecule are expressed by a cell or cell-free expression system present in a compartment.

A target molecule can be bound by a specific binding agent associated with a nucleic acid barcode, such that the target molecule is labeled with the nucleic acid barcode, for examples an origin-specific barcode and/or a target molecule specific barcode. A plurality of target molecules, for example multiple copies of the same target molecule or multiple copies of more than one distinct target molecule, can be present in a compartment, such as a discrete volume or space, and labeled. In certain embodiments, a target nucleic acid molecule (such as a DNA or an RNA molecule) encodes a target molecule, such as a target protein present in the same compartment, and the target nucleic acid molecule and the polypeptide target molecule are labeled with the same barcode or matching barcodes (for example barcodes pre-identified as corresponding to one another) such as origin-specific nucleic acid barcodes. In particular embodiments, a target molecule and a target nucleic acid molecule are expressed by a cell or cell-free expression system present in specific compartment.

Target nucleic acid molecule: Any nucleic acid present or thought to be present in a sample about which information would like to be obtained. In some embodiments, a target nucleic acid of interest is an RNA, such as an mRNA, for example an mRNA encoding a target molecule. In some embodiments, a target nucleic acid of interest is a DNA.

Test agent: Any agent that is tested for its effects, for example its effects on a cell or target molecule of interest. In some embodiments, a test agent is a chemical compound, such as a chemotherapeutic agent, antibiotic, or even an agent with unknown biological properties. In some examples, a test agent is a polypeptide or protein, such as an antibody, antigen, or immunogen.

Under conditions that permit binding: A phrase used to describe any environment that permits the desired activity, for example conditions under which two or more molecules, such as nucleic acid molecules and/or protein molecules, can bind.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

II. Description of Several Embodiments

A. Introduction

The present disclosure provides methods and compositions for high-throughput labeling of target molecules with specific nucleic acid barcodes. The identity, quantity, and/or activity of target molecules can be determined in multiplex using origin-specific nucleic acid barcodes that specifically label the target molecules, for example by detecting the sequence of the nucleic acid barcodes, such as by sequencing or other methodology that provide information on the sequence of a nucleic acid. Because the origin-specific barcodes can be traced back to the original sample or subsample (for example individual compartment), the target molecules and/or target nucleic acids originated from, samples can be split, differentially treated and then pooled for multiplex analysis. Thus, the methods and compositions of this disclosure enable highly complex combinatorial analyses by associating information, such as phenotype information, about different target molecules, their sources, physical characteristics, and/or different treatment conditions with distinct nucleic acid barcodes, which can be de-convoluted from pooled samples, for example using high-throughput sequencing technologies.

The disclosure also features simultaneous co-labeling of target polypeptides (such as antibodies, antigens and immunogens) and DNA or RNA molecules of interest (for example DNA (such as cDNA) and/or RNA encoding the co-labeled target polypeptides, or DNA and/or RNA of a reporter cell line) with the same or matched origin-specific nucleic acid barcodes, enabling, for example, coupling of a genotype to a phenotype of interest. As such, the present disclosure enables rapid, massively multiplex screening of candidate target molecules. The methods of the disclosure can further be used in the characterization of gene expression systems in the form of, for example, multi-part DNA assemblies, in massively multiplex form.

In the non-limiting case of application of the disclosed methods to antibodies, the affinity of an antibody (or set of antibodies) for a particular target (such as protein and/or particular epitope found on a protein) can be determined. In a further example, the methods disclosed herein can be used to potentially determine the expression, such as relative expression, of cell surface markers on a cell type (or types) of interest. By utilizing an array, or set, of antibodies labeled with indexable nucleic acid identifiers, a population of cells can be analyzed in multiplex to determine the cell surface markers expressed on individual cells, for example individual cells segregated into individual compartments.

In various examples of the methods of the disclosure, a phenotype of an individual cell or molecule (for example, binding characteristics of an antibody produced by a cell) can be linked to a corresponding genotype (i.e., a nucleic acid molecule such as, for example, a nucleic acid molecule encoding the antibody). This can be done after the pooling and en masse screening (for example, by highly multiplexed affinity measurement) of a large number of the cells or target molecules (for example, antibodies) produced by the cells. The disclosure thus provides high-throughput approaches for coupling genotype to phenotype (for example, antibody expression) in, if desired, a massively multiplex context.

B. Methods of Indexing

Disclosed herein are methods of coupling, or indexing, a genotype to a phenotype, for example by assigning a set of target molecules to target nucleic acids in a sample, or set of samples, while maintaining information about sample origin of the target molecules and target nucleic acids. In other words, using the methods disclosed herein, a specific target molecule can be paired with a specific target nucleic acid, or in some cases sets of target nucleic acids and target molecules. The disclosed methods include the labeling of target molecules and/or target nucleic acids with distinct nucleic acid barcodes associated with a particular compartment so the origin of the molecules within, or labeled within the individual compartments can be determined at a later time, for example at the end of an experiment. A target molecule and/or target nucleic acid can be labeled with a nucleic acid barcode that is already present upon introduction into, or production of, the target molecule and/or target nucleic acid, in the compartment.

Certain embodiments of the disclosed methods include providing a sample that includes cells, or in some situations an acellular system and segregating single cells from the sample, or a discrete portion of the acellular system from the sample, into individual compartments. Each of the compartments also includes an origin-specific barcode that includes a unique nucleic acid identification sequence (such as a unique nucleic acid identification sequence that includes DNA, RNA, or combination thereof) that maintains or carries information about the origin of the cell or acellular system in the sample, such as which compartment the labeled target molecules and/or target nucleic acids came from, for example after pooling and analysis. In this way, the compartment is effectively labeled with the origin-specific barcode, such that the origin-specific barcode can be used to trace the contents of the compartment throughout an experiment and/or analysis, for example an experiment and/or analysis in which the individual compartments are exposed to different conditions to measure the effect the conditions have on target molecules and/or target nucleic acids. The target molecules and/or target nucleic acid present in the compartments are labeled with the origin-specific barcodes present in the compartments to create origin-labeled molecules and/or origin-labeled nucleic acids. As discussed above, the origin-labeled molecules and/or origin-labeled nucleic acids from each compartment carry the same, or matched, unique indexing nucleic acid identification sequence or origin-specific barcode. The nucleotide sequence of the origin-specific barcodes is detected, thereby assigning the set of target molecules to target nucleic acids in the sample or set of samples while maintaining information about sample or compartment origin of the target molecules and target nucleic acids. The sequence of the origin-specific barcode, amongst other sequences (such as the sequences of the target nucleic acids and/or other barcodes), can be detected by any method known in the art, such as by amplification, sequencing, hybridization or any combination thereof.

Figure 2:
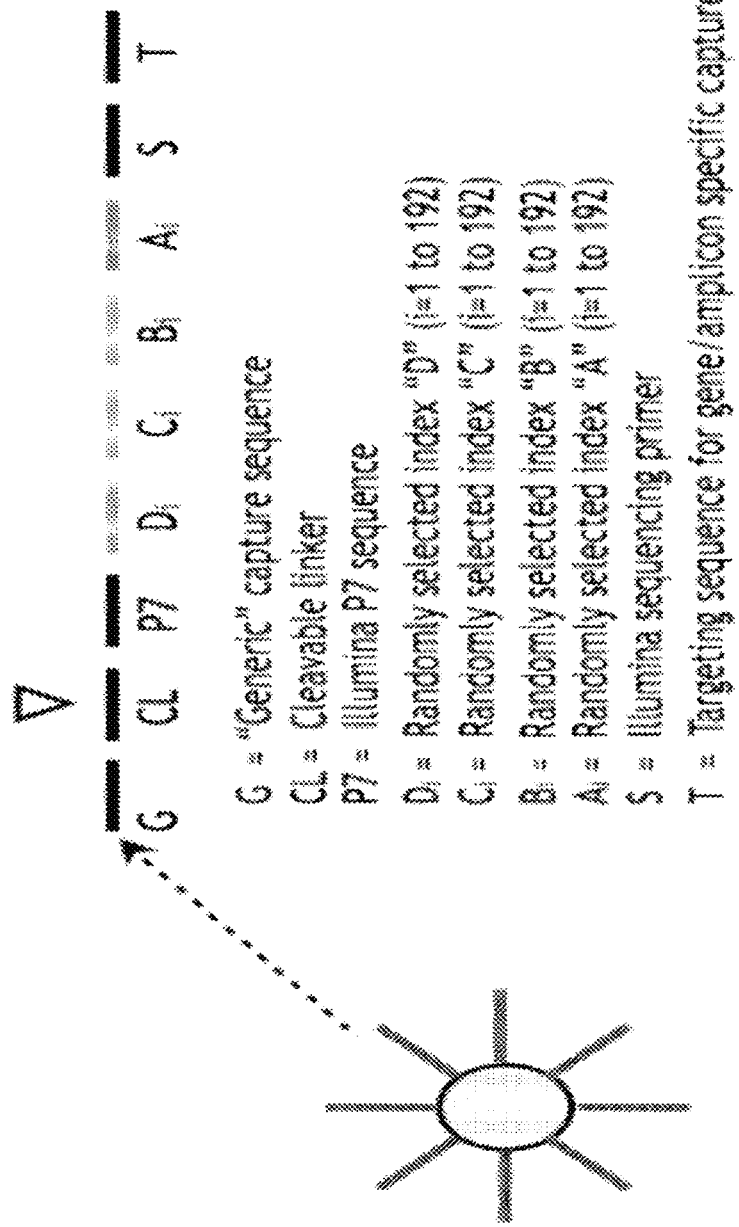
FIG. 2 is a schematic showing an exemplary composition of a bead comprising an origin-specific barcode for labeling a set of amplicons according to the method of FIG. 1. In this example each hydrogel bead carries a clonal population of a randomly constructed, multi-part index sequence (for example $D_i/C_i/B_i/A_i$) plus sequences that enable gene specific capture/amplification and Illumina® library construction, G="Generic" capture sequence; CL1=Cleavable linker 1 (RNA or other to release from bead); P7=Illumina® P7 sequence; $D_i$=Randomly selected index "D" (i=e.g., 1 to 192); $C_i$=Randomly selected index "C" (i=e.g., 1 to 192); $B_i$=Randomly selected index "B" (i=e.g., 1 to 192); $A_i$=Randomly selected index "A" (i=e.g., 1 to 192); S=Illumina® sequencing primer; V=Targeting sequence for gene/amplicon specific capture; CL2=Cleavable linker 2 (to release from captured Ab or protein); X=Capture protein or antibody (e.g., protein G for antibodies).

In some embodiments, the method is used to label a set of target molecules that are nucleic acids from a sample, such as the amplicons from a cell, set or cells, or an acellular system. An example of this method is shown in FIG. 1. In such a method, the nucleic acids from a single compartment are labeled with a specific origin-specific barcode (an example of which is shown in FIG. 2), while nucleic acids from another, or a plurality of other compartments are labeled with different origin-specific barcodes, allowing for multiplex analysis of the nucleic acids, for example to study gene expression differences in the individual compartments, for example when exposed to different conditions, or being of different cell types.

As disclosed herein, unique nucleic acid identifiers, such as nucleic acid barcodes, are used to label the target molecules and/or target nucleic acids, for example origin-specific barcodes and the like. The nucleic acid identifiers, such as nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a binding moiety that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www.drmr.com/abcon). In certain embodiments, barcode tagging can occur via a barcode receiving adapter associated with (for example, attached to) a target molecule, as described herein.

Target molecules can be optionally labeled with multiple barcodes in combinatorial fashion (for example, using multiple barcodes bound to one or more specific binding agents that specifically recognize the target molecule), thus greatly expanding the number of unique identifiers possible within a particular barcode pool. In certain embodiments, barcodes are added to a growing barcode concatemer attached to a target molecule, for example, one at a time. In other embodiments, multiple barcodes are assembled prior to attachment to a target molecule. Compositions and methods for concatemerization of multiple barcodes are described, for example, in International Patent Publication No. WO 2014/047561, which is incorporated herein by reference in its entirety.

Unique molecular identifiers are a subtype of nucleic acid barcode that can be used, for example, to normalize samples for variable amplification efficiency. For example, in various embodiments, featuring a solid or semisolid support (for example a hydrogel bead), to which nucleic acid barcodes (for example a plurality of barcode sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid identifier can further include a unique molecular identifier and/or additional barcodes specific to, for example, a common support to which one or more of the nucleic acid identifiers are attached. Thus, a pool of target molecules can be added, for example, to a compartment containing multiple solid or semisolid supports (for example, beads) representing distinct treatment conditions (and/or, for example, one or more additional solid or semisolid support can be added to the compartment sequentially after introduction of the target molecule pool), such that the precise combination of conditions to which a given target molecule was exposed can be subsequently determined by sequencing the unique molecular identifiers associated with it.

Labeled target molecules and/or target nucleic acids associated with origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprise a sequencing adaptor. In some embodiments, an origin-specific barcode further comprises universal priming sites. In some embodiments, a nucleic acid identifier (for example, a nucleic acid barcode) may be attached to sequences that allow for amplification and sequencing (for example, P7 (SEQ ID NO: 11), SBS3 (SEQ ID NO: 2) and P5 (SEQ ID NO: 12) elements for Illumina® sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type (SEQ ID NO: 1). Other lengths and components of contemplated barcodes for use in the invention are provided throughout the disclosure.

A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina® sequencing, Ion Torrent sequencing, 454 sequencing, SOLiD sequencing, and nanopore sequencing amongst others.

In some embodiments, the sequence of labeled target molecules is determined by non-sequencing based methods. For example, variable length probes or primers can be used to distinguish barcodes (for example, origin-specific barcodes) labeling distinct target molecules by, for example, the length of the barcodes, the length of target nucleic acids, or the length of nucleic acids encoding target polypeptides. In other instances, barcodes can include sequences identifying, for example, the type of molecule for a particular target molecule (for example, polypeptide, nucleic acid, small molecule, or lipid). For example, in a pool of labeled target molecules containing multiple types of target molecules, polypeptide target molecules can receive one identifying sequence, while target nucleic acid molecules can receive a different identifying sequence. Such identifying sequences can be used to selectively amplify barcodes labeling particular types of target molecules, for example, by using PCR primers specific to identifying sequences specific to particular types of target molecules. For example, barcodes labeling polypeptide target molecules can be selectively amplified from a pool, thereby retrieving only the barcodes from the polypeptide subset of the target molecule pool.

In some embodiments of the disclosed methods, determining the identity of a nucleic acid, such as a nucleic acid barcode, includes detection by nucleic acid hybridization. Nucleic acid hybridization involves providing a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (for example, low temperature and/or high salt) hybrid duplexes (for example, DNA:DNA, RNA:RNA, or RNA:DNA) will form even where the annealed sequences are not perfectly complementary. Thus, specificity of hybridization is reduced at lower stringency. Conversely, at higher stringency (for example, higher temperature or lower salt) successful hybridization requires fewer mismatches. One of skill in the art will appreciate that hybridization conditions can be designed to provide different degrees of stringency.

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest. In some examples, RNA is detected using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992).

In one embodiment, the hybridized nucleic acids are detected by detecting one or more labels attached to the sample nucleic acids. The labels can be incorporated by any of a number of methods. In one example, the label is simultaneously incorporated during the amplification step in the preparation of the sample nucleic acids. Thus, for example, polymerase chain reaction (PCR) with labeled primers or labeled nucleotides will provide a labeled amplification product. In one embodiment, transcription amplification, as described above, using a labeled nucleotide (such as fluorescein-labeled UTP and/or CTP) incorporates a label into the transcribed nucleic acids.

Detectable labels suitable for use include any composition detectable by spectroscopic, photochemical, biochemical, immunochemical, electrical, optical or chemical means. Useful labels include biotin for staining with labeled streptavidin conjugate, magnetic beads (for example DYNABEADS'), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology*, Vol. 24: *Hybridization With Nucleic Acid Probes*, P. Tijssen, ed. Elsevier, N.Y., 1993).

In some embodiments, labeling of the target molecule includes directly attaching the origin-specific barcode to the target molecule. In some embodiments, labeling of the target molecule includes attaching the origin-specific barcode to the target molecule indirectly. Indirect attachment includes binding a target molecule specific binding agent to the target molecule, where the target molecule specific binding agent is indirectly or directly attached to the origin-specific barcode, for example covalently attached. In certain embodiments, a specific binding agent is an antibody, such as a whole antibody or an antibody fragment, such as an antigen-binding fragment. A specific binding agent can alternatively be a protein or polypeptide that is not an antibody. A specific binding agent may thus be, for example, a kinase, a phosphatase, a proteasomal protein, a protein chaperone, a receptor (for example, an innate immune receptor or signaling peptide receptor), a synbody, an artificial antibody, a protein having a thioredoxin fold (for example, a disulfide isomerase, DsbA, glutaredoxin, glutathione S-transferase, calsequestrin, glutathione peroxidase, or glutathione peroxiredoxin), a protein having a fold derived from a thioredoxin fold, a repeat protein, a protein known to participate in a protein complex, a protein known in the art as a protein capable of participating in a protein-protein interaction, or any variant thereof (for example, a variant that modifies the structure or binding properties thereof). A specific binding agent can be any protein or polypeptide having a protein binding domain known in the art, including any natural or synthetic protein that includes a protein binding domain. A specific binding agent can also be any protein or polypeptide having a polynucleotide binding domain known in the art, including any natural or synthetic protein that includes a polynucleotide binding domain. In some instances, a specific binding agent is a recombinant specific binding agent.

A specific binding agent (for example, an antibody) can, for example, be attached to a nucleic acid barcode (for example, an origin-specific barcode). For example, the specific binding agent may include a cysteine residue that can be attached to a nucleic acid barcode. In other instances, a binding moiety can be a nucleic acid attached to a barcode. A specific binding agent attached to a nucleic acid barcode can recognize a target molecule of interest. A nucleic acid barcode may identify a specific binding agent as recognizing a particular target molecule of interest. A nucleic acid barcode may be cleavable from a specific binding agent, for example, after the specific binding agent has bound to a target molecule.

A nucleic acid barcode can be sequenced, for example, after cleavage, to determine the presence, quantity, or other feature of the target molecule. In certain embodiments, a nucleic acid barcode can be further attached to a further nucleic acid barcode. For example, a nucleic acid barcode can be cleaved from a binding moiety after the binding moiety binds to a target molecule or a tag (for example, an encoded peptide tag cleaved from a target molecule), and then the nucleic acid barcode can be ligated to an origin-specific barcode. The resultant nucleic acid barcode concatemer can be pooled with other such concatemers and sequenced. The sequencing reads can be used to identify which target molecules were originally present in which compartment.

In some embodiments, the target molecule comprises a target polypeptide and the specific binding agent that specifically binds to the target molecule in the sample comprises a polypeptide specific binding agent that specifically binds to a target polypeptide. In some embodiments, the polypeptide specific binding agent comprises an antibody, or fragment thereof and/or a protein-binding domain or fragment thereof, or a nucleic acid sequence that specifically binds to the target polypeptide, for example if the target polypeptide includes a nucleic acid binding domain. In some embodiments the target molecule specific binding agent specifically binds both the target molecule and the origin-specific barcode. In some examples, the target molecule is incubated with the target molecule specific binding agent that bind both the target molecules and the origin-specific barcode and the target molecule specific binding agents are not bound to the target molecule and/or origin-specific barcode are removed prior to segregation into individual compartments. In some examples, the target molecule specific binding agent comprises a target molecule specific binding agent barcode, encoding the identity of the target molecule specific binding agent. In some examples, the target molecule specific binding agent barcode can bind to the origin-specific barcode via base-pairing interactions. In specific examples, the origin-specific barcode is a primer for the synthesis of the complementary strand of the target molecule specific binding agent barcode. In some examples, the sequence of the target molecule specific binding agent barcode, amongst other sequences, is be detected. The sequence of the target molecule specific binding agent barcode can be detected by any method known in the art, such as by amplification, sequencing, hybridization and any combination thereof. In addition to origin-specific nucleic acid barcodes, target molecules can be labeled with additional nucleic acid barcodes (optionally in the form of a nucleic acid barcode concatemer) in a specific manner based on any of a number of different properties of the target molecules and/or conditions to which they are exposed, facilitating further levels of characterization. In still other embodiments, the target molecule is a polypeptide and it is directly labeled with a nucleic acid barcode, such as a target molecule specific binding agent and/or origin-specific barcode via encoded cysteine residues, for example, a C-terminal cysteine residue.

In particular examples, the sequence of the target molecule specific binding agent barcode is amplified, for example using PCR. A nucleic acid encoding an antigen or specific binding agent can be sub-cloned into an expression vector for protein production, for example, an expression vector for production of binding moieties in, for example, E. coli. Produced binding moieties may be purified, for example, by affinity chromatography. In embodiments in which a specific binding agent includes one or more fragments substantially similar to an antibody or antibody fragment, the fragments may be incorporated into known antibody frameworks for expression. For instance, if a specific binding agent is an scFv, the heavy and light chain sequences of the scFv may be cloned into a vector for expression of those chains within an IgG molecule.

In some embodiments, a target molecule comprises a target nucleic acid, such as a DNA or RNA and the specific binding agent that specifically binds to the target molecules in the sample comprises a nucleic acid sequence or nucleic acid binding domain that specifically binds, and/or hybridizes to the target nucleic acid. Target nucleic acids include RNA, such as mRNA, and DNA, such as cDNA. In some embodiments of the disclosed methods, cDNAs synthesized from the target nucleic acids, wherein the cDNA comprises the nucleic acid sequence of the target nucleic acid, or a fragment thereof and the sequence of the origin-specific barcode. In some example, the origin-specific barcodes are primers for the cDNA synthesis. In certain embodiments, the target nucleic acid, or complement thereof, encode a polypeptide of interest. In some embodiments, the target molecule comprises a target DNA and the specific binding agent that specifically binds to the target molecules in the sample comprises a nucleic acid sequence or DNA binding domain that specifically binds, and/or hybridizes to the target DNA.

Figure 3:
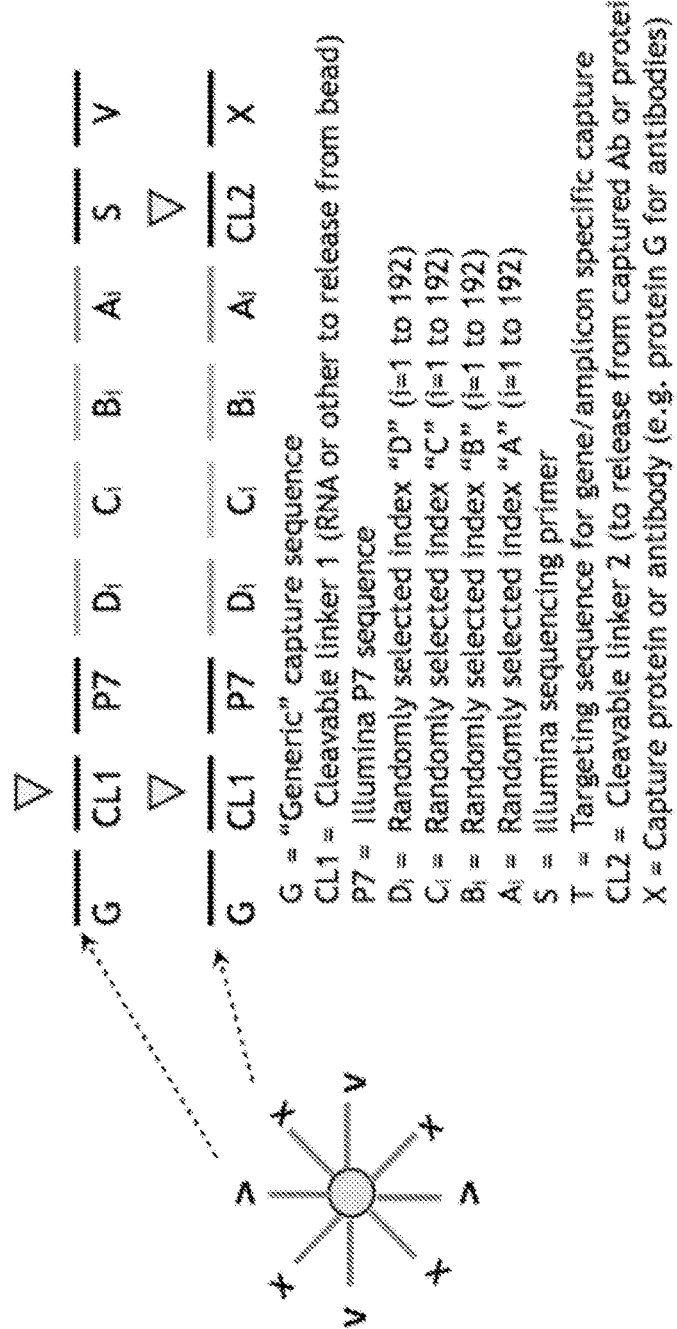
FIG. 3 is a schematic showing an exemplary composition of a bead comprising an origin-specific barcode for labeling both target nucleic acids and target molecules. In this example each hydrogel bead carries (i) a clonal population of a randomly constructed, multi-part index sequence ($D_i/C_i/B_i/A_i$) plus sequences that enable gene specific capture/amplification and Illumina® library construction, and (ii) a second population of antibody or protein capture sequences each attached to a clonal population of, e.g., the same multi-part index sequence. These multi-part index sequences make up origin-specific barcodes. G="Generic" capture sequence; CL1=Cleavable linker 1 (RNA or other to release from bead); P7=Illumina® P7 sequence; $D_i$=Randomly selected index "D" (i=e.g., 1 to 192); $C_i$=Randomly selected index "C" (i=e.g., 1 to 192); $B_i$=Randomly selected index "B" (i=e.g., 1 to 192); $A_i$=Randomly selected index "A" (i=e.g., 1 to 192); S=Illumina® sequencing primer; V=Targeting sequence for gene/amplicon specific capture; CL2=Cleavable linker 2 (to release from captured Ab or protein); X=Capture protein or antibody (e.g., protein G for antibodies).
Figure 4:
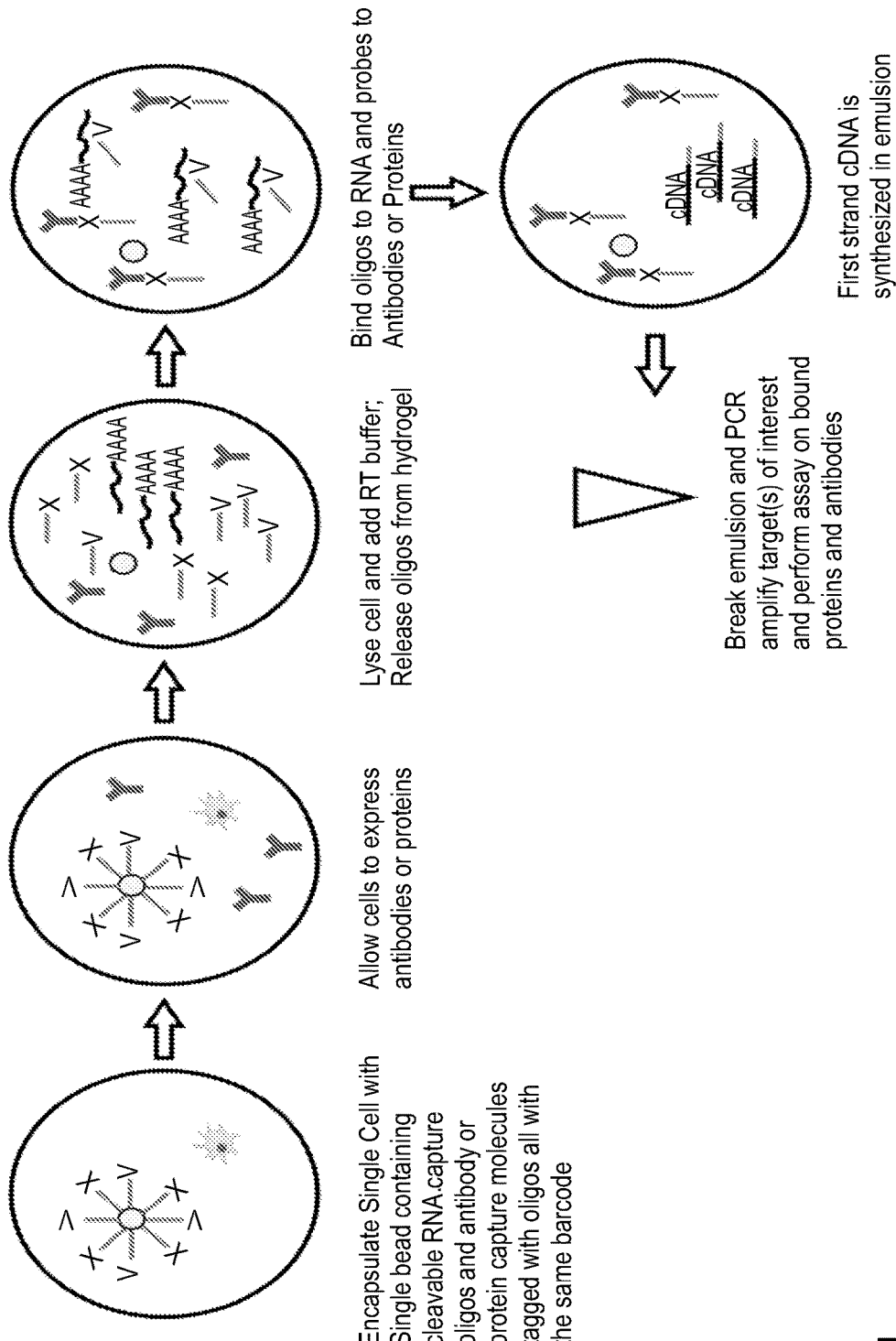
FIG. 4 is a schematic showing an exemplary method for simultaneous barcoding of amplicons and expressed antibodies or proteins using indexed hydrogels. In brief, this exemplary method involves the following steps. A single cell and a single indexed hydrogel bead are, for example, encapsulated in an emulsion droplet. The cell expresses, for example, antibodies or proteins. Upon cell lysis, the expressed antibodies and proteins, together with nucleic acids (for example, mRNAs or cDNAs), are tagged with the origin-specific barcodes. Multiple barcoded samples can then be pooled (for example, by breaking the emulsion). Individual constructs can be retrieved by PCR and/or assays can be performed on the labeled antibodies or proteins.
Figure 6:
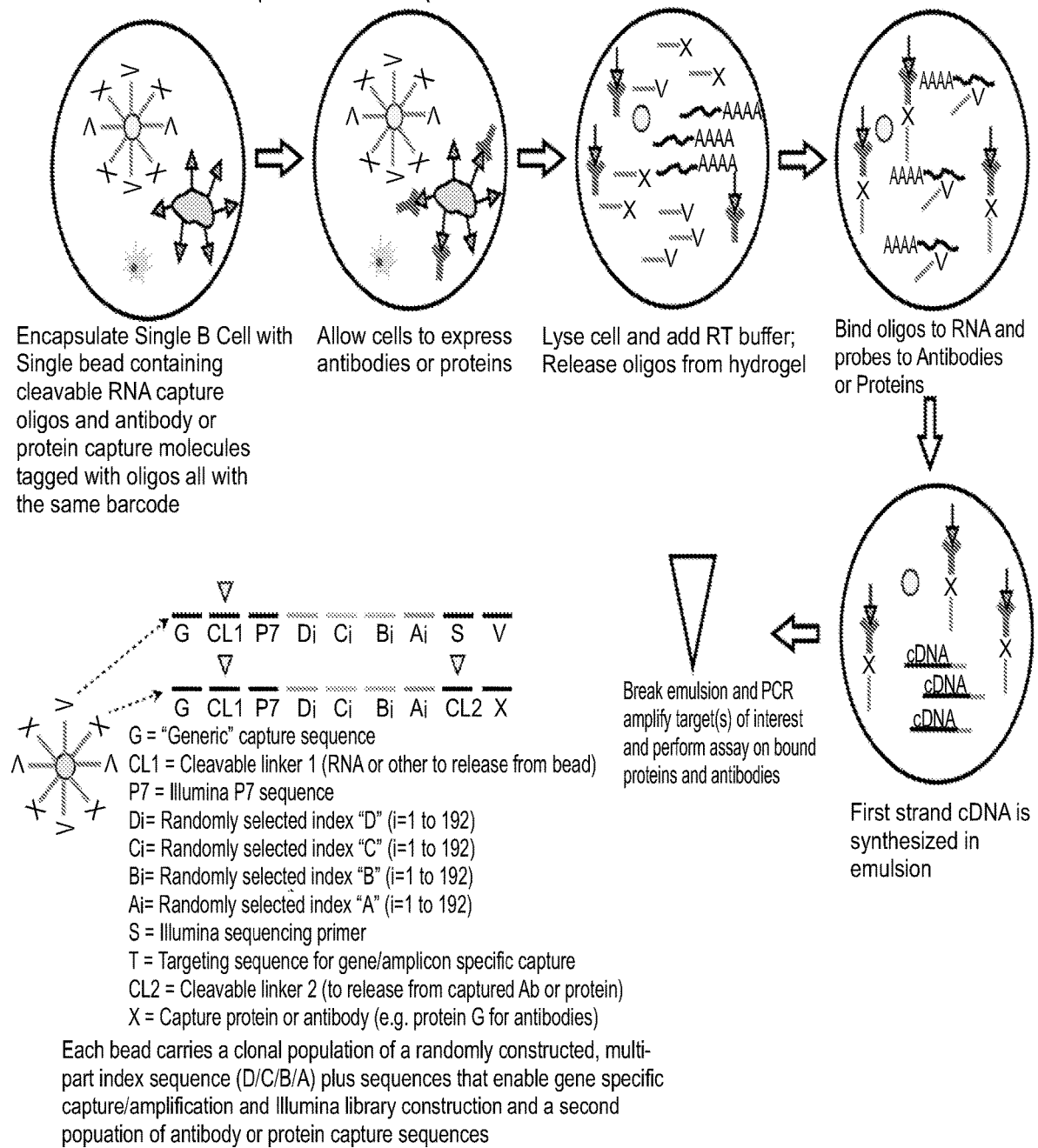
FIG. 6 is a schematic showing an exemplary alternate method for simultaneous barcoding of amplicons and expressed antibodies or proteins using indexed hydrogels. Each hydrogel bead carries (i) a clonal population of a randomly constructed, multi-part index sequence ($D_i/C_i/B_i/A_i$) plus sequences that enable gene specific capture/amplification and Illumina® library construction, and (ii) a second population of antibody or protein capture sequences each attached to a clonal population of, for example, the same multi-part index sequence. These multi-part index sequences make up origin-specific barcodes. In brief, the method includes the following steps. A specific binding agent-expressing cell (for example, a B cell) is encapsulated in an emulsion droplet with a single indexed hydrogel bead and a target cell expressing cell surface antigens. The cell is allowed to express binding moieties (for example, antibodies or proteins), which can be secreted and subsequently bind to cell surface antigens on the target cell. The cells can then be lysed, releasing nucleic acids, cell surface antigens, and bound binding moieties. The binding moieties and nucleic acids can then be labeled with origin-specific barcodes and pooled (for example, by breaking the emulsion). Individual constructs can be retrieved by PCR and/or assays can be performed on the labeled antibodies or proteins. G="Generic" capture sequence; CL1=Cleavable linker 1 (RNA or other to release from bead); P7=Illumina® P7 sequence; $D_i$=Randomly selected index "D" (i=e.g., 1 to 192); $C_i$=Randomly selected index "C" (i=e.g., 1 to 192); $B_i$=Randomly selected index "B" (i=e.g., 1 to 192); $A_i$=Randomly selected index "A" (i=e.g., 1 to 192); S=Illumina® sequencing primer; T=Targeting sequence for gene/amplicon specific capture; CL2=Cleavable linker 2 (to release from captured Ab or protein); X=Capture protein or antibody (for example, protein G for antibodies).

In some embodiments, the origin-specific barcodes are reversibly coupled to a solid or semisolid substrate. In some embodiments, the origin-specific barcodes further comprise a nucleic acid capture sequence that specifically binds to the target nucleic acids and/or a specific binding agent that specifically binds to the target molecules. In specific embodiments, the origin-specific barcodes include two or more populations of origin-specific barcodes, wherein a first population comprises the nucleic acid capture sequence and a second population comprises the specific binding agent that specifically binds to the target molecules. A schematic representation of this is shown in FIG. 3. In some examples, the first population of origin-specific barcodes further comprises a target nucleic acid barcode, wherein the target nucleic acid barcode identifies the population as one that labels nucleic acids. In some examples, the second population of origin-specific barcodes further comprises a target molecule barcode, wherein the target molecule barcode identifies the population as one that labels target molecules.

A nucleic acid barcode may be cleavable from a specific binding agent, for example, after the specific binding agent has bound to a target molecule. In some embodiments, the origin-specific barcode further comprises one or more cleavage sites. In some embodiments at least one cleavage site is oriented such that cleavage at that site releases the origin-specific barcode from a substrate, such as a bead, for example a hydrogel bead, to which it is coupled. In some embodiments at least one cleavage site is oriented such that the cleavage at the site releases the origin-specific barcode from the target molecule specific binding agent. In some embodiments, a cleavage site is a enzymatic cleavage site, such a endonuclease site present in a specific nucleic acid sequence. In other embodiments, a cleavage site is a peptide cleavage site, such that a particular enzyme can cleave the amino acid sequence. In still other embodiments, a cleavage site is site of chemical cleavage.

In some embodiments, each of the origin-specific barcodes comprises one or more indexes, one or more sequences that enable gene specific capture and/or amplification, and/or one or more sequences that enable sequencing library construction.

In some embodiments, the target molecule is attached to an origin-specific barcode receiving adapter, such as a nucleic acid. In some embodiments, the origin-specific barcode receiving adapter comprises an overhang and the origin-specific barcode comprises a sequence capable of hybridizing to the overhang. A barcode receiving adapter is a molecule configured to accept or receive a nucleic acid barcode, such as an origin-specific nucleic acid barcode. For example, a barcode receiving adapter can include a single-stranded nucleic acid sequence (for example, an overhang) capable of hybridizing to a given barcode (for example, an origin-specific barcode), for example, via a sequence complementary to a portion or the entirety of the nucleic acid barcode. In certain embodiments, this portion of the barcode is a standard sequence held constant between individual barcodes. The hybridization couples the barcode receiving adapter to the barcode. In some embodiments, the barcode receiving adapter may be associated with (for example, attached to) a target molecule. As such, the barcode receiving adapter may serve as the means through which an origin-specific barcode is attached to a target molecule. A barcode receiving adapter can be attached to a target molecule according to methods known in the art. For example, a barcode receiving adapter can be attached to a polypeptide target molecule at a cysteine residue (for example, a C-terminal cysteine residue). A barcode receiving adapter can be used to identify a particular condition related to one or more target molecules, such as a cell of origin or a compartment of origin. For example, a target molecule can be a cell surface protein expressed by a cell, which receives a cell-specific barcode receiving adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

In some embodiments, the more than one target molecule specific binding agent is attached to nucleic acid barcodes, such as an origin-specific barcode amongst others, having the same sequence. In certain embodiments, the more than one target molecule specific binding agent is attached to nucleic acid barcodes having distinct sequences. In some instances, a plurality of target molecule specific binding agent can be added to a compartment. Alternatively, a plurality of target molecule specific binding agent can be added separately. Each different target molecule specific binding agent can optionally be, for example, associated with an experimental condition.

One of the superior properties of the disclosed methods is the samples, such as the contents of multiple compartments, can be analyzed together in a single reaction, for example a pooled reaction. Thus, in some examples, the individual compartments are pooled to create a pooled sample. The target molecules and/or target nucleic acids from a plurality of compartments, labeled according to the disclosed methods, can be combined to form a pool. For example, labeled target molecules and/or target nucleic acids in a plurality of emulsion droplets can be combined by breaking the emulsion. Thus, in some embodiments, the emulsion is broken. The pools can be comprised of labeled target molecules and/or target nucleic acids coming from a large number of individual compartments or discrete volumes (for example, at least 2, 3, 4, 5, 6, 7, 8, 9, 10, 20, 30, 40, 50, 100, 500, 1,000, 2,500, 5,000, 10,000, 50,000, 100,000, 500,000, 1,000,000, 2,000,000, or more; in various examples, for example, those utilizing plates, the numbers can be, for example, at least 6, 24, 96, 192, 384, 1,536, 3,456, or 9,600), thus facilitating processing of very large numbers of samples at the same time (for example, by highly multiplexed affinity measurement), leading to great efficiencies.

Labeled target molecules and/or target nucleic acids can be isolated or separated from a pool. Exemplary isolation techniques include, without limitation, affinity capture, immunoprecipitation, chromatography (for example, size exclusion chromatography, hydrophobic interaction chromatography, reverse-phase chromatography, ion exchange chromatography, affinity chromatography, metal binding chromatography, immunoaffinity chromatography, high performance liquid chromatography (HPLC), and liquid chromatography-mass spectrometry (LC-MS)), electrophoresis, hybridization to a capture oligonucleotide, phenol-chloroform extraction, minicolumn purification, or ethanol or isopropanol precipitation. Chromatography methods are described in detail, for example, in Hedhammar et al. ("Chromatographic methods for protein purification," Royal Institute of Technology, Stockholm, Sweden), which is incorporated herein by reference. Such techniques can utilize a capture molecule that recognizes the labeled target molecule or a barcode or binding moiety associated with the target molecule. For example, a target antibody can be isolated by affinity capture using protein G. Labeled target molecules can be further labeled with capture labels, such as biotin. A plurality of target molecules (for example, a plurality of identical target molecules, or a population of target molecules including multiple distinct target molecules) can be isolated simultaneously or separately.

In some embodiments, an origin-specific barcode further includes a capture moiety, covalently or non-covalently linked. Thus, in some embodiments the origin-specific barcode, and anything bound or attached thereto, that include a capture moiety are captured with a specific binding agent that specifically binds the capture moiety. In some embodiments, the capture moiety is adsorbed or otherwise captured on a surface. In specific embodiments, a targeting probe is labeled with biotin, for instance by incorporation of biotin-16-UTP during in vitro transcription, allowing later capture by streptavidin. Other means for labeling, capturing, and detecting an origin-specific barcode include: incorporation of aminoallyl-labeled nucleotides, incorporation of sulfhydryl-labeled nucleotides, incorporation of allyl- or azide-containing nucleotides, and many other methods described in Bioconjugate Techniques ($2^{nd}$ Ed), Greg T. Hermanson, Elsevier (2008), which is specifically incorporated herein by reference. In some embodiments, the targeting probes are covalently coupled to a solid support or other capture device prior to contacting the sample, using methods such as incorporation of aminoallyl-labeled nucleotides followed by 1-Ethyl-3-(3-dimethylaminopropyl)carbodiimide (EDC) coupling to a carboxy-activated solid support, or other methods described in Bioconjugate Techniques. In some embodiments the specific binding agent is has been immobilized for example on a solid support, thereby isolating the origin-specific barcode.

By "solid or semisolid support or carrier" is intended any support capable of binding an origin-specific barcode. Well-known supports or carriers include hydrogels, glass, polystyrene, polypropylene, polyethylene, dextran, nylon, amylases, natural and modified celluloses, polyacrylamides, agarose, gabbros and magnetite. The nature of the carrier can be either soluble to some extent or insoluble for the purposes of the present disclosure. The support material may have virtually any possible structural configuration so long as the coupled molecule is capable of binding to targeting probe. Thus, the support configuration may be spherical, as in a bead, or cylindrical, as in the inside surface of a test tube, or the external surface of a rod. Alternatively, the surface may be flat such as a sheet or test strip. Thus, some embodiments of the method include selectively isolating the origin-labeled molecules and origin-labeled nucleic acids, for example from a pooled sample. In some embodiment, the cells are lysed.

Target molecules include any molecule present in a sample or subsample, such as an individual or set of compartment, about which information is desired, such as expression, activity, and the like. In certain embodiments, a target molecule that can be labeled and characterized according to the disclosed methods include polypeptides (such as but not limited to proteins, antibodies, antigens, immunogens, protein complexes, and peptides), which are in some cases modified, such as post-translationally modified, for example glycosylated, acetylated, amidated, formylated, gamma-carboxyglutamic acid hydroxylated, methylated, phosphorylated, sulfated, or modified with pyrrolidone carboxylic acid. The methods disclosed herein are particularly useful in screening libraries of antibodies. In specific embodiments, target molecules are antibodies, such as a set of antibodies being screened for activity, for example specificity and/or affinity. In some embodiments, an antibody is an anti-HIV antibody, such as an anti-gp41 or gp120 antibody. The methods disclosed herein are also particularly useful in screening libraries of potential antigens or immunogens, for example to determine their potential efficacy in eliciting an antibody response to a particular pathogen, for example a neutralizing antibody response. In specific embodiments, target molecules are antigens or immunogens, such as a set of antigens or immunogens being screened for activity, for example specificity and/or affinity. In some embodiments, antigens or immunogens are HIV antigens or immunogens, such as a gp41 or gp120 antigens or immunogens, for example an immunogenic fragment of gp41 and/or gp120. Target molecules also include, nucleic acids (such as DNA and RNA, for example mRNA and cDNA), carbohydrates, lipids, small molecules, such as a potential or realized therapeutic, compounds, and inorganic compounds, as well as conjugates and complexes of the exemplary target molecule types described herein. Target molecules can be natural, recombinant, or synthetic. As disclosed herein a given compartment can include one or more distinct target molecules, meaning that several targets can be present in the compartment. In some instances, a compartment can include a target polypeptide molecule and a target nucleic acid molecule encoding the target polypeptide molecule, such that the nucleic acid sequence encoding the target polypeptide can be readily determined. Thus, in certain instances, a polypeptide target molecule and a nucleic acid target molecule are produced by the same cell. In particular instances, the polypeptide target molecule and the target nucleic acid are labeled with the same origin-specific barcodes or matching barcodes. In some examples, the target molecule is not encoded by a target nucleic acid. Target molecules can be expressed in cells or in extracts, such as cell free extracts. In some embodiments, the target molecule comprises a polypeptide, nucleic acid, polysaccharide, and/or small molecule. In specific embodiments, the polypeptide comprises an antibody, an antigen, or a fragment thereof. In specific examples, the target molecules represent a library of randomly mutated polypeptides. In specific embodiments, the target molecule is expressed on the surface of a cell, such as a cell surface protein, or a fragment thereof, such as a cell surface domain of a protein.

In some examples, the target molecules, optionally in association and the target nucleic acids, are produced by the individual cells in the compartments. This, in some examples, the target molecules are polypeptides and the target nucleic acids encode the target molecules in their respective individual compartments. In some examples, the cells are B-cells and the target molecules are antibodies and the target nucleic acids encode the antibodies. In some embodiments, a target molecule is present on the surface of a cell. Thus, in some embodiments, a target molecule, such as a protein or polypeptide, is one that is normally found on the surface of a cell. In other embodiments, a target molecule, such as a protein or polypeptide, is not normally found on the surface of a cell, but is expressed on the surface of a cell, such as by recombinant means. In certain instances, a target molecule is normally found within a cell, such as in the cytoplasm or in an organelle. In these examples, it may be necessary to lyse a cell in which the target molecule is produced in order to label it. Protein or nucleic acid target molecules can be naturally produced by a cell or can be recombinantly produced based on, for example, the presence of a synthetic construct in a cell.

In some embodiments, a target molecule is a protein or peptide found in a protein or peptide database (for example, SWISS-PROT, TrEMBL, SBASE, PFAM, or others known in the art), or a fragment or variant thereof. A target molecule may be a protein or peptide that may be derived (for example, by transcription and/or translation) from a nucleic acid sequence known in the art, such as a nucleic acid sequence found in a nucleic acid database (for example, GenBank, TIGR, or others known in the art), or a fragment or variant thereof.

Target molecules such as polypeptides can optionally be produced by one or more synthetic multi-gene genetic constructs, which can be present in compartments as described herein in a cell or with a cell-free extract. Such target molecules can include, for example, variants of an antibody sequence (for example, CDR sequences) and/or various combinations of antibody light and heavy chains.

A target molecule may be a protein or polypeptide endogenous to an organism, such as a protein or polypeptide selectively expressed or displayed by one or more cells of an organism. For example, the protein or polypeptide may be a cell surface marker expressed by the one or more cells. The organism may be, for example, a eukaryote (for example, a mammal, such as a human), virus, bacterium, or fungus. In some embodiments, a plurality of distinct target molecules is selected from a single organism. In alternate embodiments, a plurality of distinct target molecules is selected from among a plurality of distinct organisms.

In some embodiments of the disclosed method, the cells are fixed. Methods of fixing cells are well known in the art and include for example fixation with an aldehyde. In some embodiments, the cells are not fixed.

In various embodiments, a target molecule is displayed or expressed on the surface of a cell. Thus, in the case of proteins, the target molecule can be, for example, an antibody, cell surface receptor, signaling protein, transport protein, cell adhesion protein, enzyme, or a fragment thereof. Cell surface target molecules include known transmembrane proteins, i.e., a protein known to have one or more transmembrane domains, a protein previously identified as associating with the cellular membrane, or a protein predicted to have one or more transmembrane domains by one or more methods of domain prediction known in the art. The cell surface target molecule may alternatively be a fragment of such a protein. A cell surface target molecule can be an integral membrane protein or a peripheral membrane protein, and/or can be a protein or polypeptide having a sequence present in nature, substantially similar to a sequence present in nature, engineered or otherwise modified from a sequence present in nature, or artificially generated, for example, by techniques of molecular biology (for example, fusion proteins).

A target molecule may also be a nucleic acid, such as a DNA or RNA molecule. For example, an RNA molecule transcribed from a gene of interest (or a corresponding cDNA molecule) can be labeled according to the methods of the disclosure and subsequently isolated and sequenced with its barcode label. A plurality of such labeled nucleic acids can be simultaneously labeled, for example, with each nucleic acid receiving a distinct barcode and/or one or more unique molecular identifiers and barcode receiving adapters. In certain embodiments, the nucleic acid is produced by a cell, cell lysate, or cell-free extract. In particular embodiments, the nucleic acid is produced by a microbe, such as a prokaryotic cell. In some embodiments, a nucleic acid target molecule encodes a polypeptide target molecule in the same compartment.

In some embodiments, a target molecule may be associated with diseased cells or a disease state. For instance, a target molecule may be associated with cancer cells, for example, a protein, polypeptide, or nucleic acid selectively expressed or not expressed by cancer cells, or may specifically bind to such a protein or polypeptide (for example, an antibody or fragment thereof, for example, as described herein). In certain instances, the target molecule is a tumor marker, for example, a substance produced by a tumor or produced by a non-cancer cell (for example, a stromal cell) in response to the presence of a tumor. Many tumor markers are not exclusively expressed by cancer cells, but may be expressed at altered (i.e., elevated or decreased) levels in cancerous cells or expressed at altered (i.e., elevated or decreased) levels in non-cancer cells in response to the presence of a tumor. In some embodiments, the target molecule may be a protein, polypeptide, or nucleic acid expressed in connection with any disease or condition known in the art.

In some embodiments, the sample comprises one or more synthetic genetic constructs comprising one or more polypeptide coding sequence connected to a promoter, such a set of synthetic genetic constructs, which optionally are comprised of combinatorially generated parts.

The compartments, such as discrete volumes or spaces, as disclosed herein mean any sort of area or volume which can be defined as one where the barcoded molecules, such as labeled target molecules or labeled nucleic acids are not free to escape or move between. Compartments include droplets, such as the droplets from a water-in-oil emulsion, or as deposited on a surface, such as a microfluidic droplet, for example deposited on a slide. Other types of compartments include without limitation a tube, well, plate, pipette, pipette tip, and bottle. Other types of compartments include "virtual" containers, such as defined by areas exposed to light, diffusion limits, or electro-magnetic means. Such compartments can also exist by diffusion defined volumes, or spaces that are only accessible to certain molecules or reactions because diffusion constraints effectively defining a space, for example, chemically defined volumes or spaces where only certain target molecules can exist because of their chemical or molecular properties such as size, or electro-magnetically defined volumes or spaces where the electro-magnetic properties of the target molecules or their supports such as charge or magnetic properties can be used to define certain regions in a space. Such discrete may also be optically defined volumes or spaces that may be defined by illuminating it with visible, ultraviolet, infrared, or other wavelengths of light such that only target molecules within the defined space may be labeled. Such compartments can be composed of, for example, plastic, metal, composite materials, and/or glass. Such compartments can be adapted for placement into a centrifuge (for example, a microcentrifuge, an ultracentrifuge, a benchtop centrifuge, a refrigerated centrifuge, or a clinical centrifuge). A discreet volume can exist on its own, as a separate entity, or be part of an array of such discreet volumes, for example, in the form of a strip, a microwell plate, or a microtiter plate. A compartment can have a capacity of, for example, at least about 1 femtoliter (fl) to about 1000 ml, such as about 1 fl, 10 fl, 100 fl, 250 fl, 500 fl, 750 fl, 1 picoliter (pl), 10 pl, 100 pl, 250 pl, 500 pl, 750 pl, 1 nl, 10 nl, 100 nl, 250 nl, 500 nl, 750 nl, 1 µl, 5 µl, 10 µl, 20 µl, 25 µl, 50 µl, 100 µl, 200 µl, 250 µl, 500 µl, 750 µl, 1 ml, 1.25 ml, 1.5 ml, 2 ml, 2.5 ml, 5 ml, 10 ml, 15 ml, 20 ml, 25 ml, 50 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 900 ml, or 1000 ml.

In certain embodiments, a compartment is a droplet, such as a droplet in an emulsion and/or a microfluidic droplet.

Emulsification can be used in the methods of the disclosure to separate or segregate a sample or set of samples into a series of compartments, for example a compartment having a singe cell or a discrete portion of an acellular sample, such as a cell-free extract or a cell-free transcription and/or cell-free translation mixture. Typically, as used in conjunction with the methods and compositions disclosed herein, an emulsion will include a plurality of droplets, each droplet including one or more target molecules and/or target nucleic acids and an origin-specific barcode, such that each droplet includes a unique barcode that distinguishes it from the other droplets. Emulsification can be used in the methods of the disclosure to compartmentalize one or more target molecules in emulsion droplets with one or more nucleic acid barcodes, such as origin specific barcodes. An emulsion, as disclosed herein, will typically include a plurality of droplets, each droplet including one or more target molecules, target nucleic acids and one or more nucleic acid barcodes, such as origin specific barcodes. Droplets in an emulsion can be sorted and/or isolated according to methods well known in the art. For example, double emulsion droplets containing a fluorescence signal can be analyzed and/or sorted using conventional fluorescence-activated cell sorting (FACS) machines at rates of >$10^4$ droplets $s^{-1}$, and have been used to improve the activity of enzymes produced by single cells or by in vitro translation of single genes (Aharoni et al., *Chem Biol* 12(12):1281-1289, 2005; Mastrobattista et al., *Chem Biol* 2(12):1291-1300, 2005). However, the emulsions are highly polydisperse, limiting quantitative analysis, and it is difficult to add new reagents to pre-formed droplets (Griffiths et al., *Trends Biotechnol* 24(9):395-402, 2006). These limitations can, however, be overcome by using protocols based on droplet-based microfluidic systems (see for example Teh et al., *Lab on a chip* 8(2):198-220, 2008; Theberge et al., *Angew Chem Int Ed Engl* 49(34):5846-5868, 2010; and Guo et al., *Lab on a chip* 12(12):2146, 2012) in which highly monodisperse droplets of picoliter volume can be made (Anna et al., *Appl Phys Lett* 82(3):364-366, 2003), fused (Song et al., *Angew Chem Int Edit* 42(7):767-772, 2003; Chabert et al., *Electrophoresis* 26(19):3706-3715, 2005), split (Song et al., *Angew Chem Int Edit* 42(7):767-772, 2003; Link et al., *Phys Rev Lett* 92(5):054503, 2004), incubated (Song et al., *Angew Chem Int Edit* 42(7):767-772, 2003; Frenz et al., *Lab on a chip* 9(10):1344-1348, 2009), and sorted triggered on fluorescence (Baret, et al., *Lab on a chip* 9(13):1850-1858, 2009), at kHz frequencies, such as those described in Mazutis et al. (*Nat. Protoc.* 8(5): 870-891, 2013), incorporated by reference herein. As disclosed herein, an emulsion can include various compounds, enzymes, or reagents in addition to the target molecules, target nucleic acids and origin-specific barcodes. These additives may be included in the emulsion solution prior to emulsification. Alternatively, the additives may be added to individual droplets after emulsification.

Emulsion may be achieved by a variety of methods known in the art (see, for example, US 2006/0078888 A1, of which paragraphs [0139]-[0143] are incorporated by reference herein). In some embodiments, the emulsion is stable to a denaturing temperature, for example, to 95° C. or higher. An exemplary emulsion is a water-in-oil emulsion. In some embodiments, the continuous phase of the emulsion includes a fluorinated oil. An emulsion can contain a surfactant or emulsifier (for example, a detergent, anionic surfactant, cationic surfactant, or amphoteric surfactant) to stabilize the emulsion. Other oil/surfactant mixtures, for example, silicone oils, may also be utilized in particular embodiments. An emulsion can be contained in a well or a plurality of wells, such as a plate, for easy of handling. In some examples, one or more target molecules, target nucleic acid and nucleic acid barcodes are compartmentalized. An emulsion can be a monodisperse emulsion or a polydisperse emulsion. Each droplet in the emulsion may contain, or contain on average, 0-1,000 or more target molecules. For instances, a given emulsion droplet may contain 0, 10, 20, 30, 40, 50, 100, 200, 300, 400, 500 or more target molecules. In particular embodiments, a given droplet may contain 0, 1, 2, or 3 cells capable of expressing or secreting target molecules, for example, a clonal population of target molecules. On average, the droplets of an emulsion of the present in disclosure may contain 0-3 cells capable of expressing or secreting target molecules, such as 0, 1, 2, or 3 cells capable of expressing or secreting target molecules, as rounded to the nearest whole number. In some embodiments, the number of cells capable of expressing or secreting target molecules in each emulsion droplet, on average, will be 1, between 0 and 1, or between 1 and 2. In other embodiments, the droplet may contain an acellular system, such as a cell-free extract.

Compartmentalization of target molecules, target nucleic acids and nucleic acid barcodes into wells can be achieved, in some embodiments, due to physical limitations relating to the mass or dimensions of the target molecules and nucleic acid barcodes, the dimensions of the well, or a combination thereof. A well may be a fiber-optic faceplate where the central core is etched with an acid, such as an acid to which the core-cladding is resistant. A well may be a molded well. The wells may be covered to prevent communication between the wells, such that the beads present in a particular well remain within the well or are inhibited from moving into a different well. The cover may be a solid sheet or physical barrier, such as a neoprene gasket, or a liquid barrier, such as fluorinated oil. Methods applicable to the present disclosure are known in the art (for example, Shukla et al., J. Drug Targeting 13: 7-18, 2005; Koster et al., Lab on a Chip 8: 1110-1115, 2008).

In certain embodiments, the single cells or a portion of the acellular system from the sample are encapsulated together with a bead, such as a hydrogel bead that includes the origin-specific barcodes reversibly coupled thereto. As schematic diagram depicting such encapsulation is shown as FIG. 1. With reference to FIG. 1, a set of hydrogel beads, such as PEG-DA beads, of uniform size is created, for example, using a PDMS chip. In some embodiments, the uniformly sized PEG-DA hydrogel bead are co-polymerized with a generic capture oligonucleotide, which can be used to build a nucleic acid identification sequence unique to each bead. Using automation techniques and split-pool labeling (see for example International Patent Publication No. WO2014/047561, which is specifically incorporated by reference) a unique nucleic acid barcode can be added to each bead. Using microfluidics, the individual beads can be placed into single drop and then single cells added, such that each drop in the emulsion contains a single cell and single hydrogel containing a unique origin-specific bar code. As shown in the FIG. 1, this system can be used to label all of the amplicons derived from a cell with a unique barcode. If the emulsion is then broken, the result is a pooled sample of amplicons barcoded according to droplet. This all of the amplicons can be traced back to the single cell from which they originated. As exemplified in FIG. 2, in some embodiments, a bead includes an exemplary bead and origin-specific barcode for labeling a target nucleic acid. In specific embodiments, the origin-specific barcodes are delivered to the compartments by delivering a single bead to each compartment wherein each bead carries multiple copies of a single origin-specific barcode sequence.

In some embodiments, of the method, the cells are contacted with one or more test agents, such as a small molecule, a nucleic acid, a polypeptide, or a polysaccharide. In specific examples, the polypeptide comprises an antibody or an antibody fragment. In some embodiments the test agent is also labeled with the origin-specific barcode. In some embodiments, the individual test agents are labeled with a test-agent specific barcodes.

In some embodiments, the methods further include amplifying one or more of the origin-specific barcodes, the target molecule specific binding agent barcodes, test-agent specific barcodes, the target nucleic acid barcodes, and the target molecule barcodes.

In some embodiments, the methods further include detecting one or more of the target molecule specific binding agent barcodes, test-agent specific barcodes, the target nucleic acid barcodes, and the target molecule barcodes, for example detecting the sequence of the origin-specific barcodes, the target molecule specific binding agent barcodes, test-agent specific barcodes, the target nucleic acid barcodes, and/or the target molecule barcodes with hybridization, sequencing, or a combination thereof.

In some embodiments, the methods further include quantifying or more of the origin-specific barcodes, the target molecule specific binding agent barcodes, test-agent specific barcodes, the target nucleic acid barcodes, and the target molecule barcodes.

Aspect of this disclosure concern methods for determining the specificity and/or affinity of a test agent for one or more target molecules. The disclosed methods include contacting the cells expressing target molecules, prior to segregation, with a pool of test agents labeled with a test agent specific barcode. The target molecules bound to the test agents are isolated, and the sequence of the test agent specific barcodes and the sequence of the origin specific barcode is determined, thereby identifying the test agents bound to the target molecules. In some embodiments, the target molecule comprises a cell surface protein and the target nucleic acid encodes the cell surface protein. In some examples of the method, unbound test agents are washed from the cells. In some embodiment, a target nucleic acid is a cDNA or mRNA. Some embodiments of the method, further include labeling the test agents with the origin-specific barcode.

Examples of test agents include small molecule compounds, nucleic acids, polypeptides (such as proteins, antibodies, antigens, and/or immunogens), or a polysaccharide. In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Appropriate agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

The compounds identified using the methods disclosed herein can serve as conventional "lead compounds" or can themselves be used as potential or actual therapeutics. In some instances, pools of candidate agents can be identified and further screened to determine which individual or sub-pools of agents in the collective have a desired activity.

In other embodiments, determining a target molecules affinity and/or specificity for a test agent includes: contacting the labeled target molecules with a test agent bound with a detectable label; isolating the labeled target molecules bound to the test agent using the detectable label; determining the sequence of origin-specific barcode on the isolated target molecules; and quantifying the origin-specific barcodes associated with the isolated target molecules, thereby determining the affinity of the test agent for the target molecules. In some examples, the origin-specific barcodes that are not isolated with the test agent are quantified to normalize concentration. In some embodiments, the origin-specific barcodes are cleaved after isolation. In some embodiment the isolated barcodes are associated with the target nucleic acids to determine the sequence of the target molecules bound to the test agent. In some examples the target molecules comprise polypeptides, such as antibodies, antigens and/or immunogens. In specific examples, the antibodies comprise anti-HIV antibodies, such as anti-gp41 or anti-gp120 antibodies and the test agents comprise a set of potential HIV immunogens. In specific examples, the test agent comprises an antibody, and the target molecules comprise proteins expressed on the surface of the cell, for example the test agent comprises an anti-HIV antibody, such as an anti-gp41 or gp120 antibody and the target molecules comprise a set of HIV immunogens. In some embodiments, the methods include determining one or more of the dissociation constant, on-rate, or off-rate of the target molecule for the test agent.

Aspects of the disclosed methods also concern determining the expression of target molecules on the surface of a cell or set of cells. The methods include: assigning a set of target molecules to target nucleic acids in a sample or set of samples; contacting the sample cells to be segregated with a set of test agents each labeled with a unique test agent barcode; determining the sequence of origin-specific barcode, thereby determining the expression of molecules on the surface of the set of cells. Some examples include associating the isolated barcodes with the target nucleic acids to determine the sequence of the target molecules bound to the test agent. In specific embodiments, the target molecules comprises polypeptides, such as antibodies, specific for cell surface markers. In some embodiments, the molecules expressed on the surface of the cells are associated with the cell type, cell cycle or other measure of cellular state.

Aspects of this disclosure further concern, a method of identifying a protein having a specific activity of interest from a population of cells. The method including: assigning a set of target molecules to target nucleic acids in a sample or set of samples; isolating the target molecules having the specific activity of interest; and identifying the origin-specific barcodes of the isolated target molecules having the specific activity interest. In some embodiments the method further includes identifying the target nucleic acid molecules encoding the proteins by matching of sequences of origin-specific nucleic acid barcodes. In some examples, the activity is antigen binding and proteins are antibodies. In some embodiments, an antibody of interest is made by expression of a nucleic acid molecule identified as encoding an antibody of interest.

Aspects of the present disclosure concern methods for determining the levels of post translationally modified target molecules, such as target proteins, in a cell or samples of cells, such as individual cells. The determination of any post-translational modification is possible, for example, for example glycosylated, acetylated, amidated, formylated, gamma-carboxyglutamic acid hydroxylated, methylated, phosphorylated, sulfated, or modified with pyrrolidone carboxylic acid. In the disclosed methods, a sample, such as a sample of cells of interest is contacted with a first specific binding agent that specifically binds the post-translationally modified target molecule at the site of modification and a second specific binding agent that specifically binds non-post-translationally modified target molecule at the site of modification, wherein the first and second specific binding are labeled with a specific binding agent specific barcode. Single cells are segregated into individual compartments, wherein each individual compartment further comprises an origin-specific barcode, comprising a unique nucleic acid identification sequence that maintains or carries information about the compartment of origin of the segregated cell in the sample. In some examples, the cells are lysed to release the contents of the cells such that the specific biding agents can interact and thus bind the target molecules in the compartments. The first specific binding agent and the second specific binding agent in the individual compartments are labeled with the origin-specific barcodes present in the individual compartments and the target molecules are isolated, thereby isolating the first and second specific binding agents bound to the target molecules. The sequences of the origin-specific barcode and the specific binding agent barcode present on the isolated specific binding agents, thereby determining the presence of the post translationally modified protein in the sample. In some embodiments, the method includes quantitating the levels of post-translationally modified and unmodified target proteins, for example to determine the ratio of modified to non-modified target molecules. In some examples the isolation comprises contacting the target molecule with a third specific binding agent that does not bind the site of modification, wherein the third specific binding agent is detectably labeled. In some embodiments, the method further includes labeling target nucleic acids in the individual compartments with the origin-specific barcodes present in the individual compartments to create origin-labeled target nucleic acids, wherein the origin-labeled target nucleic acids from each individual compartment comprise the same or matched, unique indexing nucleic acid identification sequence as the origin-labeled target molecules and then detecting the nucleotide sequence of the origin-specific barcodes, thereby assigning the set of target proteins to target nucleic acids in the sample or set of samples while maintaining information about the compartment of origin of the target proteins and the target nucleic acids.

C. Exemplary Applications

1. Genotype-Phenotype Coupling

The disclosure provides methods for co-detecting expressed target molecules (for example, a polypeptide, protein, protein complex, or any other gene product) and nucleic acids (for example, RNA or DNA) encoding the expressed target molecules. In certain embodiments, each of a plurality of discreet volumes contains one or more cells that are allowed to express a target polypeptide molecule. After expression and optional cell lysis, the expressed polypeptide is labeled with an origin-specific nucleic acid barcode by maintaining the discreet volume under conditions permitting the barcode labeling to proceed. Nucleic acid molecules (for example, RNA or cDNA reverse transcribed therefrom) encoding the target polypeptide molecule are also labeled with an origin-specific nucleic acid barcode.

The origin-specific nucleic acid barcodes used to label a target polypeptide molecule and a corresponding nucleic acid molecule within a particular discreet volume are typically matched nucleic acid barcodes. Matched nucleic acid barcodes can be, for example, at least 80% identical (for example, 80%, 85%, 90%, 95%, 99%, or 100% identical). In certain embodiments, the matched nucleic acid barcodes are 100% identical. In other embodiments, the matched barcodes may have different sequences but can be identified as members of a matched pair based on their sequences (for example, by specifying in advance that two particular barcodes are introduced into the same container, such that molecules tagged with the two particular barcodes must have originated from the same container). Origin-specific nucleic acid barcodes can optionally be introduced into a discreet volume bound to a single solid or semisolid support, such as a bead as disclosed herein. In such instances, origin-specific nucleic acid barcodes intended for binding to the target polypeptide molecule can be comprised within a tagging element that includes an affinity moiety (for example, an antibody) specific for the target polypeptide molecule, while origin-specific nucleic acid barcodes intended for binding to the corresponding nucleic acid molecule can be comprised within a tagging element that includes an affinity moiety (for example, a nucleic acid molecule) specific for the corresponding nucleic acid molecule.

After labeling with origin-specific nucleic acid barcodes, target polypeptide molecules and/or corresponding nucleic acids can be combined to form a pool, and associated barcodes (and, optionally, target nucleic acid molecules) amplified. The discreet volume of origin for a given target polypeptide molecule or nucleic acid in the pool can be determined by identifying the sequence of the associated origin-specific nucleic acid barcode.

In certain variations of these methods, prior to identifying the sequence, particular portions of the pool can optionally be isolated. For example, in the case of the target polypeptide molecule being an antibody or a fragment thereof, chromatography on a column including immobilized antigen to which the antibody binds can be carried out, optionally under particular or varying conditions of stringency to permit the isolation of, for example, antibodies having particularly high binding affinity. In another example, in the case of a target polypeptide molecule being an antigen comprising an antigen or immunogen, the chromatography can be carried out using a column including immobilized antibody (or an antigen-binding fragment thereof). In other examples, an activity or property other than binding affinity can be assessed. In any case, particular target polypeptide molecules with desirable features can be isolated and the identities or other features (for example, activities and/or affinities) of the target polypeptide molecules can be determined by sequencing of the origin-specific nucleic acid barcodes. The genotypes corresponding to the phenotypes of selected target polypeptide molecules can be determined by use of sequencing to identify matched origin-specific nucleic acid barcodes in pooled nucleic acid samples, and then optionally sequencing the nucleic acids attached to these barcodes.

In other variations of these methods, the isolation step described above is not required. Rather, peptides or polypeptides including epitopes of interest are labeled with epitope-specific nucleic acid barcodes. These peptides or polypeptides are mixed with cells expressing antibodies on their surfaces (for example, B cells, such as B cells obtained by in vitro immunization or from an immunized donor, hybridomas, or other cells expressing recombinant antibodies), to which they bind. Unbound peptides or polypeptides are washed from the cells, which are then isolated in discreet volumes (for example, 1 cell/discreet volume). Origin-specific nucleic barcodes then can label antibodies produced by the cells, nucleic acids encoding the antibodies, and the peptides or polypeptides (or the epitope-specific nucleic acid barcodes). Multiplex sequencing of labeled molecules pooled from multiple discreet volumes can be used to connect cells producing antibodies that bind particular epitopes with corresponding coding sequences.

Also included are methods of making antibodies using nucleic acid molecules identified by the methods of the disclosure as encoding antibodies of interest. In these methods, the identified nucleic acid molecules are expressed in cells, using standard methods in the art.

2. Proteomics

The methods disclosed herein can be used in proteomics applications in order to, for example, assess expression levels and/or functions of various proteins expressed in cells or in cell-free systems. The proteins can optionally be encoded by synthetic constructs (for example, multi-gene constructs). In various examples, the proteins are components of a metabolic pathway, and the proteomic analysis can be carried out, for example, to assemble and optimize novel pathways and/or to identify rate limiting steps. With respect to the latter, based on the results of the analysis, expression of a rate limiting component of a pathway can be altered in order to optimize the pathway. These approaches can be used, for example, in the context of optimizing metabolically engineered microorganisms in synthetic biology.

In other applications, the proteomics methods disclosed herein can be used in the identification and verification of biomarkers for disease, such as cancer, and optionally can be used to assess proteome changes in cells exposed to different conditions. The different proteins analyzed using the methods of the disclosure can be different components of a pathway and/or sequence variants of a base sequence, in which case the methods can be used to identify variants having particular expression levels, stabilities, or other functional features. The variations assessed can range from individual amino acid substitutions to domain or subunit substitutions or swaps, and can include any number of combinations thereof. The variations can be random or can be generated by, for example, mixing and matching of sequences derived from, for example, different species.

3. Cell Surface Marker Analysis

The disclosure provides methods of massively multiplexing the identification and/or quantification of cell surface markers (for example, cell surface proteins) by nucleic acid barcoding. The target molecule can be a cell surface marker associated with a barcode receiving adapter. For example, a cell surface marker can be attached to an oligonucleotide barcode receiving adapter that includes an overhang capable of accepting a portion of a barcode. The barcode can, for example, include a corresponding overhang capable of hybridizing to the overhang on the barcode receiving adapter. Thus, a plurality of cell surface markers can be tagged with barcodes. The barcode receiving adapter can also function as a further identifier. For example, a cell in a discreet volume can express cell surface markers which are then associated with barcode receiving adapters. One or more barcodes can then be attached to each barcode receiving adapter. For example, all barcode receiving adapters in a discreet volume and/or associated with cell surface markers expressed by a particular cell can receive identical barcodes. In certain embodiments, each barcode receiving adapter is distinct to the individual cell surface marker. In alternate embodiments, the cell surface markers expressed by a particular cell all receive identical barcode receiving adapters.

A cell surface marker and a nucleic acid encoding the cell surface marker (for example, an mRNA) can be associated with identical barcode receiving adapters and/or barcodes, for example, according to the genotype-phenotype coupling methods described herein. In certain embodiments, a cell that does not express a particular cell surface marker can be identified if one or more barcodes are detected in association with the cell without also detecting the mRNA corresponding to the cell surface marker.

In an example of a cell surface marker-related application, a plurality of cells (for example, B cells), each expressing a distinct cell surface specific binding agent (for example, a cell surface protein, such as an antibody), is mixed with a plurality of target epitopes (for example, epitopes for HIV proteins, such as Gag, Pol, Env, or Nef, gp120, gp41) labeled with oligonucleotide barcodes that, for example, identify each unique type of epitope. Optionally, a unique molecular identifier is associated with, for example, each epitope-specific nucleic barcode. Thus, each epitope-specific nucleic acid barcode for HIV epitope #1, for example, would be associated with a different unique molecular identifier, for quantification. The oligonucleotide barcodes may further include, for example, a unique molecular identifier. Binding of the target epitopes to the cell surface binding moieties can be allowed to occur, followed by washing away of excess epitopes. Each cell, together with its expressed cell surface binding moieties and bound epitopes, can then be encapsulated in a discreet volume (for example, an emulsion droplet). The cells can, for example, be lysed in the discreet volumes to release their internal contents. The discreet volumes can further include origin-specific barcodes that can be used to label the cell surface binding moieties and/or target epitopes. As such, the cell surface binding moieties and/or target epitopes can be target molecules of the disclosure. In some instances, the origin-specific barcodes can also label, for example, nucleic acids encoding the cell surface binding moieties (for example, mRNA or cDNA molecules encoding the cell surface binding moieties, such as RNA encoding heavy and/or light chains of antibodies produced by the B cell), thereby labeling the cell surface binding moieties and the nucleic acids encoding the cell surface binding moieties with the same barcodes. In certain instances, the target epitopes are further labeled with the same origin-specific barcode (for example, by ligating the origin-specific barcode to the oligonucleotide barcode already labeling the epitope). In some instances, the cell surface binding moieties, target epitopes, and/or nucleic acids encoding the cell surface binding moieties are labeled with the same or distinct barcodes (for example, barcodes that are predetermined as associated with each other, for example, by attachment to the same support). The barcodes labeling the cell surface binding moieties, target epitopes, and/or the nucleic acids encoding the cell surface binding moieties can be pooled, separated, amplified, and/or sequenced according to the methods of the present disclosure. By sequencing the origin-specific nucleic acid barcodes, as well as the epitope-specific nucleic acid barcodes, antibodies that bind to each particular epitope of interest can be identified. Furthermore, sequencing RNAs associated with origin-specific nucleic acid barcodes enables the identification of antibody nucleic acid sequences that can be used to make and/or further characterize antibodies of interest.

4. Affinity Analysis

The methods of the disclosure can be used to determine the binding affinity between a target molecule and another molecule (for example, a specific binding agent). For example, an equilibrium constant (Kd) and an off-rate ($k_{off}$) for the binding interaction between a target molecule and another molecule (for example, a specific binding agent) can be measured using methods known in the art. For example, if a specific binding agent is attached to a solid support (for example, a column, chip, surface, or bead), Kd can be measured by titrating in various amounts of the target that is conjugated to a barcode. After incubating, the solid support can be washed, and the barcode can be cleaved and sequenced to determine the quantity of target that is bound to the specific binding agent. This assay could be performed in reverse with the target molecule bound to the solid support and the specific binding agent conjugated to the barcode. An alternate method involves a "sandwich" format for bulk affinity purification or analysis, in which the target molecule is complexed with a specific binding agent (for example, a specific binding agent labeled with a barcode, such as an origin-specific barcode) and also complexed with another specific binding agent that is bound to a solid support. In this method, the target molecule may not be directly attached to an origin-specific barcode, but is rather labeled by binding to the specific binding agent labeled with the origin-specific barcode.

These assays can also be performed in a competitive format by adding a molecule that will compete with the target molecule for binding to the specific binding agent. The competitor can be added simultaneously with the target molecule, or after the addition and subsequent complexation of the target molecule to the specific binding agent. The competitor can optionally be conjugated to a barcode. For example, the competitor can be a target molecule, for example, a target molecule labeled with an origin-specific barcode. In some instances, $k_{off}$ can be determined by adding a non-barcoded competitor molecule capable of competing with the target molecule for binding to the specific binding agent. The target molecules that remain bound to the support can be isolated, and barcodes associated with the target molecules can be sequenced to determine the quantity of target molecules that remained bound to the support.

An exemplary method for measuring binding affinity includes binding tagged target molecule-specific binding agent complexes to a support (for example, via a biotin moiety attached to one component of the complex). The support can then be exposed to one or more wash conditions. The barcodes associated with the target molecules removed in each wash can be sequenced separately to determine the abundance of that unbound fraction. The barcodes can also be cleaved off the complexes still bound to the support after the washes to determine the abundance of the bound fraction. In certain embodiments, the bound fraction is permitted to remain bound to the support for about one to two days. The relative abundance of unbound fractions and the bound fraction can be compared to determine the dissociation rate. Multiple rounds of washes can be performed in this manner to generate a Kd curve. In an alternative embodiment, a specific binding agent can be used to isolate a fraction of a plurality of target molecules (for example, by immunoprecipitation using an antibody as a specific binding agent). This bound fraction, or a portion thereof, can be subsequently washed from the specific binding agent. Barcodes associated with the target molecules can be isolated from the bound and unbound fractions. The relative abundance of the target molecule in the bound and unbound fractions can then be calculated to determine an affinity measurement. Multiple rounds of washes can be performed, with each subsequent wash removing an additional portion of the bound fraction, and the associated nucleic acid barcodes sequenced to generate an affinity curve. In one embodiment, the target molecules are bound to the specific binding agent for about one to two days prior to washing.

5. Reporter Cells

The methods of the disclosure can be used to analyze properties of target molecules, for example, target polypeptide molecules. For example, target molecules may induce responses in cells. In some instances, a target molecule can be a soluble signal (for example, a secreted protein, peptide, small molecule, or other specific binding agent) capable of interacting with a cell (for example, by binding to a cell surface receptor), thereby inducing a downstream effect in the cell. Exemplary downstream effects include, without limitation, changes (for example, increases or decreases) in gene expression (for example, changes in mRNA expression level), changes in intracellular signaling pathways, and/or activation or inhibition of cellular activities (for example, cell proliferation, cell growth, cell death, change in cell morphology, and/or change in cell motility).

Thus, a discreet volume of the methods of the disclosure can, in some embodiments, include one or more reporter cells in which such downstream effects can be induced by a target molecule. For example, expression of one or more mRNAs by a reporter cell can be altered (for example, increased or decreased) by direct or indirect interaction with the target molecule. Such an mRNA may, for example, encode a target molecule, or alternatively may not encode a target molecule. An mRNA can, in some instances, encode an encoded peptide tag. In certain embodiments, the mRNAs are labeled with origin-specific barcodes (for example, the same origin-specific barcode used to label the target molecule). For example, the mRNAs or corresponding cDNAs can be ligated to origin-specific barcodes. The labeled mRNAs or cDNAs can subsequently be obtained (for example, by lysing the reporter cell), and sequenced to determine how the expression of the mRNA in the reporter cell was altered by the target molecule (for example, by determining the quantity of each distinct mRNA in a particular discreet volume). In certain embodiments, the reporter cell is lysed, and the mRNAs labeled with origin-specific barcodes from multiple discreet volumes are pooled (for example, with the labeled target molecules or labeled tags), amplified, and sequenced. Labeled mRNAs may be, for example, converted to labeled cDNAs prior to pooling, amplifying, and/or sequencing. In particular embodiments, the entire transcriptome of the reporter cell is labeled with origin-specific barcodes and sequenced according to RNA-seq methods known in the art.

6. Protein Modification Detection

The methods of this disclosure can be used to determine that modification state, such as phosphorylation state of a protein in sample, such as cells and/or an acellular system. Proteins can undergo phosphorylation post translational modifications, for example tyrosine kinases. In certain embodiments, antibodies specific to the different test proteins are labeled with different single-stranded DNA tags. Cells of interest are incubated in appropriate media, with or without test agents, such as pharmaceutical agents or potential pharmaceutical agents. The cells are segregated into compartments with the DNA tag labeled protein target specific antibodies and in some cases biotin labeled antibodies specific to target domains lacking phosphorylation sites, and a hydrogel bead carrying a mix of barcoded-primers complementary to the DNA tags of the DNA tag labeled target specific antibodies.

The target protein specific antibodies may be commercially available already conjugated with biotin, or may be modified for example with biotin via an NETS-ester reaction with lysine residues, or by conjugation of a hydrazide moiety to an oxidized antibody carbohydrate residue. The DNA tag labeled target specific antibodies are specific to the phosphorylation region of the target proteins. One antibody against the phosphorylated protein and one against the non-phosphorylated are used to encode specific tags for each state. In some examples, a third antibody comprising a detectable label, specific to a domain of the protein that does not contain a phosphorylation site, is used to label the bound complexes. The label allows later separation of antibody-target complexes from unbound antibodies. Alternatively, the complexes can be purified by size exclusion chromatography, without the use of the third antibody.

The compartments are incubated with a cleavage agent that will cleave and release the barcoded oligonucleotides into the whole volume. At the same time, the cell is lysed and the released target proteins captured by the labeled antibodies, which anneal their complementary sequence on the single-stranded part of the hydrogel-bound barcoded DNA and the polymerase will extend the barcoded DNA molecule, copying the DNA tag. These antibody-target complexes are captured by the biotin labeled antibodies. The addition of the DNA barcode to the antibody bound DNA tags gives single cell specificity to these sequences.

In an alternative embodiment, antibodies specific to the different target proteins are labeled with different double-stranded DNA tags. Single cell level target protein phosphorylation data is to be quantified, and compared with total target protein quantities, via the number of target specific DNA tag reads for each DNA barcode. Single cell level mRNA expression and sequence information is also available from the sequencing.

7. Combinatorial Chemistry

The disclosure provides methods for coupling a target molecule to a plurality of nucleic acid barcodes, for example, in the form of a concatemer of barcodes. Each barcode can be, for example, associated with a particular condition (for example, a compound (such as, for example, a small molecule compound, a nucleic acid, a polypeptide, or a polysaccharide), temperature, incubation time, atmospheric conditions, and pH), such that the set of conditions to which the target molecule is exposed can be determined by sequencing the barcodes. In some embodiments, each barcode is added to a growing barcode concatemer as the target molecule is exposed to the condition with which the barcode is associated, such that sequencing the barcode concatemer reveals the order in which the target molecule was exposed to each condition. The barcodes can be associated with an affinity moiety, which can recognize the target molecule and thus facilitate coupling of the barcode and target molecule. In certain embodiments, the target molecule is exposed to a plurality of compounds (for example, small molecules, nucleic acids, peptides, polysaccharides, or combinations thereof), and each of the compounds is associated with a distinct nucleic acid barcode, which can be coupled to the target molecule in turn (for example, by adding each barcode to a growing barcode concatemer). For example, a target molecule can be exposed to a set of reaction conditions, each featuring a particular compound, in which each exposure results in addition of a distinct barcode to the target molecule. Thus, the compounds to which the target molecule was exposed, and the order of their exposure, can be determined afterward by sequencing the barcodes associated with the target molecule.

D. Compositions and Kits

The present disclosure also concerns compositions and kits that can be used in carrying out the methods of the disclosure. In one example, a disclosed composition includes a barcode labeling complex. The barcode labeling complex includes a solid or semi-solid substrate (such as a bead, for example a hydrogel bead), and a plurality of barcoding elements reversibly coupled thereto, wherein each of the barcoding elements comprises an indexing nucleic acid identification sequence (such as RNA, DNA or a combination thereof) and one or more of a nucleic acid capture sequence that specifically binds to target nucleic acids and a specific binding agent that specifically binds to the target molecules. In some examples, the origin-specific barcode further includes one or more cleavage sites. In some examples, at least one cleavage site is oriented such that cleavage at that site releases the origin-specific barcode from a substrate to which it is coupled. In some examples, at least one cleavage site is oriented such that the cleavage at the site releases the origin-specific barcode from the target molecule specific binding agent. In some examples, the origin-specific barcode further comprises one or more capture moieties, covalently or non-covalently linked. In certain example, the one or more capture moieties comprise biotin, such as biotin-16-UTP. In some examples, the origin-specific barcode further comprises one or more of a sequencing adaptor or a universal priming sites. In some examples, the target molecule specific binding agent comprises an antibody or a fragment thereof, a polypeptide or peptide comprising an epitope recognized by the target molecule, or a nucleic acid. In some examples, each of the origin-specific barcodes comprises one or more indexes, one or more sequences that enable gene specific capture and/or amplification, and/or one or more sequences that enable sequencing library construction. In some examples each of the barcodes comprises four indexes, which can be combinatorially assembled. In some examples, the sequences that enable sequencing library construction comprise an Illumina P7 (SEQ ID NO: 11) sequence and/or an Illumina sequencing primer. In some examples, the barcodes comprises a primer for DNA synthesis, such as a primer suitable for DNA synthesis on a DNA template or an RNA template. Also disclosed are kits that can include any and all of the compositions disclosed herein.

The invention is further defined with reference to the following numbered clauses:

1. A method of assigning coupling phenotype to genotype to a set of target molecules associated to specific compartments, comprising:
   providing a sample comprising cells, or an acellular system, comprising target molecules of interest and/or nucleic acids encoding target molecules of interest;
   segregating, a subset of cells, single cells, or a portion of the acellular system from the sample into individual compartments, wherein each individual compartment further comprises an origin-specific barcode, comprising a unique nucleic acid identification sequence that maintains or carries information about the compartment of origin of the segregated cell or acellular system in the sample;
   labeling the target molecules in the individual compartments with the origin-specific barcodes present in the individual compartments to create origin-labeled target molecules, wherein the origin-labeled target molecules from each individual compartment comprise the same unique indexing nucleic acid identification sequence or matched indexing sequence, optionally further labeling or separating the target molecules according to their physical and chemical properties to provide additional property or abundance information also associated with the origin-specific barcodes;
   associating properties of the target molecules with the individual compartments and/or cells in the compartments;
   detecting the nucleotide sequence of the origin-specific barcodes, thereby assigning the set of target molecules to a specific compartments and properties of the target molecules in the specific compartments.
2. The method of clause 1, further comprising, assigning the set of target molecules to target nucleic acids in the sample or set of samples, wherein the sample comprising, further comprises target nucleic acids of interest; and the method further comprises:
   labeling the target nucleic acids in the individual compartments with the origin-specific barcodes present in the individual compartments to create origin-labeled target nucleic acids, wherein the origin-labeled target nucleic acids from each individual compartment comprise the same or matched, unique indexing nucleic acid identification sequence as the origin-labeled target molecules;
   detecting the nucleotide sequence of the origin-specific barcodes, thereby assigning the set of target molecules to target nucleic acids in the sample or set of samples while maintaining information about the compartment of origin of the target molecules and the target nucleic acids.
3. The method of clauses 1 or 2, wherein the origin-specific barcodes comprise RNA, DNA, or a combination thereof
4. The method of any one of clause 1-3, wherein the origin-specific barcodes are reversibly coupled to a solid or semisolid substrate.
5. The method of any one of clauses 1-4, further comprising encapsulating the single cells or a portion of the acellular system from the sample together with a bead comprising the origin-specific barcodes reversibly coupled thereto.
6. The method of any one of clauses 1-5, wherein the origin-specific barcodes further comprise a nucleic acid capture sequence that specifically binds to the target nucleic acids and/or a specific binding agent that specifically binds to the target molecules.
7. The method of clause 6, wherein the origin-specific barcodes comprise two or more populations of origin-specific barcodes, wherein a first population comprises the nucleic acid capture sequence and a second population comprises the specific binding agent that specifically binds to the target molecules.
8. The method of any one of clauses 2-7, wherein the target nucleic acids comprise RNA or DNA.
9. The method of clause 8, wherein the target nucleic acid comprises mRNA, genomic DNA, or cDNA.
10. The method of any one of clauses 2-9, further comprising synthesizing cDNAs from the target nucleic acids, wherein the cDNA comprises the nucleic acid sequence of the target nucleic acid, or a fragment thereof and the sequence of the origin-specific barcode.
11. The method of clause 10, wherein the origin-specific barcodes are primers for the cDNA synthesis.
12. The method of clause 11, wherein the target nucleic acid, or complement thereof, encode a polypeptide of interest.
13. The method of any one of clauses 7-12, wherein target molecule comprises a target polypeptide and the specific binding agent that specifically binds to the target molecule in the sample comprises a polypeptide specific binding agent that specifically binds to a target polypeptide.
14. The method of clause 13, wherein the polypeptide specific binding agent comprises an antibody, or fragment thereof and/or a protein-binding domain or fragment thereof, or a nucleic acid sequence that specifically binds to the target polypeptide or a cell expressing a cell surface marker that specifically binds to the target polypeptide.
15. The method of one of clauses 1-14, wherein the target molecule comprises a target DNA and the specific binding agent that specifically binds to the target molecules in the sample comprises a nucleic acid sequence or DNA binding domain that specifically binds, and/or hybridizes to the target DNA.
16. The method of any one of clauses 1-15, wherein the origin-specific barcode further comprise a sequencing adaptor.
17. The method of any one of clauses 1-16, wherein the origin-specific barcode further comprises universal priming sites.
18. The method of any one of clauses 1-17, further comprising, pooling the individual compartments to create a pooled sample.

19. The method of clause 18, further comprising, selectively isolating the origin-labeled molecules and origin-labeled nucleic acids from the pooled sample.
20. The method of any one of clauses 1-19, wherein the origin-specific barcode further comprises a one or more capture moieties, covalently or non-covalently linked.
21. The method of clause 20, wherein isolating the origin-labeled molecules and origin-labeled nucleic acids comprises capturing the origin-specific barcode via the one or more capture moieties.
22. The method of any one of clauses 20-21, wherein the one or more capture moieties is captured with a capture moiety specific binding agent that specifically binds to the one or more capture moieties.
23. The method of any one of clauses 20-22, wherein the one or more capture moieties is captured on a solid support.
24. The method of any one of clauses 22-23, wherein the capture moiety specific binding agent is attached to the solid support.
25. The method of any one of clauses 20-24, wherein the one or more capture moieties comprises biotin.
26. The method of any one of clauses 22-25, wherein the capture moiety specific binding agent comprises streptavidin.
27. The method of any one of clauses 1-26, wherein the origin-specific barcode comprises biotin-16-UTP.
28. The method of any one of clauses 1-27, wherein labeling of the target molecule comprises directly attaching the origin-specific barcode to the target molecule.
29. The method of any one of clauses 1-28, wherein labeling of the target molecule comprises indirectly attaching the origin-specific barcode to the target molecule.
30. The method of any one of clauses 29, wherein indirect attachment comprises binding a target molecule specific binding agent to the target molecule, where the target molecule specific binding agent is indirectly or directly attached to the origin-specific barcode.
31. The method of clause 30, wherein the target molecule specific binding agent comprises an antibody or a fragment thereof, a polypeptide or peptide that specifically bind to the target molecule, or nucleic acid.
32. The method of any one of clauses 1-31, wherein the origin-specific barcode further comprises a primer-specific region.
33. The method of any one of clauses 1-32, wherein each of the origin-specific barcodes further comprises a unique molecular identifier.
34. The method of any one of clauses 1-33 wherein each of the origin-specific barcodes comprises one or more indexes, one or more sequences that enable gene specific capture and/or amplification, and/or one or more sequences that enable sequencing library construction.
35. The method of any one of clauses 1-34, wherein the target molecule is attached to an origin-specific barcode receiving adapter.
36. The method of clause 35, wherein the origin-specific barcode receiving adapter comprises a nucleic acid.
37. The method of clause 36, wherein the origin-specific barcode receiving adapter comprises an overhang and the origin-specific barcode comprises a sequence capable of hybridizing to the overhang.
38. The method of any one of clauses 30-37, wherein the target molecule specific binding agent specifically binds both the target molecule and the origin-specific barcode.
39. The method of any one of clauses 30-38, wherein the target molecules are incubated with the target molecule specific binding agent that bind both the target molecules and the origin-specific barcode and the target molecule specific binding agent that are not bound to the target molecule and/or origin-specific barcode are removed prior to segregation into the individual compartments.
40. The method of any one of clauses 30-39, wherein the target molecule specific binding agent comprises a target molecule specific binding agent barcode, encoding the identity of the target molecule specific binding agent.
41. The method of clause 40, wherein the nucleic acid comprising the target molecule specific binding agent barcode can bind to the nucleic acid comprising the origin-specific barcode via base-pairing interactions.
42. The method of any one of clauses 40-41, wherein the origin-specific barcode is a primer for the synthesis of the complementary strand of the target molecule specific binding agent barcode.
43. The method of any one of clauses 40-42, further comprising, detecting the sequence of the target molecule specific binding agent barcode.
44. The method of any one of clauses 1-43, wherein the origin-specific barcodes are delivered to the individual compartment by delivering a single bead to each individual compartment wherein each bead carries multiple copies of a single origin-specific barcode.
45. The method of any one of clauses 1-44, wherein the compartment comprises an aqueous droplet in an emulsion.
46. The method of clause 45, wherein the emulsion comprises one or more surfactants, thereby stabilizing the emulsion.
47. The method of any one of clauses 45-46, wherein the emulsion comprises a continuous phase and the continuous phase of the emulsion comprises a fluorinated oil.
48. The method of any one of clauses 46-47, wherein the one or more surfactants comprises one or more fluorinated surfactants.
49. The method of any one of clauses 45-48, further comprising, breaking the emulsion, thereby pooling the contents of the individual compartments.
50. The method of any one of clauses 1-49, wherein the target molecule comprises a polypeptide, nucleic acid, polysaccharide, and/or small molecule.
51. The method of clause 50, wherein the polypeptide comprises an antibody, an antigen, or a fragment thereof.
52. The method of any one of clauses 1-51, wherein the target molecules represent a library of randomly or systematically mutated polypeptides.
53. The method of any one of clauses 1-52, wherein the target molecule is expressed on the surface of a cell.
54. The method of clause 53, wherein the target molecules comprises a cell surface protein, or a fragment thereof, such as a cell surface domain of a protein.
55. The method of any one of clauses 1 to 54, wherein the sample comprises one or more cells.

56. The method of any one of clauses 1 to 55, wherein samples comprises the acellular system of target molecules and target nucleic acids.
57. The method of clause 56, comprises a cell-free extract or a cell-free transcription and/or cell-free translation mixture.
58. The method of any one of clauses 1 to 57, wherein the sample comprises one or more synthetic genetic constructs comprising one or more polypeptide coding sequence operably connected to a promoter.
59. The method of clause 58, wherein the one or more synthetic genetic constructs comprises a set of synthetic genetic constructs, which optionally are comprised of combinatorially generated parts.
60. The method of any one of clauses 7-59, wherein the first population of origin-specific barcodes further comprises a target nucleic acid barcode, wherein the target nucleic acid barcode identifies the population as one that labels nucleic acids.
61. The method of any one of clauses 7-60, wherein the second population of origin-specific barcodes further comprises a target molecule barcode, wherein the target molecule barcode identifies the population as one that labels target molecules.
62. The method of any one of clauses 1-61, wherein the origin-specific barcode further comprises one or more cleavage sites.
63. The method of clause 62, wherein at least one cleavage site is oriented such that cleavage at that site releases the origin-specific barcode from a substrate to which it is coupled.
64. The method of clause 63, wherein the substrate comprises the bead.
65. The method of any one of clauses 62-64, wherein at least one cleavage site is oriented such that the cleavage at the site releases the origin-specific barcode from the target molecule specific binding agent.
66. The method of any one of clauses 1-65, further comprising lysing the cells.
67. The method of any one of clauses 1-66, wherein the target molecules, optionally in association and the target nucleic acids are produced by the individual cells in the individual compartments.
68. The method of any one of clauses 1-67, wherein the cells are B-cells, plasmablasts or plasma cells, and the target molecules are antibodies and the target nucleic acids encode the antibodies.
69. The method of any one of clauses 1-68, wherein the target molecules are polypeptides and the target nucleic acids encodes the target molecules in their respective individual compartments.
70. The method of any one of clauses 1-69, wherein the cells are contacted with one or more test agents.
71. The method of clause 70, wherein the test agents comprise small molecule, a nucleic acid, a polypeptide, or a polysaccharide.
72. The method of clause 71, wherein the polypeptide comprises an antibody or an antibody fragment.
73. The method of any one of clauses 70-72, further comprising labeling the test agent with the origin-specific barcode.
74. The method of any one of clauses 70-73, wherein the individual test agents are labeled with a test-agent specific barcodes.
75. The method of any one of clauses 1-74, further comprising, amplifying one or more of the origin-specific barcodes, the target molecule specific binding agent barcodes, test-agent specific barcodes, the target nucleic acid barcodes, and the target molecule barcodes.
76. The method of any one of clauses 1-75, further comprising, detecting one or more of the target molecule specific binding agent barcodes, test-agent specific barcodes, the target nucleic acid barcodes, and the target molecule barcodes.
77. The method of any one of clauses 1-76, wherein detecting the sequence of the origin-specific barcodes, the target molecule specific binding agent barcodes, test-agent specific barcodes, the target nucleic acid barcodes, and/or the target molecule barcodes comprises hybridization, sequencing, or a combination thereof.
78. The method of any one of clauses 1-77, further comprising, quantifying one or more of the origin-specific barcodes, the target molecule specific binding agent barcodes, test-agent specific barcodes, the target nucleic acid barcodes, and the target molecule barcodes.
79. The method of any one of clauses 1-78, further comprising, prior to segregation, contacting the cells with a specific binding agents that specifically binds to target molecules on the surface of the cells.
80. The method of clause 79, where the specific binding agents comprise antigens and the target molecules comprise antibodies.
81. The method of any one of clauses 79-80, further comprising, after segregation, lysing the cells, wherein the specific binding agent is bound by the origin-specific barcode.
82. The method of clause 81, wherein the antigen is further labeled with a ssDNA or partially double stranded DNA and the complementary strand synthesized using the origin-specific barcode as primer.
83. The method of any one of clauses 81-82, further comprising synthesizing cDNA from mRNA encoding the antibody heavy and/or light chain, wherein the origin-specific barcode primes the cDNA synthesis.
84. The method of any one of clauses 79-83, further comprising pooling the compartments and quantifying the amount of antigen bound to the antibody on the surface of each cell using the origin-specific bar code on the antigen.
85. The method of any one of clauses 79-84, further comprising, determining the sequence of the heavy and/or light chain and assigning that sequence to the antigen biding the antibody.
86. The method of any one of clauses 79-85, wherein the antigens comprise HIV antigens, such as gp41 and/or gp120.
87. A method of determining the specificity of a test agent for target molecules, comprising assigning a set of target molecules to compartments according to any one of clauses 1-78, wherein the method further comprises:
contacting the cells expressing target molecules, prior to segregation, with a pool of test agents labeled with a test agent specific barcode;
isolating the target molecules bound to test agents; and
determine the sequence of the test agent specific barcodes and the sequence of the origin specific barcode, thereby identifying the test agents bound to the target molecules.
88. The method of clause 87, wherein the target molecule comprises a cell surface protein and the target nucleic acid encodes the cell surface protein.

89. The method of any one of clauses 87-88, further comprising washing unbound test agents from the cells.
90. The method of any one of clauses 87-89, wherein the target nucleic acid is a DNA or RNA.
91. The method of any one of clauses 87-90, wherein the target nucleic acid is a cDNA or mRNA.
92. The method of any one of clauses 87-91, further comprises labeling the test agents with the origin-specific barcode.
93. The method of any one of clauses 87-92, wherein the test agent comprises a small molecule compound, a nucleic acid, a polypeptide, or a polysaccharide.
94. A method of determining a target molecules affinity and/or specificity for a test agent, comprising assigning a set of target molecules to compartments a according to any one of clauses 1-78, the method further comprising:
contacting the labeled target molecules with a test agent bound with a detectable label;
isolating the labeled target molecules bound to the test agent using the detectable label;
determine the sequence of origin-specific barcode on the isolated target molecules; and
quantifying the origin-specific barcodes associated with the isolated target molecules, thereby determining the affinity of the test agent for the target molecules.
95. The method of clause 94, further comprising quantifying the origin-specific barcodes that are not isolated with the test agent to normalize concentration.
96. The method of any one of clauses 94-95, further comprising cleaving the origin-specific barcodes after isolation.
97. The method of any one of clauses 94-96, further comprising associating the isolated barcodes with the target nucleic acids to determine the sequence of the target molecules bound to the test agent.
98. The method of any one of clauses 94-97, wherein the target molecules comprises polypeptides.
99. The method of clause 98, wherein the polypeptides comprise antibodies.
100. The method of clause 99, wherein the antibodies comprises anti-HIV antibodies, such as anti-gp41 or anti-gp120 antibodies and the test agents comprise a set of potential HIV antigens and/or immunogens.
101. The method of clause 100, wherein the test agent comprises an antibody, and the target molecules comprise proteins expressed on the surface of the cell.
102. The method of clause 101, wherein the test agent comprises an anti-HIV antibody, such as an anti-gp41 or gp120 antibody and the target molecules comprise a set of HIV antigens and/or immunogens.
103. The method of any one of clauses 94-102, further comprising one or more of determining the dissociation constant, on-rate, or off-rate of the target molecule for the test agent.
104. A method of determining the expression of target molecules on the surface of a set of cells, comprising assigning a set of target molecules to compartments according to any one of clauses 1-78, the method further comprising:
contacting the sample cells to be segregated with a set of test agents each labeled with a unique test agent barcode;
determining the sequence of origin-specific barcode, thereby determining the expression of molecules on the surface of the set of cells.
105. The method of clause 104, further comprising associating the isolated barcodes with the target nucleic acids to determine the sequence of the target molecules bound to the test agent.
106. The method of any one of clauses 104-105, wherein the test agents comprises polypeptides.
107. The method of clause 106, wherein the polypeptides comprise antibodies, specific for cell surface markers.
108. The method of any one of clauses 104-108, further comprising associating the molecules expressed on the surface of the cells with the cell type, cell cycle or other measure of cellular state.
109. A method of identifying a protein having a specific activity of interest from a population of cells, comprising assigning a set of target molecules to compartments according to any one of clauses 1-78, the method further comprising:
isolating the target molecules having the specific activity of interest; and
identifying the origin-specific barcodes of the isolated target molecules having the specific activity interest.
110. The method of claim clause, further comprising identifying the target nucleic acid molecules encoding the proteins by matching of sequences of origin-specific nucleic acid barcodes.
111. The method of claim clause, wherein the activity is antigen binding and proteins are antibodies.
112. The method of claim clause, further comprising producing an antibody of interest by expression of a nucleic acid molecule identified as encoding an antibody of interest.
113. A method of detecting and/or quantifying a post-translationally modified a target molecule in a sample comprising assigning a set of target molecules to specific compartments according to any one of clauses 1-78, the method further comprising:
contacting the labeled target molecules with a first specific binding agent that specifically binds the post-translationally modified target molecule at the site of modification and a second specific binding agent that specifically binds non-post-translationally modified target molecule at the site of modification, wherein the first and second specific binding are labeled with a specific binding agent specific barcode;
isolating the target molecules, thereby isolating the specific binding agents bound to the target molecules;
determining the sequence of origin-specific barcode and the specific binding agent barcode present on the isolated specific binding agents, thereby determining the presence of the post translationally modified protein in the sample.
114. The method of clause 113, wherein the post-translational modification comprises phosphorylation.
115. The method of any one of clauses 113-114, wherein the isolation comprises contacting the target molecule with a third specific binding agent that does not bind the site of modification.
116. The method of any one of clauses 113-115, wherein the specific binding agents comprise antibodies.
117. A barcode labeling complex, comprising:
a solid or semi-solid substrate, and
a plurality of barcoding elements reversibly coupled thereto, wherein each of the barcoding elements comprises an indexing nucleic acid identification sequence and one or more of a nucleic acid capture sequence that specifically binds to target nucleic acids and a specific binding agent that specifically binds to the target molecules.

118. The complex of clause 117, wherein the substrate comprises a bead.
119. The complex of clause 117, wherein the substrate comprises a hydrogel.
120. The complex of any one of clauses 117-119, wherein the origin-specific barcode further comprises one or more cleavage sites.
121. The complex of clause 120, wherein at least one cleavage site is oriented such that cleavage at that site releases the origin-specific barcode from a substrate to which it is coupled.
122. The complex of any one of clauses 117-121, wherein at least one cleavage site is oriented such that the cleavage at the site releases the origin-specific barcode from the target molecule specific binding agent.
123. The complex of any one of clauses 117-122, wherein the indexing nucleic acid identification sequence comprises RNA, DNA or a combination thereof.
124. The complex of any one of clauses 117-123, wherein the origin-specific barcodes comprise RNA, DNA, or a combination thereof.
125. The complex of any one of clauses 117-124, wherein the origin-specific barcode further comprises one or more capture moieties, covalently or non-covalently linked.
126. The complex of clause 125, wherein the one or more capture moieties comprises biotin.
127. The complex of any one of clauses 117-126, wherein the origin-specific barcode comprises biotin-16-UTP.
128. The complex of any one of clauses 117-127, wherein the origin-specific barcode further comprise a sequencing adaptor.
129. The complex of any one of clauses 117-128, wherein the origin-specific barcode further comprises universal priming sites.
130. The complex of any one of clauses 117-129, wherein the target molecule specific binding agent comprises an antibody or a fragment thereof, a polypeptide or peptide comprising an epitope recognized by the target molecule, or a nucleic acid.
131. The complex of any one of clauses 117-130, wherein each of the origin-specific barcodes comprises one or more indexes, one or more sequences that enable gene specific capture and/or amplification, and/or one or more sequences that enable sequencing library construction.
132. The complex of clause 131, wherein each of the barcodes comprises four indexes.
133. The complex of any one of clauses 131-132, wherein the one or more indexes are combinatorially assembled.
134. The complex of any one of clauses 131-133, wherein each of the sequences that enable sequencing library construction comprises an Illumina P7 sequence and/or an Illumina sequencing primer.
135. The complex of any one of clauses 117-133, wherein each of the barcodes comprises a primer for DNA synthesis.
136. The complex of clause 135, wherein the primer is suitable for DNA synthesis on a DNA template or an RNA template.
137. A method of determining the levels of post-translationally modified target proteins in a sample, comprising:

providing a sample comprising cells;
co-segregating single cells or a portion from the sample into individual compartments with a first specific binding agent that specifically binds the post-translationally modified target molecule at the site of modification and a second specific binding agent that specifically binds non-post-translationally modified target molecule at the site of modification, wherein the first and second specific binding are labeled with a specific binding agent specific barcode, wherein each individual compartment further comprises an origin-specific barcode, comprising a unique nucleic acid identification sequence that maintains or carries information about the compartment of origin of the segregated cell in the sample;
labeling the first specific binding agent the second specific binding agent in the individual compartments with the origin-specific barcodes present in the individual compartments;
isolating the target molecules, thereby isolating the first and second specific binding agents bound to the target molecules;
detecting the nucleotide sequence of origin-specific barcode and the specific binding agent barcode present on the isolated specific binding agents, thereby determining the presence of the post translationally modified protein in the sample.
138. The method of clause 137, wherein the post-translational modification comprises phosphorylation.
139. The method of any one of clauses 137-138, comprising quantitating the levels of post-translationally modified and unmodified target proteins.
140. The method of any one of clauses 137-139, wherein the isolation comprises contacting the target molecule with a third specific binding agent that does not bind the site of modification, wherein the third specific binding agent is detectably labeled.
141. The method of any one of clauses 137-140, wherein the specific binding agents comprise antibodies.
142. The method of any one of clauses 137-141, further comprising labeling target nucleic acids in the individual compartments the origin-specific barcodes present in the individual compartments to create origin-labeled target nucleic acids, wherein the origin-labeled target nucleic acids from each individual compartment comprise the same or matched, unique indexing nucleic acid identification sequence as the origin-labeled target molecules;
detecting the nucleotide sequence of the origin-specific barcodes, thereby assigning the set of target proteins to target nucleic acids in the sample or set of samples while maintaining information about the compartment of origin of the target proteins and the target nucleic acids.

The following examples are intended to illustrate, but not limit, the invention.

EXAMPLES

Example 1

Compartment-Specific Labeling of Target Molecules

The following example demonstrates the labeling of a set of molecules with the methods set forth herein.

In this example, the target molecule selected is an antigen, i.e., the HIV envelope glycoprotein gp120, for example as either in its natural isoform (wtGP120) or in the N332A mutant isoform (gp120$^{N332A}$). The two isoforms of the antigen are labeled with two different single-stranded DNA tags. B cells displaying immunoglobulin M (IgM) with affinity to either isoform of the antigen are then incubated together with a mixture of the labeled antigens. The cells are then washed and encapsulated in ~100 pL droplets with lysis buffer, reverse-transcription (RT) buffer and enzymes (RT enzyme, DNA polymerase and restriction enzyme BclI) and a hydrogel bead (Kim et al—Fabrication of monodisperse gel shells and functional microgels in microfluidic devices. Angew Chem Int Ed Engl. 2007; 46(11):1819-22; Abate, A. R. et al.—Beating Poisson encapsulation statistics using close-packed ordering. *Lab Chip* (2009). 9(18), 2628-31. doi:10.1039/b909386a) carrying a mix of barcoded-primers complementary to the DNA tags and to the mRNAs of the heavy and light chain antibody gene, using a microfluidic device.

Labeling of Antigen:

The antigen linkage to the DNA tag can be direct (covalent bond created via chemistry such as an NETS-ester reaction) or indirect (non-covalent binding such as biotin-streptavidin interaction). The following describes the second case.

The labeled antigen in its final form is structured as a biotinylated antigen bound in one pocket of a streptavidin molecule which has three other pockets bound by biotinylated single-stranded DNA tags (see FIG. 8). The DNA tag can be obtained directly as a biotinylated oligo or made by PCR and treated with Lambda Exonuclease. The following describe the second strategy.

The DNA tag is created by PCR with a pair of oligonucleotides with a 20-nucleotide (nt) 5' extension. The extension on one of the oligonucleotides is the Illumina® SBS3 (ACACTCTTTCCCTACACGACGCTCTTCCGATCT (SEQ ID NO: 2)) sequence and the extension on the other oligonucleotide is a randomly chosen sequence (such as GGAGTTGTCCCAATTCTTGT (SEQ ID NO: 3)), called tag specific primer (TSP), that is common to all antigen tags. The amplified region is a 100 base pair (bp) sequence of the pUC19 plasmid. A second PCR amplification is performed on this first product with a second set of primers identical to the 5' extensions of the first set of primer, i.e. SBS3 (SEQ ID NO: 2) and TSP. The SBS3 (SEQ ID NO: 2) primer from the second set carries a biotin on its 5' and the TSP primer has a 5' phosphate. The final double stranded product is then incubated with Lambda Exonuclease, which targets the 5' phosphorylated strand for degradation, the biotin protecting of the other strand. The final products are single-stranded, 5' biotinylated DNA molecules. Different DNA tags can be generated with this scheme by changing the amplified region of the plasmid at the first PCR step. Their sequences will be identical over ~20 nt at both extremities but the center will be different, providing different tags for different target molecules.

Here, two different tags are made by targeting two different regions of the pUC19 plasmid for the two versions of the gp120 antigen (wtGP120 and gp120$^{N332A}$ isoforms).

The targeted molecule is a recombinant antigen displaying a biotin. This antigen is first incubated with a 10-fold excess of free streptavidin, then washed and purified using commercially available size exclusion columns. The purified streptavidin-bound antigen is then incubated with a 10-fold excess of 5' biotinylated single-stranded DNA molecules (either commercially available oligos or the products of Lambda Exonuclease described above), then washed again and purified using size exclusion columns.

The final product is the antigen, whose biotin tag is bound by one pocket of a streptavidin molecule, the three other pockets being occupied by 5' biotin single-stranded DNA tag. Here the final products of wtGP120-tag1 and gp120$^{N332A}$-tag2 are mixed in equal ratio before incubation with cells (see FIG. 8).

Labeling of Cells:

Prior to compartmentalization, a population of various cells is incubated with the labeled antigens for 20 minutes then washed three times in a large volume of PBS. In a first control experiment, the population consists of a mixture of four different cell lines with defined and different affinity to either wtGP120 or gp120$^{N332A}$. In subsequent experiments, the cell populations come from an HIV infected patient's sample, such as from patients showing Broadly Neutralizing HIV-1 antibodies in their serum, or patients at different stages of infection.

Hydrogel Bead Production and Barcoded Oligonucleotide Synthesis:

In some examples, hydrogel beads are prepared from PEG-DA oligomers in a microfluidic chip, where an aqueous PEG-DA solution is dispersed to form droplets in a fluorinated oil continuous phase by hydrodynamic flow focusing (Anna, S., Bontoux, N., & Stone, H. (2003). Formation of dispersions using "flow focusing" in microchannels. *Applied Physics Letters*, 82(3), 364-366. doi:10.1063/1.1537519). The beads are then crosslinked via a UV activated photoinitiator. 400 μM of a double-stranded DNA oligonucleotide (duplex) called RanA, carrying a 5' acrydite modification on one end and a 4-nt 5' overhang on the other side (top strand: 5' Acrydite-TCTTCACGGAACGA (SEQ ID NO: 4); bottom strand: 5'Phosphate-CAGT TCGTTCCGTGAAGA (SEQ ID NO: 5)) is added and covalently crosslinked with the hydrogel matrix via acrylate end groups of the PEG-DA oligomers. After polymerization and washing in Tris-HCl pH 7.4 20 mM; NaCl 50 mM; Tween 0.01%; EDTA 1 mM, a first duplex with a 4-nt 5' overhang compatible with the overhang of the acrydite duplex on one side and another 4-nt 5' overhang compatible with downstream ligation on the other side is ligated using T7 DNA ligase. In its double-stranded part, this first duplex has for sequence a randomly chosen 8-nt sequence called RanB (GACTAGAA (SEQ ID NO: 6), followed by the BclI restriction site (TGATCA (SEQ ID NO: 7), followed by the SBS12 Illumina® sequence (GTGACTGGAGTTCAGACGTGTGCTCTTCCGATCT (SEQ ID NO: 8)).

Figure 9:
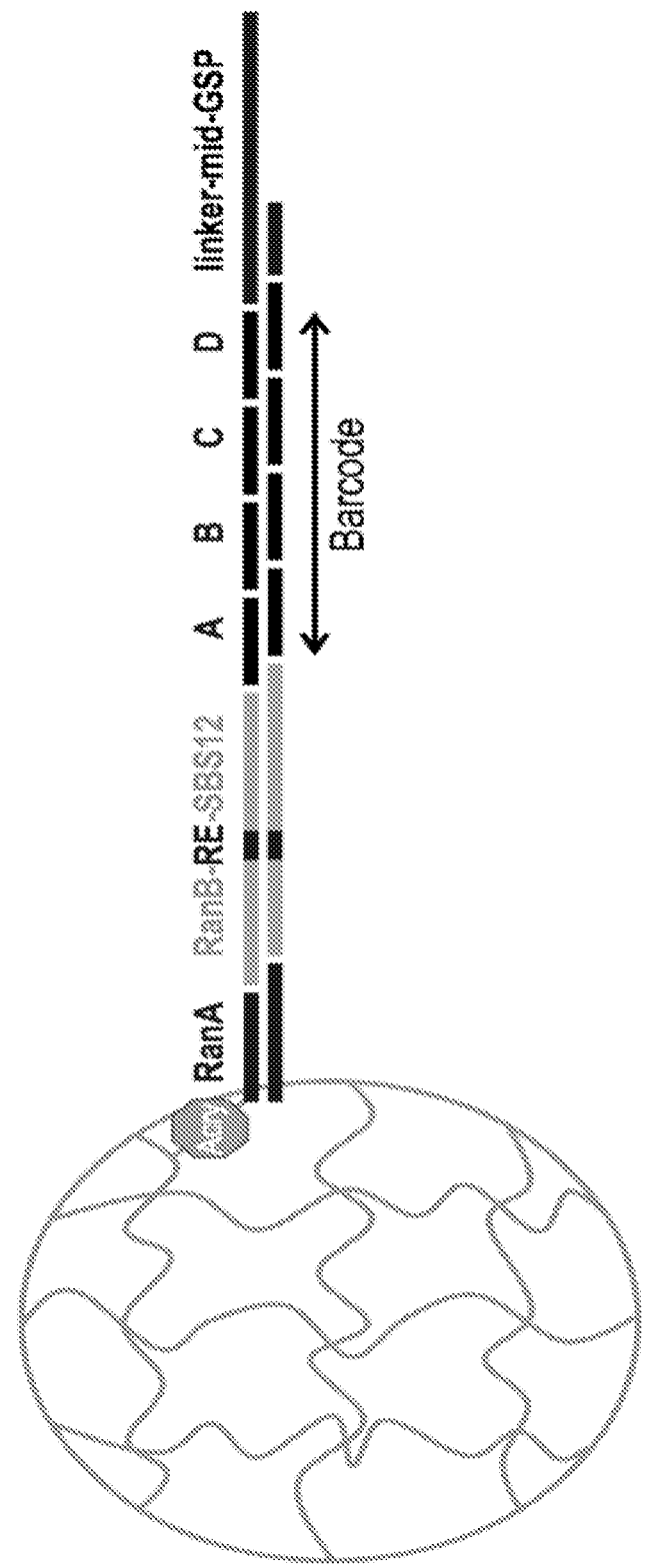
FIG. 9 is schematic of a hydrogel bead DNA barcoded structure.
Figure 10:
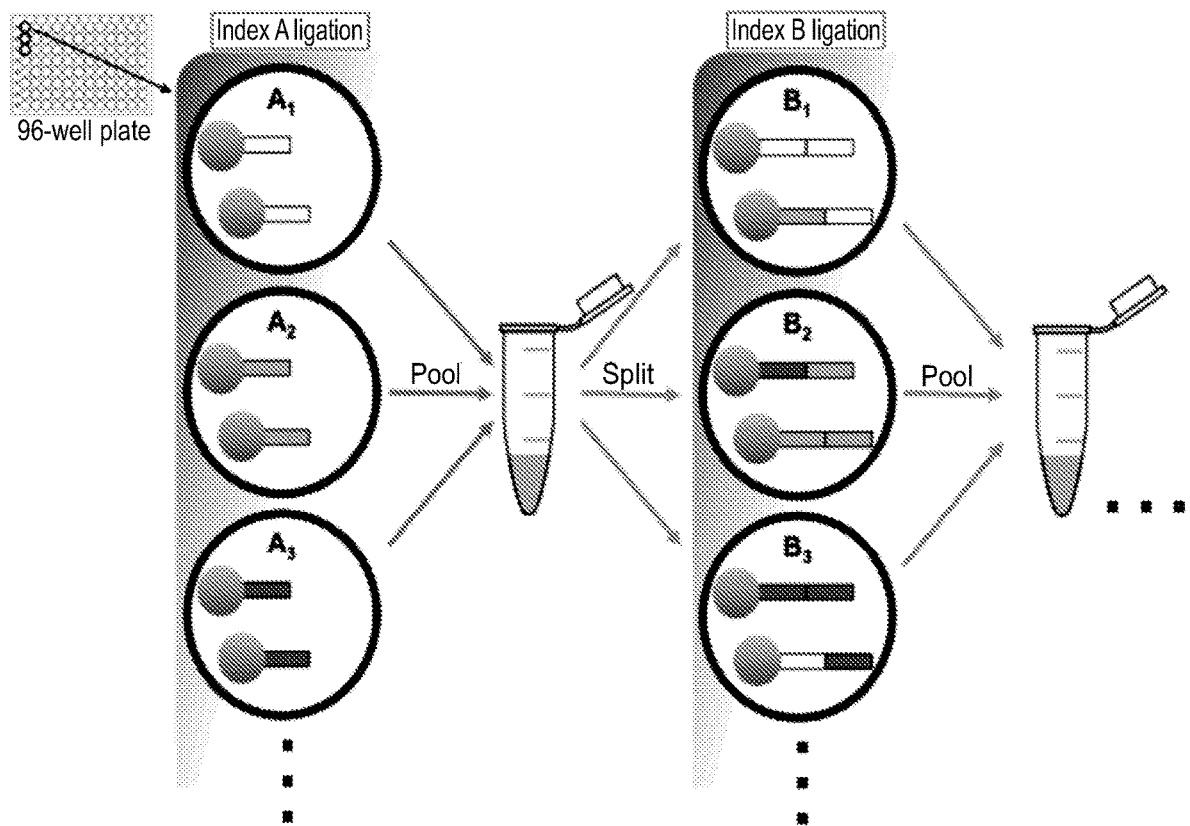
FIG. 10 is a schematic showing an example of "split-pool" DNA barcode labeling of hydrogel beads, such as shown in FIG. 9.

After ligation and washing, the barcode is synthesized by four consecutive ligations, mediated by T7 DNA ligase, of 20-nt DNA duplexes with a 4-nt overhang at both 5' ends. The use of different 4-nt overhangs in each ligation step ensures that the 4 indices can only assemble in the correct order. In order to create a wide diversity of barcodes, the hydrogel bead batch is equally distributed in the wells of a 96 well plate. Each well contains duplex with a unique 20-nt sequence (an index) which is designed to remain unambiguous with up to three errors, plus ligation buffer and enzyme. After the ligation incubation, reaction volumes of the whole plate are pooled in one tube and washed. The next ligation steps are performed in the same way: the pooled batch is equally distributed in a new plate containing another set of 96 different duplexes together with ligation buffer and enzyme. The combinatory diversity of this split-pool synthesis is 96$^4$ (over 84 million). Finally, the last duplex ligated to the newly synthesized barcode is partially double-stranded, to allow ligation by the T7 DNA ligase, and terminated by a long single-strand 3' end (see e.g. FIGS. 9 and 10). The double-stranded region is a defined linker sequence (TACGCTACGGAACGA (SEQ ID NO: 9). The single-stranded region consists of a randomized 12-nt sequence (GNNNGNNGNNNG (SEQ ID NO: 10), followed by the antisense sequences of the mRNA to prime reverse transcription, or by the antisense sequence of the TSP to prime DNA polymerization. The 12-nt random sequences serve as unique molecular identifiers (UMIs): they allow sequences originating from different RT priming event to be distinguished (with different UMIs) from sequences originating from PCR amplification of the same cDNA (with the same UMIs) (Shiroguchi, K., Jia, T. Z., Sims, P. A., & Xie, X. S. (2012). Digital RNA sequencing minimizes sequence-dependent bias and amplification noise with optimized single-molecule barcodes. *Proceedings of the National Academy of Sciences*, 109(4), 1347-1352. doi:10.1073/pnas.1118018109).

The release of the oligo, here by restriction enzyme cleavage, can be performed by replacing this sequence with any cleavable chemical group that can be attach to nucleic acids, such as photocleavable or pH-sensitive moieties.

Figure 11:
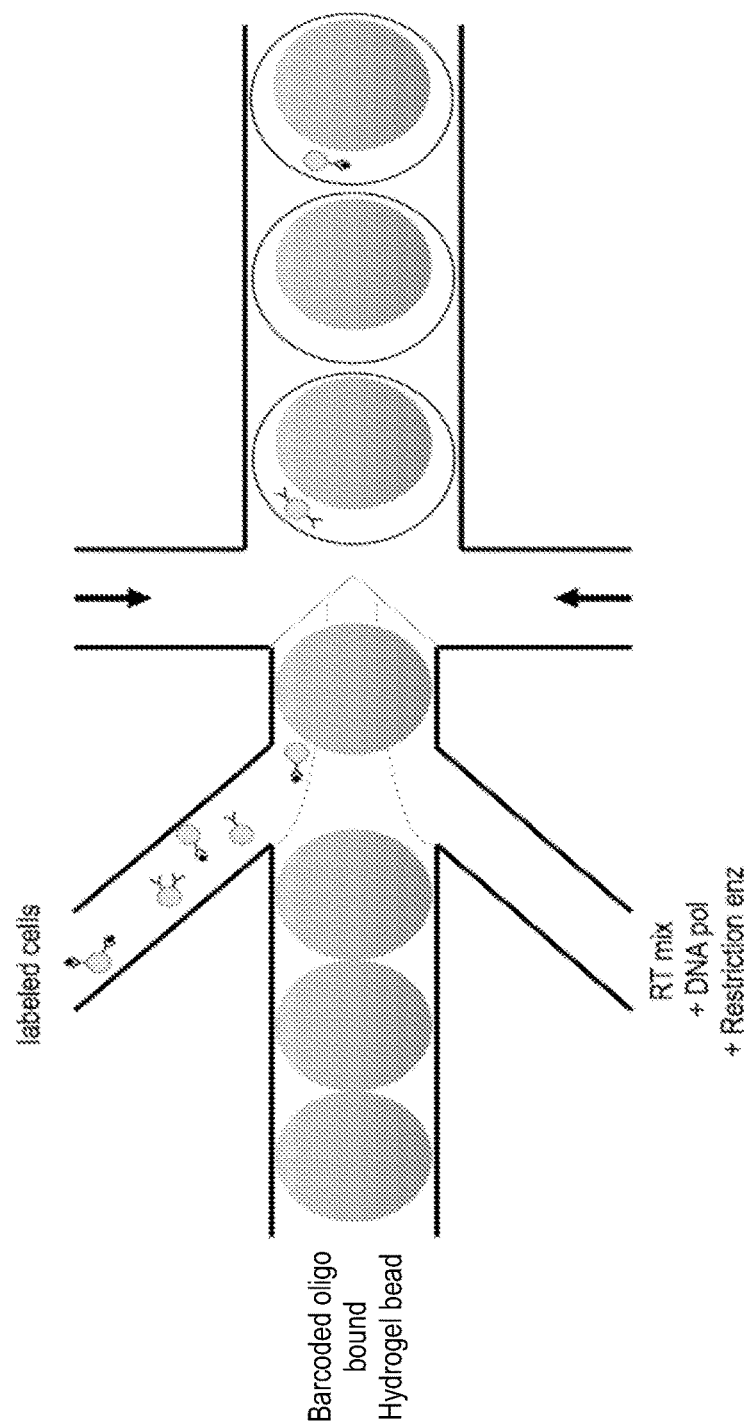
FIG. 11 is a schematic showing the encapsulation of reverse transcriptase and other reagents and a hydrogel bead into an emulsion drop using a microfluidic device.

Coding Phenotype into DNA—DNA Polymerization and RT in Drops:

Using a microfluidic chip, labeled cells are encapsulated in droplets together with lysis buffer, reverse transcription enzyme and its buffer, a DNA polymerase, the MI restriction enzyme and a hydrogel bead carrying a pool of partially double-stranded DNA molecules, all of them sharing the same DNA barcode; this DNA barcode is different on every hydrogel bead. Drops are produced with a Poisson distribution for cell encapsulation, and cell concentration is chosen such that the mean number of cells per droplet <1, ensuring that the majority of the drops contain no more than one cell. After The deformable hydrogel beads are injected as a closed packed array (Abate, A. R. et al. (2009)), ensuring that most drops contain a single bead (FIG. 11). The single-stranded part of the hydrogel bead-bound DNA molecules consists of a UMI sequence (SEQ ID NO: 10), followed by a sequence which is antisense to either the 3' end of the DNA tag or the most 5' end of the Constant (Fc) region of the Heavy and Light chains mRNA of the antibody genes (equal proportion of the 3 type of terminating sequences on the beads).

Figure 12:
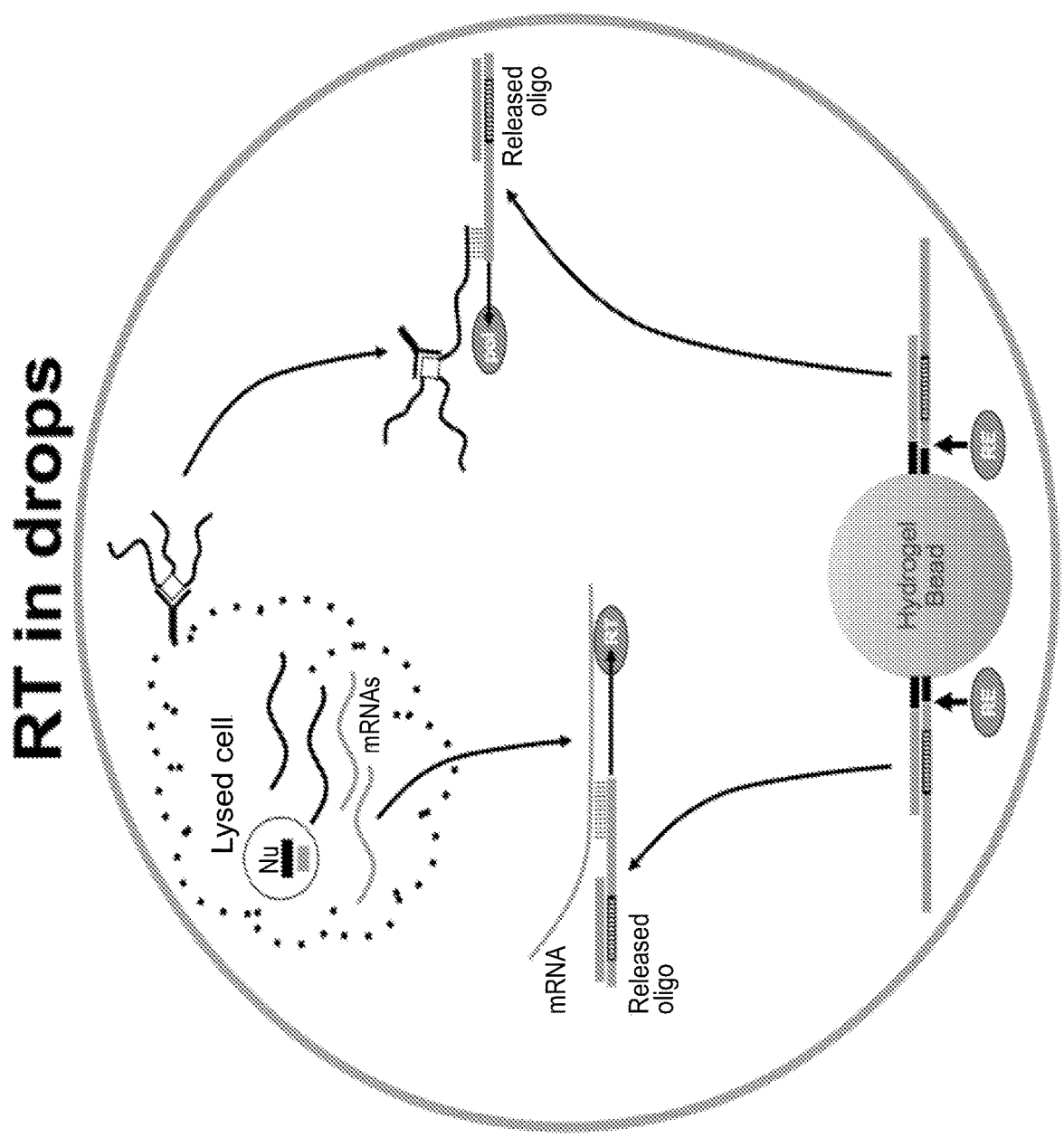
FIG. 12 is a schematic showing reverse transcription in an emulsion drop.

The emulsion is then placed at 55° C. for 1 h 30. During this incubation, The BclI restriction enzyme cleaves and releases the barcoded oligonucleotides into the whole volume of the drop. At the same time, the labeled cell is lysed and the released mRNA anneals to the complementary sequences on the single-stranded part of the released barcoded oligonucleotides, and the RT enzyme will extend the barcoded DNA, copying the sequence of the antibody heavy and light chain mRNA. Meanwhile, the antigen-bound DNA tag also anneals to its complementary sequence on the single-stranded part of the hydrogel-bound barcoded DNA and the polymerase extends the barcoded DNA molecule, copying the DNA tag. The addition of the DNA barcode to the mRNA derived cDNA and the antigen-bound DNA tags gives single cell specificity to these sequences (see e.g. FIG. 12).

Figure 13:
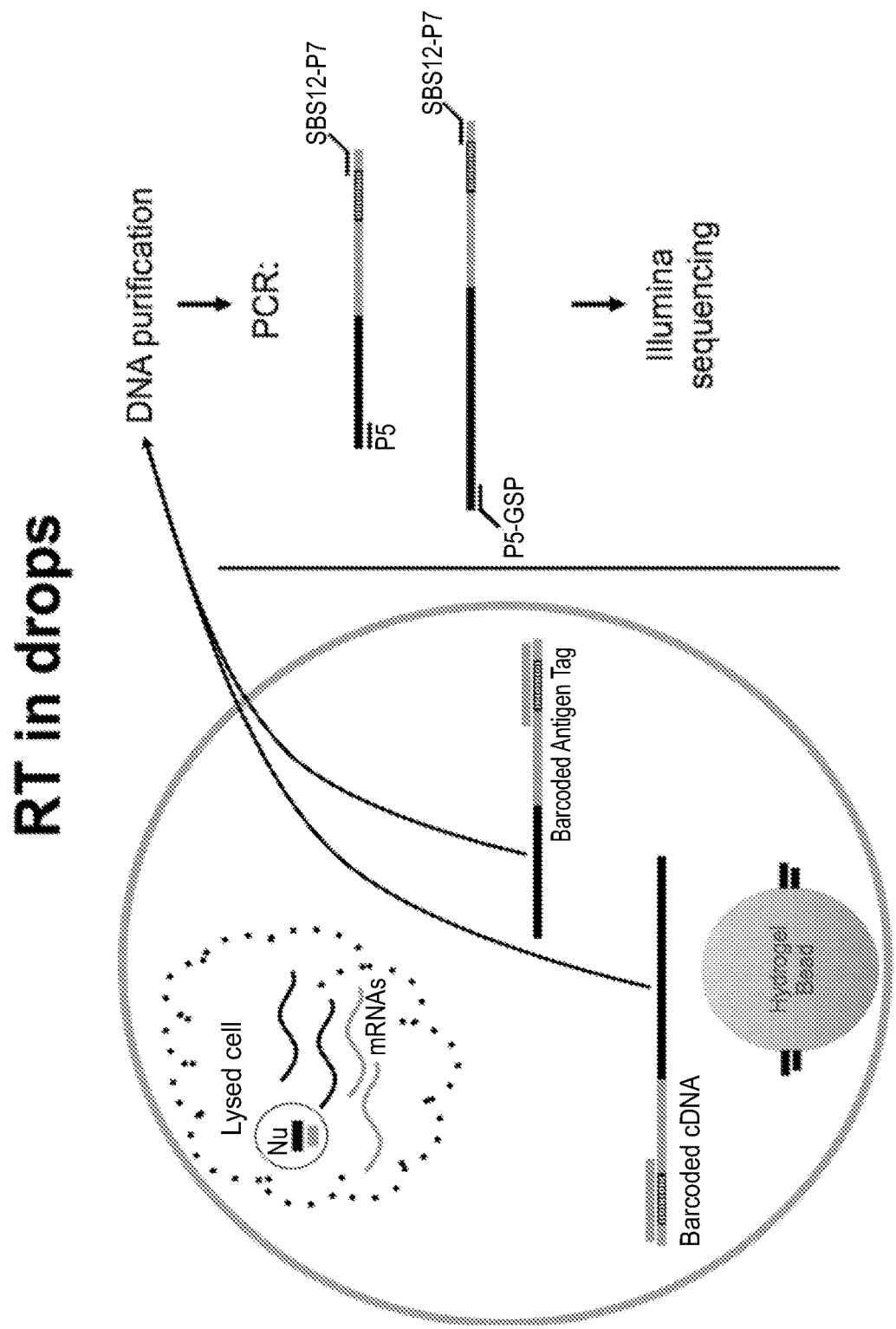
FIG. 13 is a schematic showing the results obtained from reverse transcription in emulsions drops.

Amplification in Bulk and Sequencing:

The emulsion is then placed at 70° C. to inactivate the RT enzyme, the emulsion is broken and the aqueous phase is recovered and DNA purified using commercial kits (Agencourt RNAClean XP).

cDNA and barcoded tags are then amplified in separate PCRs for heavy chain cDNA, light chain cDNA, and DNA tags. The primers used match the end of the cDNAs and DNA tags and have 5' extensions containing the sequences necessary for Illumina® sequencing i.e. anchoring sequences P7 (CAAGCAGAAGACGGCATACGAGAT (SEQ ID NO: 11)) and P5 (AATGATACGGCGAC-CACCGAGATCT (SEQ ID NO: 12)) (see e.g. FIG. 13).

Example 2

Phenotype and Sequence Recovery of Antibody-Secreting Cells

This example describes a variation of Example 1 which is adapted to sequencing selected antibody secreting cells, for example to screen for antibodies capable of binding to the HIV gp120 protein.

In this example, the target molecule is an antigen, i.e., the HIV envelope glycoprotein gp120 either in its natural isoform ($gp120^{wt}$) or in the N332A mutant isoform ($gp120^{N332A}$). The two isoform of the antigen are labeled with two different single-stranded DNA tags. Plasma cells are encapsulated in ~100 pl droplets that include a mix of culture media, DNA tagged (barcoded) antigens and a hydrogel bead carrying a mix of barcoded-primers complementary to the DNA tags and to the mRNAs of the heavy and light chain antibody gene using a microfluidic device. After incubation at 37° C., to allow secretion of antibody from the plasma cells, the droplets are fused with other droplets containing lysis buffer, RT buffer and enzymes (RT enzyme, DNA polymerase and a restriction enzyme, such as the restriction enzyme BclI) and a hydrogel bead carrying a mix of barcoded-primers complementary to the DNA tag and to the mRNAs of the heavy and light chain antibody gene using a microfluidic device. After incubation at 55° C. (which facilitates enzymatic digestion by MI, RT of the mRNA, and DNA polymerization) the emulsion is chemically broken and the aqueous phase is recovered. The antibodies and associated DNA tagged (barcodes) antigens are purified using commercially available protein-A/G agarose resin. cDNAs are purified from the protein-A/G agarose resin flow through. Antigen tags and cDNA are amplified separately by PCR and send sequenced.

Labeling of antigen is performed as for Example 1

Hydrogel Bead Production and Barcoded Oligonucleotide Synthesis:

Is performed as for Example 1.

Figure 14:
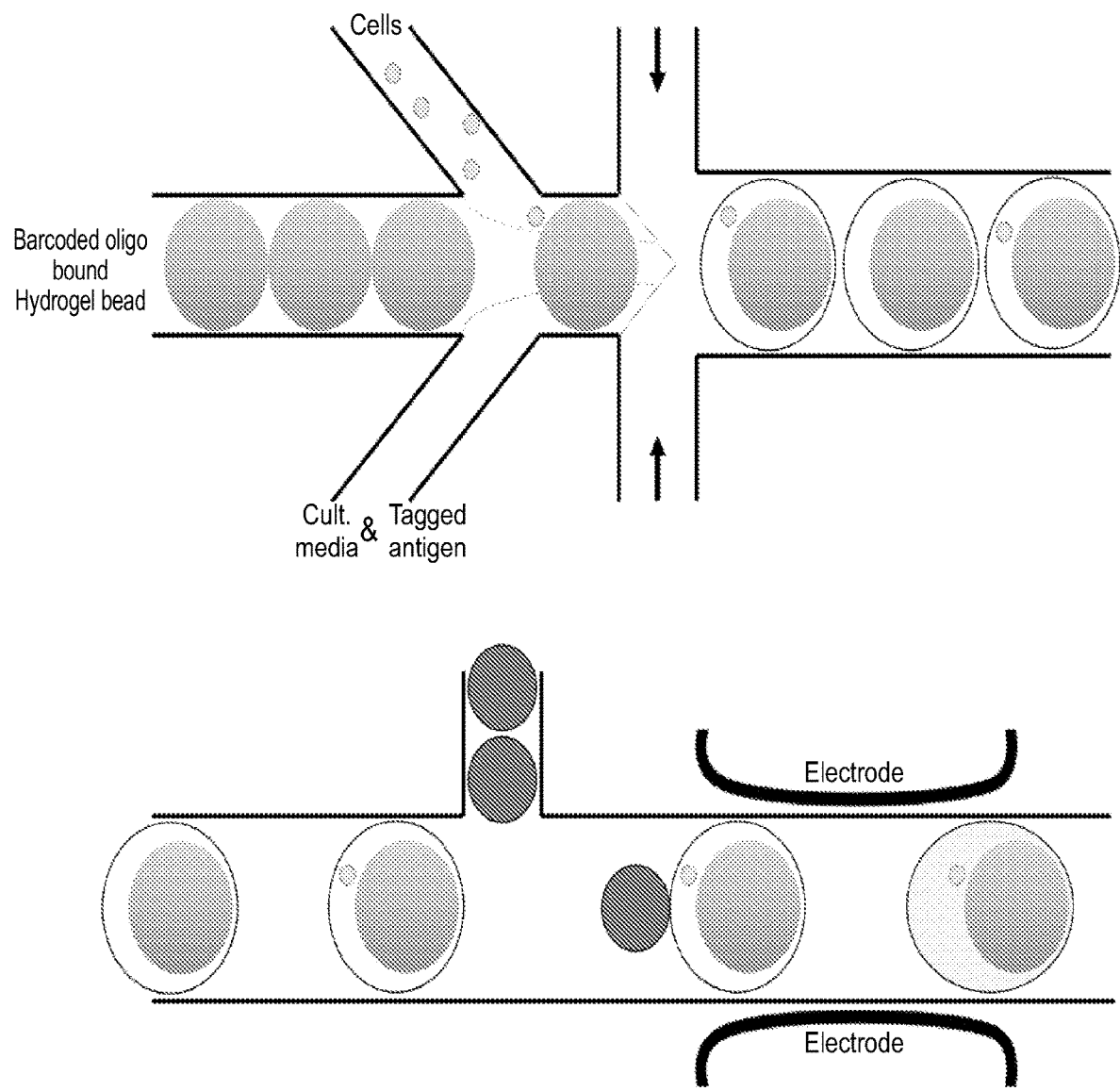
FIG. 14 is a schematic showing the encapsulation of cells and a hydrogel bead carrying a pool of partially double-stranded DNA molecules, in emulsion drops. The emulsion is re-injected in another microfluidic device where the drops are fused with other drops containing lysis buffer, RT and its buffer, a DNA polymerase, the BclI restriction enzyme. The fusion is accomplished using an electric field generated with electrodes such that when applied the two droplets merge.
Figure 15:
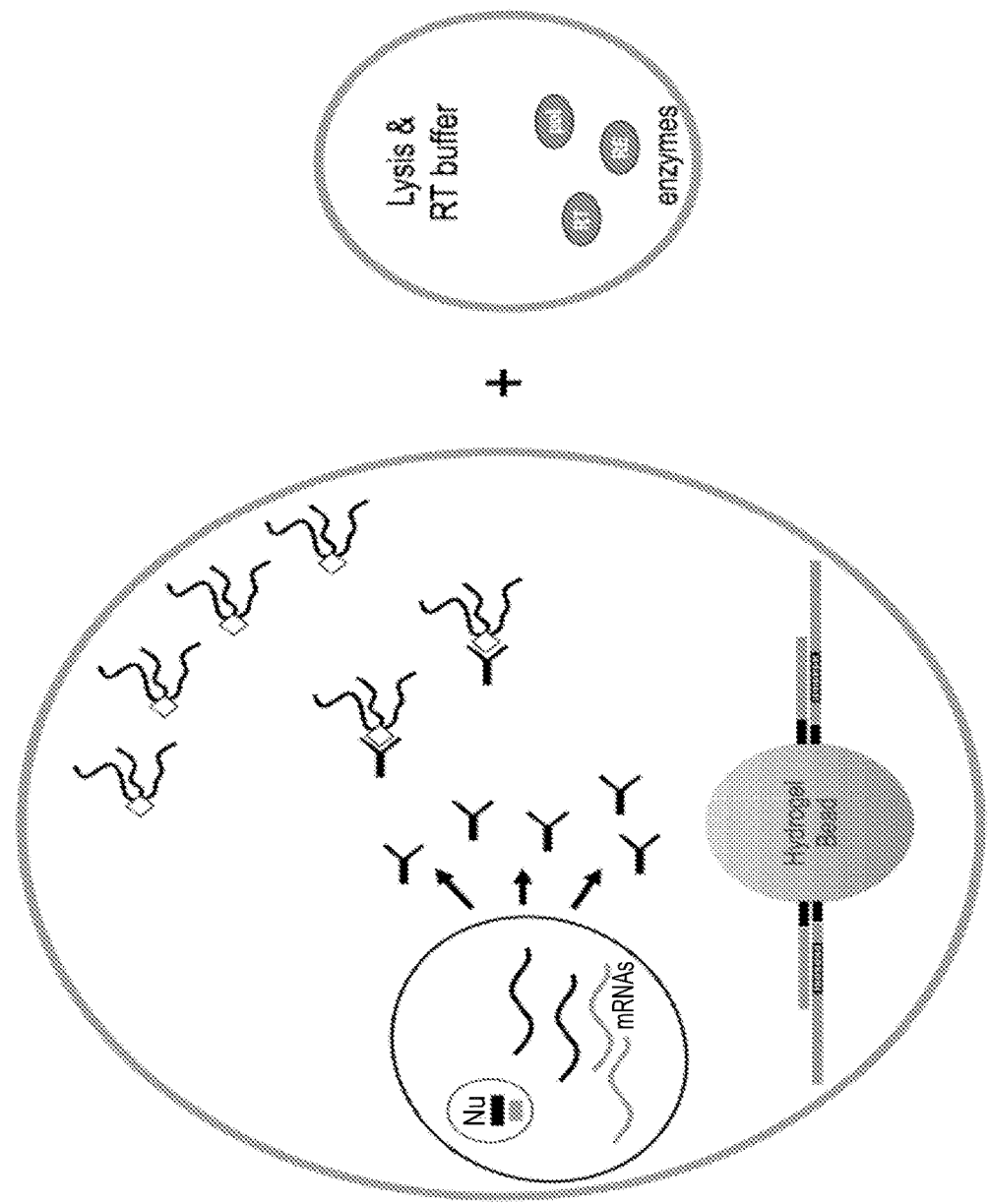
FIG. 15 is a schematic showing secretion of antibodies within the drop. The drops are then merged with RT reagents.

Coding Phenotype into DNA—DNA Polymerization and RT in Drops:

Using a microfluidic device, as described in Example 1, single cells are compartmentalized in droplets together with culture media, and single hydrogel beads carrying partially double-stranded DNA molecules, comprising a barcode that is different on each hydrogel bead. The collected emulsion is then placed at 37° C. for thirty minutes to six hours to let the cells secrete antibodies (see FIG. 14 upper panel and FIG. 15).

The emulsion is re-injected in another microfluidic device where the drops are fused with other drops containing lysis buffer, RT buffer and enzyme, DNA polymerase, and BclI restriction enzyme. The fusion is accomplished using an electric field generated with electrodes such that when applied the two droplets merge (Chabert, M., Dorfman, K., & Viovy, J. (2005). Droplet fusion by alternating current (AC) field electrocoalescence in microchannels. *Electrophoresis*, 26(19), 3706-3715. doi:10.1002/elps.200500109) (see FIG. 14 lower panel and 15).

As described in Example 1, the emulsion is then placed at 55° C. for 1 h 30 for oligo release and RT. In the same time, the antigen-bound DNA tag also anneals its complementary sequence on the single-stranded part of the released barcoded DNA and the polymerase extends the barcoded DNA molecule copying the DNA tag. Thus, barcoded cDNA of the heavy and light chains are generated via RT, and barcoded antigen-DNA tag via DNA polymerisation (see e.g. FIG. 16).

Figure 17:
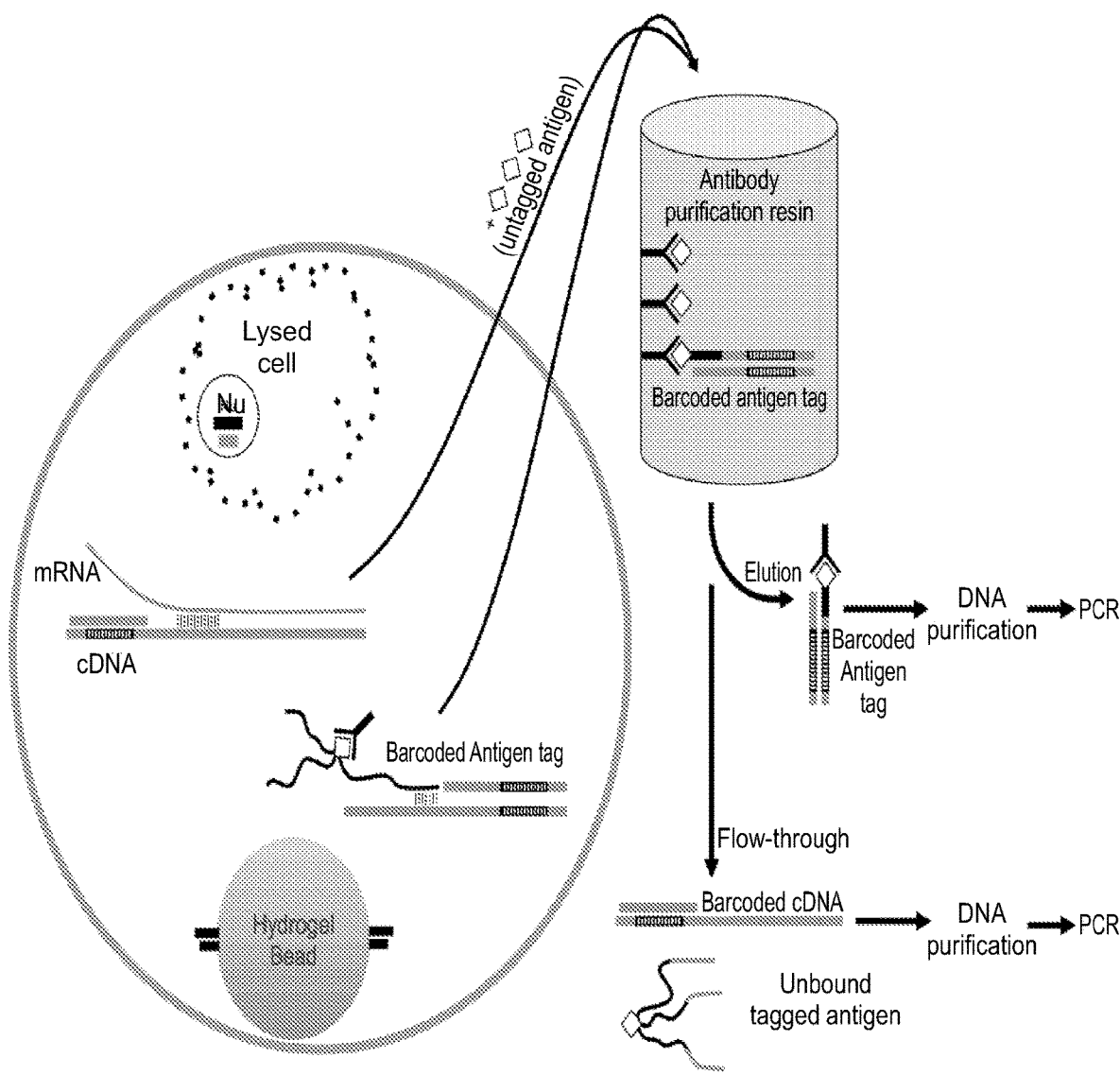
FIG. 17 is a schematic showing the purification and amplification in bulk.

Purification and Amplification in Bulk and Sequencing:

The emulsion is then placed at 70° C. to inactivate the RT enzyme. After cooling down on ice, a concentrated solution of untagged antigen is added on top of the emulsion to prevent binding of free tagged antigen (and now barcoded) from one drop to unbound antibody from another drop after emulsion breakage (FIG. 17).

The emulsion is next broken and the aqueous phase is recovered. Antibodies (bound to barcoded tagged-antigen) from this phase are purified using commercially available protein-A/G agarose resin. cDNAs are purified using commercial kits (Agencourt RNAClean XP) from the protein-A/G agarose resin flow through.

Figure 16:
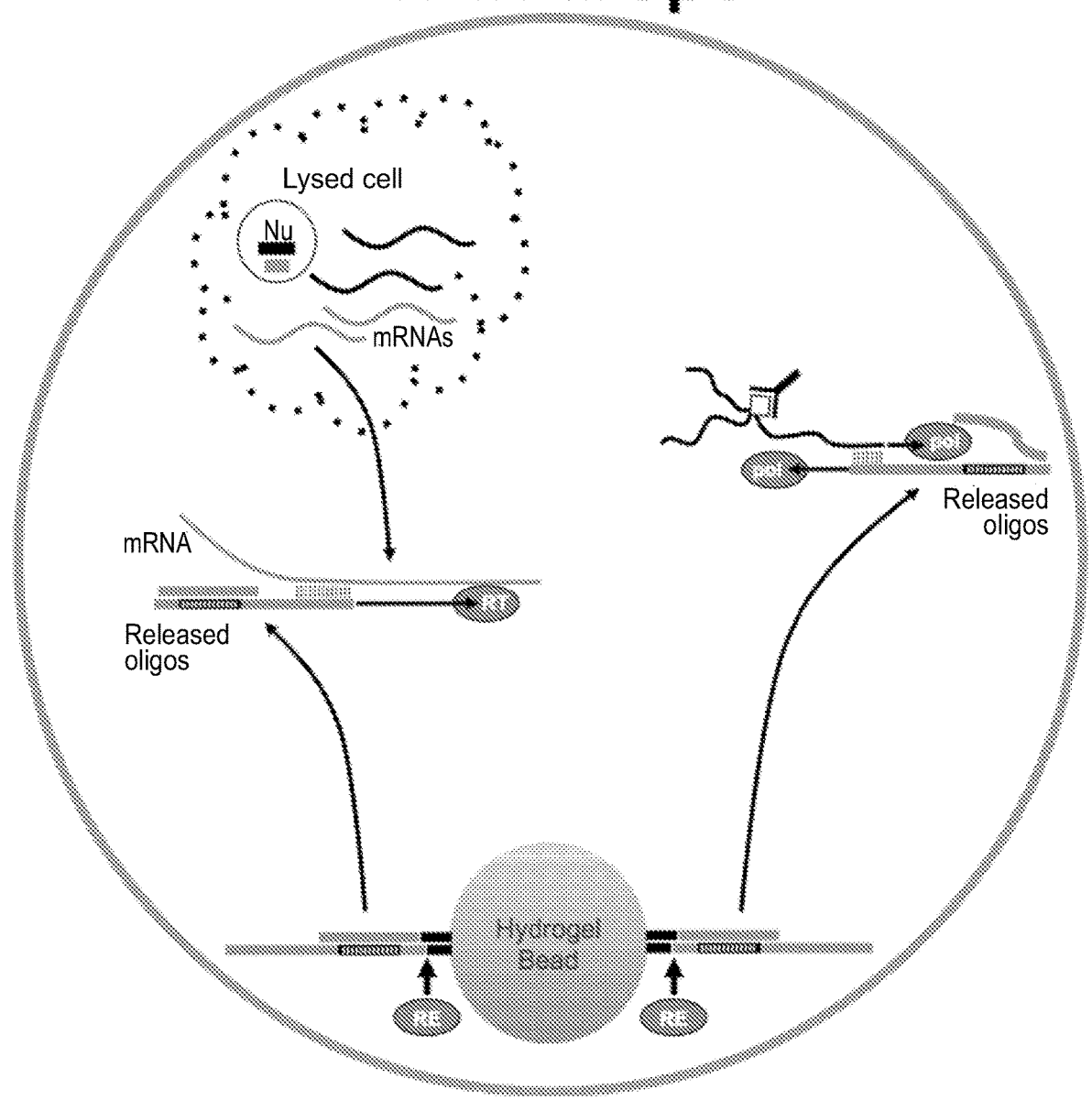
FIG. 16 is a schematic showing the results obtained from reverse transcription in emulsions drops.

Similarly to Example 1, barcoded cDNA and barcoded tags are then amplified in separate PCRs for heavy chains cDNA, light chains cDNA and DNA tags. (FIGS. 16 and 17). The primers used match the end of the cDNAs and DNA tags and have 5' extensions containing the sequences necessary for Illumina® sequencing i.e. anchoring sequences P7 (SEQ ID NO: 11)) and P5 (SEQ ID NO: 12).

Example 3

Cytometry by Sequencing

In this example, cells are incubated with DNA-tagged antibodies, washed and encapsulated with DNA polymerase, restriction enzyme BclI and a hydrogel bead caring partially single-stranded barcoded oligos (antisense of the DNA tag). The emulsion is placed at 55° C. to release the oligos and to trigger DNA polymerization (extension of the barcoded oligos copying the antibody-bound DNA tag). Sequencing then reveals all the antibodies bound to each cell, indicating the surface markers the cell displayed. In certain examples reverse transcription (RT) reagents are added to determine the sequence or transcription levels of mRNA, in which case the cells are lysed after encapsulation.

Labeling of Antibodies:

In some examples the target specific antibodies are modified by coupling to biotin, for example via an NETS-ester reaction with lysine residues, or by conjugation of a hydrazide moiety to an oxidized antibody carbohydrate residue.

Biotinylated target specific antibodies are labeled as follows (similar to Example 1 but with biotinylated antibodies instead of biotinylated antigens and adapted purification kits). An antibody is first incubated with a 10-fold excess of free streptavidin, then washed and purified using commercially available protein-A/G agarose resin. The purified streptavidin-bound antibody is then incubated with a 10-fold excess of 5' biotinylated single-stranded DNA molecules, then washed again and purified using commercially available protein-A/G agarose resin. The final product is the antibody, with its biotin tag bound by one pocket of a streptavidin molecule, and the three other pockets being occupied by 5' biotin single-stranded DNA tags.

Labeling of Cells:

Prior to compartmentalization, a population of cells is incubated with the labeled antibodies for 20 minutes then washed three times in a large volume of PBS.

Hydrogel Bead Production and Barcoded Oligonucleotide Synthesis:

Is performed as for Example 1.

Figure 18:
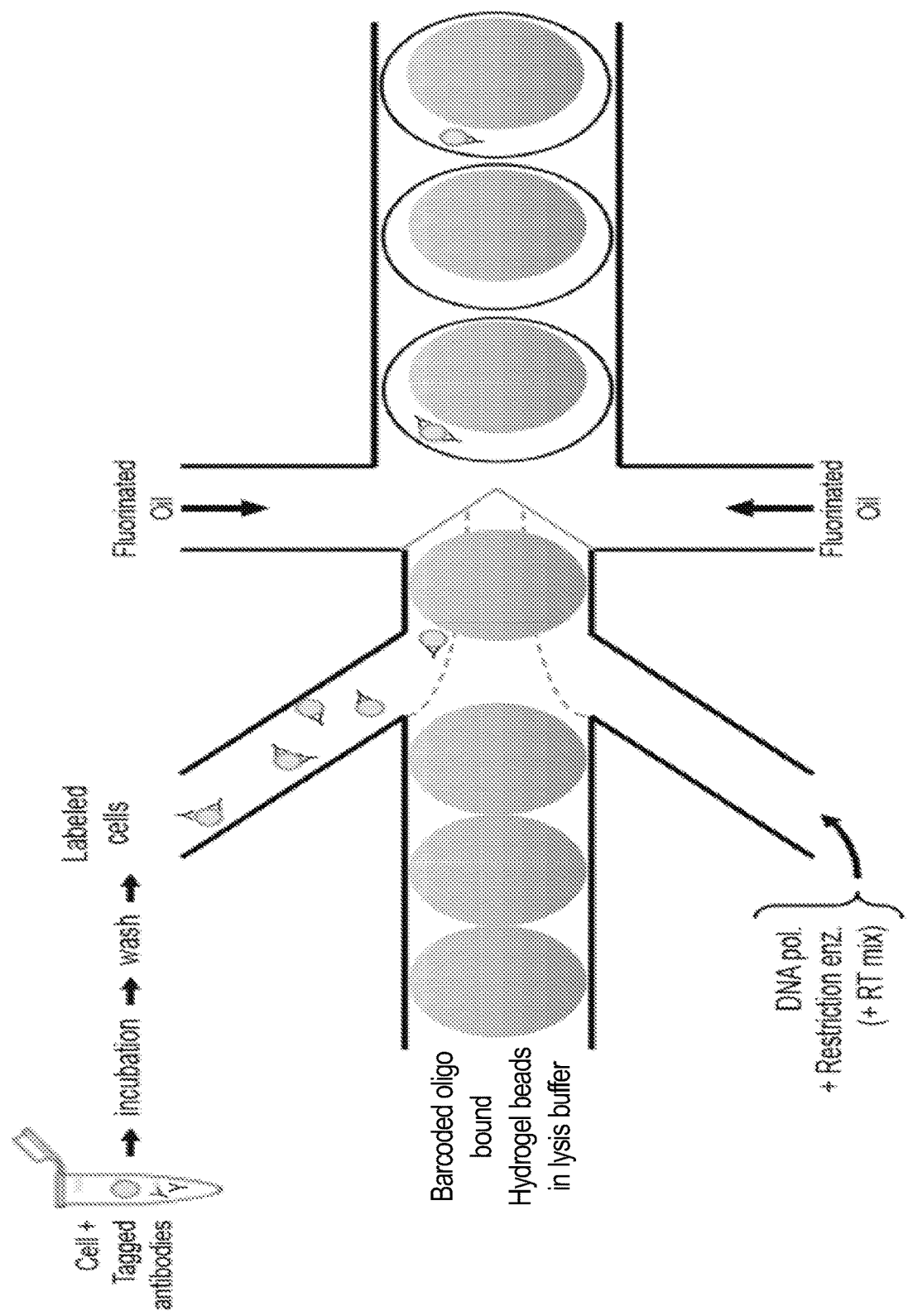
FIG. 18 is a schematic showing the microfluidic encapsulation of labeled cells together with lysis reagents, DNA polymerase, the BclI restriction enzyme and a hydrogel bead carrying a pool of partially double-stranded DNA molecules.

Coding Phenotype into DNA—DNA Polymerization and (Optional) RT in Drops:

Using a microfluidic chip, labeled cells are encapsulated in droplets together with DNA polymerase, the MI restriction enzyme and a hydrogel bead carrying a pool of partially double-stranded DNA molecules (FIG. 18). If RT is to be performed, cell lysis reagents are also added. The single-stranded part of the hydrogel bead-bound DNA consists of a UMI sequence (SEQ ID NO: 10), followed by a sequence that is antisense to the 3' end of the DNA tag.

Figure 19:
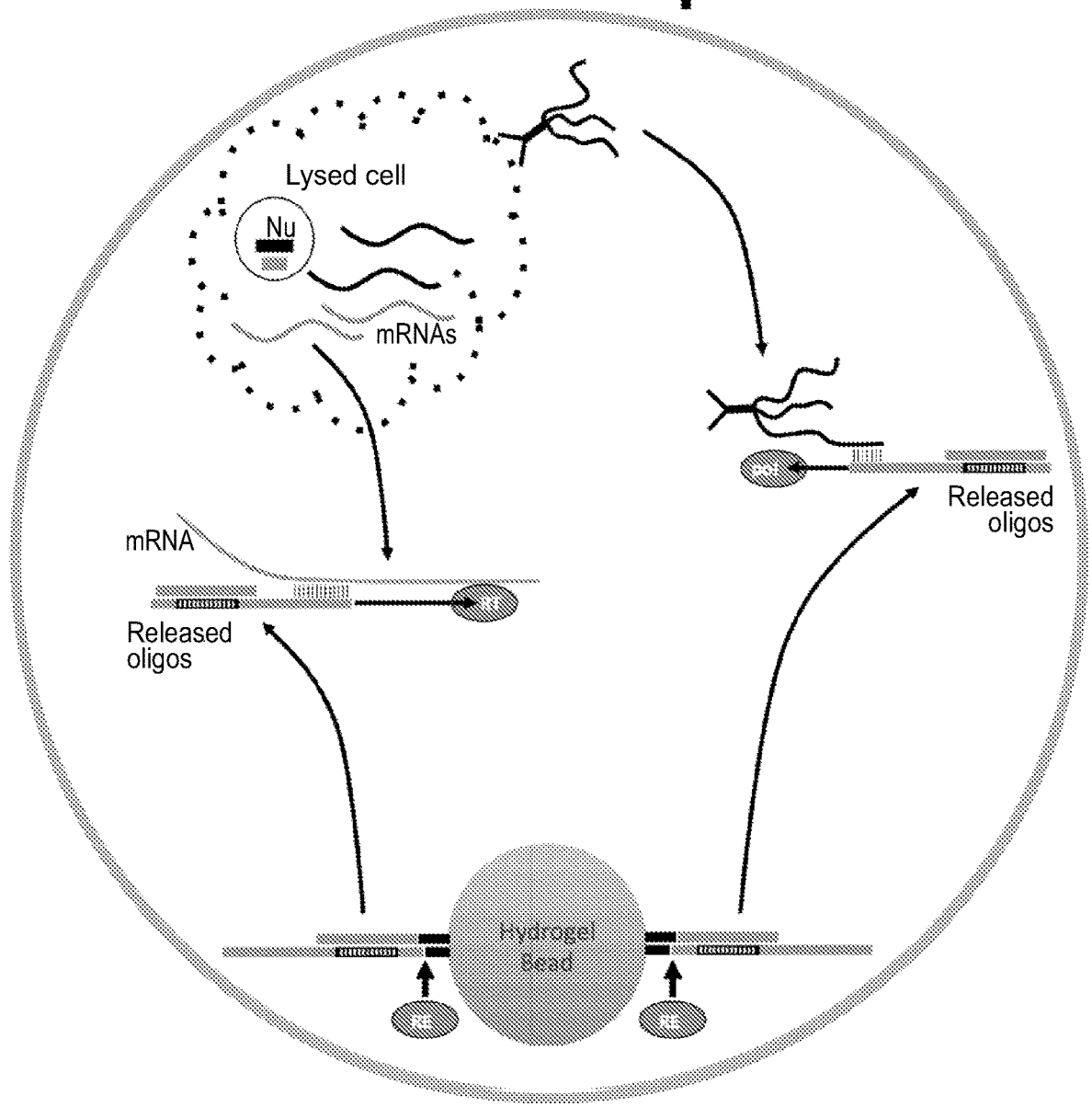
FIG. 19 is a schematic showing the results obtained from reverse transcription in emulsions drops.

The emulsion is then placed at 55° C. for 1 h 30. During this incubation, The BclI restriction enzyme is cleaved and releases the barcoded oligonucleotides into the whole volume of the drop. The antibody-bound DNA tag anneals to its complementary sequence on the single-stranded part of the hydrogel-bound barcoded DNA and the polymerase extends the barcoded DNA molecule, copying the DNA tag (FIG. 19). The DNA barcode link to the antibody DNA tags gives single cell specificity to these sequences.

In case of RT, part of the hydrogel bead-bound oligo pool is complementary to mRNAs and the cell is lysed by incubation at 55° C., to release the mRNA which anneals to the complementary sequences on the single-stranded part of the released barcoded oligonucleotides, and the RT enzyme extends the barcoded DNA, copying the sequence of the mRNA.

Purification and Amplification in Bulk and Sequencing:

The emulsion is then placed at 70° C. to inactivate the RT enzyme. After cooling down on ice, the emulsion is broken and the aqueous phase is recovered and DNA purified using commercial kits (Agencourt RNAClean XP).

Figure 20:
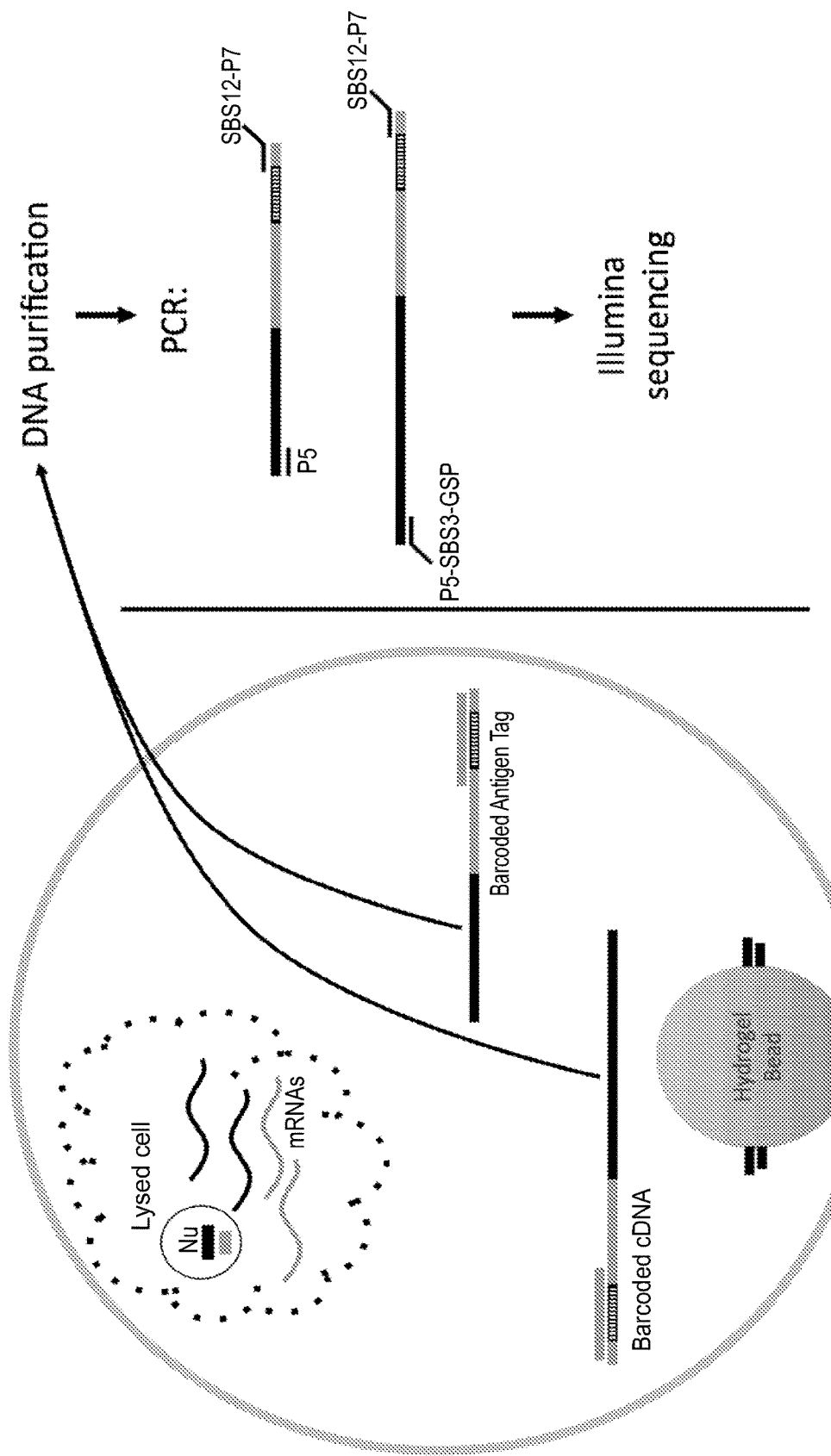
FIG. 20 is a schematic showing the purification and amplification in bulk.

Barcoded tags (and cDNA in case of RT) are then amplified by PCR. The primers used match the end of the tags and have 5' extensions containing the sequences necessary for Illumina® sequencing i.e. anchoring sequences P7 (SEQ ID NO: 11) and P5 (SEQ ID NO: 12) (FIG. 20).

Example 4

Protein Phosphorylation Assay

In this example, the target molecules are proteins that undergo phosphorylation post translational modifications. e.g., the tyrosine kinases Epidermal growth factor receptor (EGFR) and Janus kinase 2 (JAK2), and the downstream, kinase phosphorylated transcription factor, signal transducer and activator of transcription 3 (STAT3). This example provides a method for measuring protein phosphorylation levels.

Figure 21:
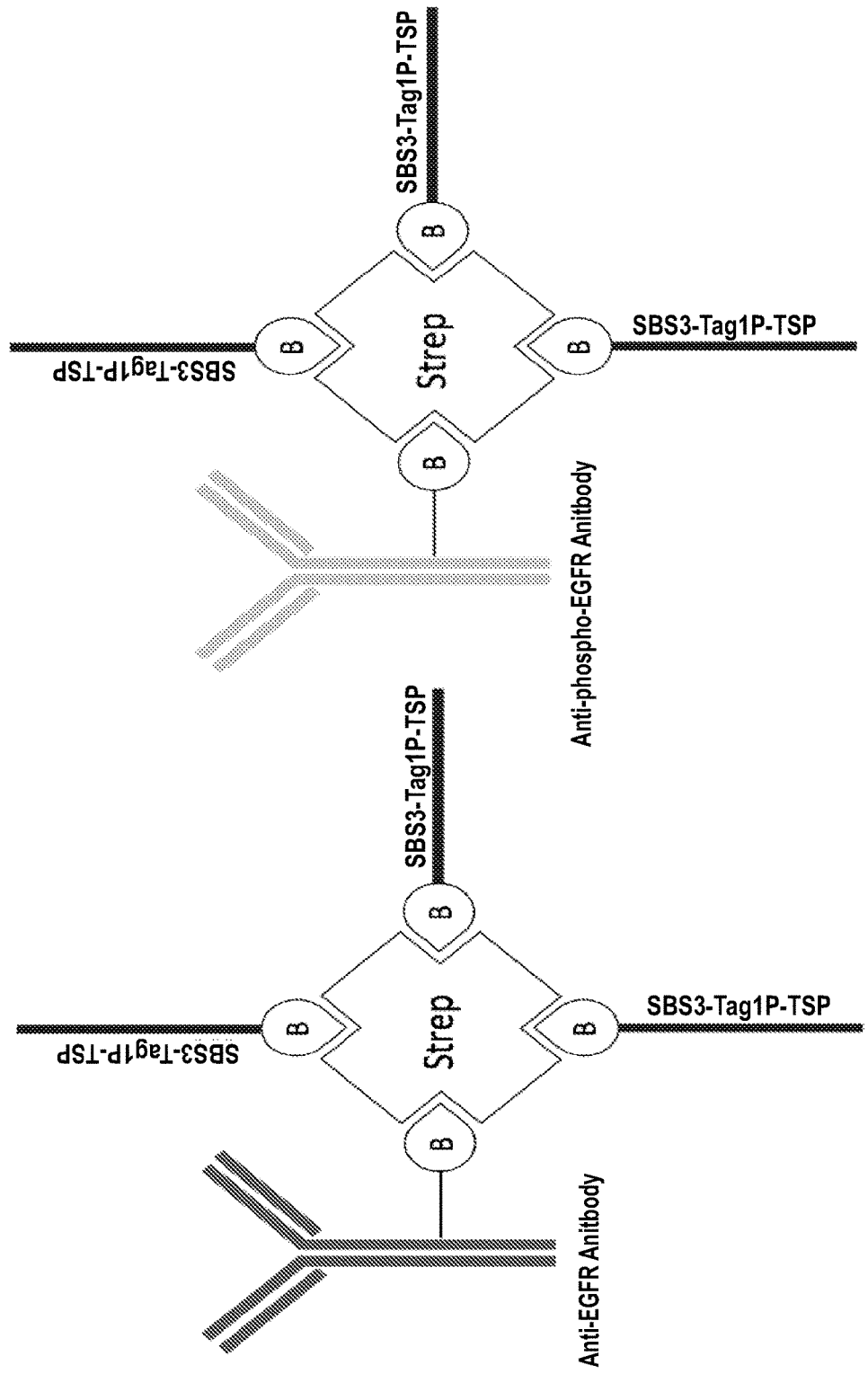
FIG. 21 is a schematic of a labeled antibody structure.

Antibodies specific to the different target proteins are labeled with different single-stranded DNA tags (FIG. 21). Cells of interest are incubated in appropriate media, with or without test agents, such as pharmaceutical agents or potential pharmaceutical agents. The cells are then washed, and encapsulated in ~100 pL droplets with the DNA tag labelled target specific antibodies, lysis buffer, PCR buffer and enzymes (DNA polymerase and restriction enzyme MI), biotin labeled antibodies specific to target domains lacking phosphorylation sites, and a hydrogel bead (Abate, A. R. et al. (2009)) carrying a mix of barcoded-primers complementary to the DNA tags of the DNA tag labeled target specific antibodies, using a microfluidic device.

Labeling of Antibodies:

The DNA tags are created as in Example 1. However, any suitable plasmid may be used for tag generation, and the 5' extension which is common to all antibody tags (SEQ ID NO: 3) is referred to as the tag specific primer (TSP). Different tags, such as the three required for this example, are made by amplifying different regions of a plasmid.

The target specific antibodies may be commercially available already conjugated with biotin, or may be modified with biotin via an NETS-ester reaction with lysine residues, or by conjugation of a hydrazide moiety to an oxidized antibody carbohydrate residue. Biotinylated target specific antibodies are labelled with DNA tags as in Example 1.

The final product is the antibody, with its biotin tag bound by one pocket of a streptavidin molecule, and the three other pockets being occupied by 5' biotin single-stranded DNA tags. The labelled target specific antibodies are mixed in equal ratios before use in the assay.

Hydrogel Bead Production and Barcoded Oligonucleotide Synthesis:

This is performed as in Example 1, with this example's UMIs differentiating between sequences originating from different DNA tagged target specific antibodies, rather than from different RT priming events.

Coding Phenotype into DNA—DNA Polymerization in Drops:

The DNA tag labelled target specific antibodies are specific to the phosphorylation region of the target proteins. One antibody against the phosphorylated protein and one against the non-phosphorylated are used to encode specific tags for each state. A third antibody, specific to a domain of the protein that does not contain a phosphorylation site, is used to label the bound complexes. This antibody is labeled with biotin, using the methods from the "Labeling of antibodiese" section of this example. This antibody does not have a DNA tag, and is encapsulated in all droplets. The biotin label allows later separation of antibody-target complexes from unbound antibodies. Alternatively, the complexes can be purified by size exclusion chromatography, without the use of the third antibody.

Figure 22:
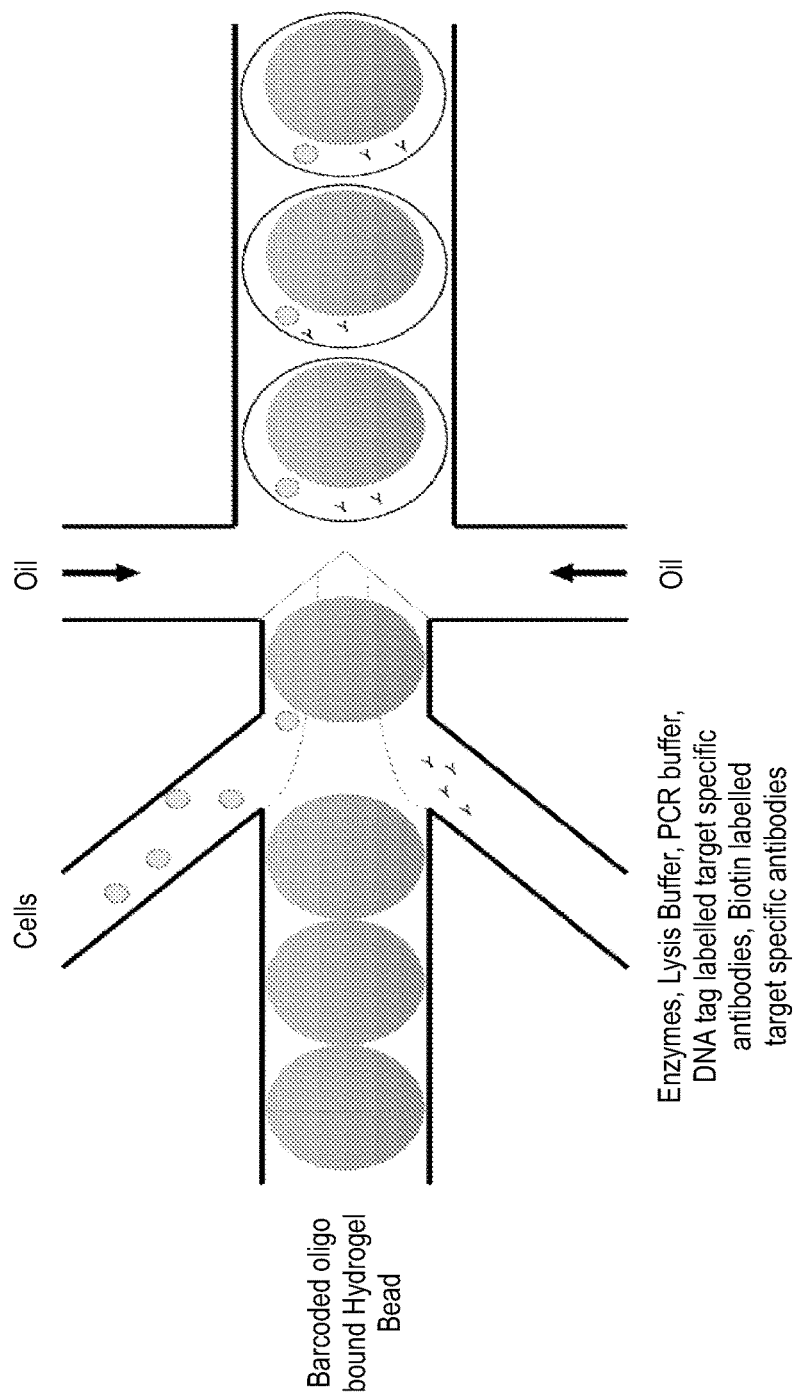
FIG. 22 is a schematic showing the microfluidic encapsulation of single cells together with the DNA tag labelled target specific antibodies, lysis buffer, a DNA polymerase (New England BioLabs Klenow Fragment (3'→5' exo-)) and its buffer, the MI restriction enzyme, biotin labeled antibodies, and a hydrogel bead carrying a pool of partially double-stranded DNA molecules, all of them sharing the same 96 base pair DNA barcode; this DNA barcode is different on every hydrogel bead.

Using a microfluidic chip, single cells are encapsulated in droplets together with the DNA tag labelled target specific antibodies, lysis buffer, a DNA polymerase (New England BioLabsBiolabs Klenow Fragment (3'→5' exo-)) and its buffer, the BclI restriction enzyme, biotin labelled antibodies as described above, and a hydrogel bead carrying a pool of partially double-stranded DNA molecules, all of them sharing the same DNA barcode; this DNA barcode is different on every hydrogel bead. Drops are produced with a Poisson distribution for cell encapsulation, and cell concentration is chosen such that the mean number of cells per droplet <1, ensuring that the majority of the drops contain no more than one cell. The deformable hydrogel beads are injected as a closed packed array (Abate, A. R. et al. (2009)), ensuring that most drops contain a single bead (FIG. 22). The single-stranded part of the hydrogel bead-bound DNA molecules consists of a UMI sequence, followed by a sequence that is antisense to the 3' end of the DNA tag.

Figure 23:
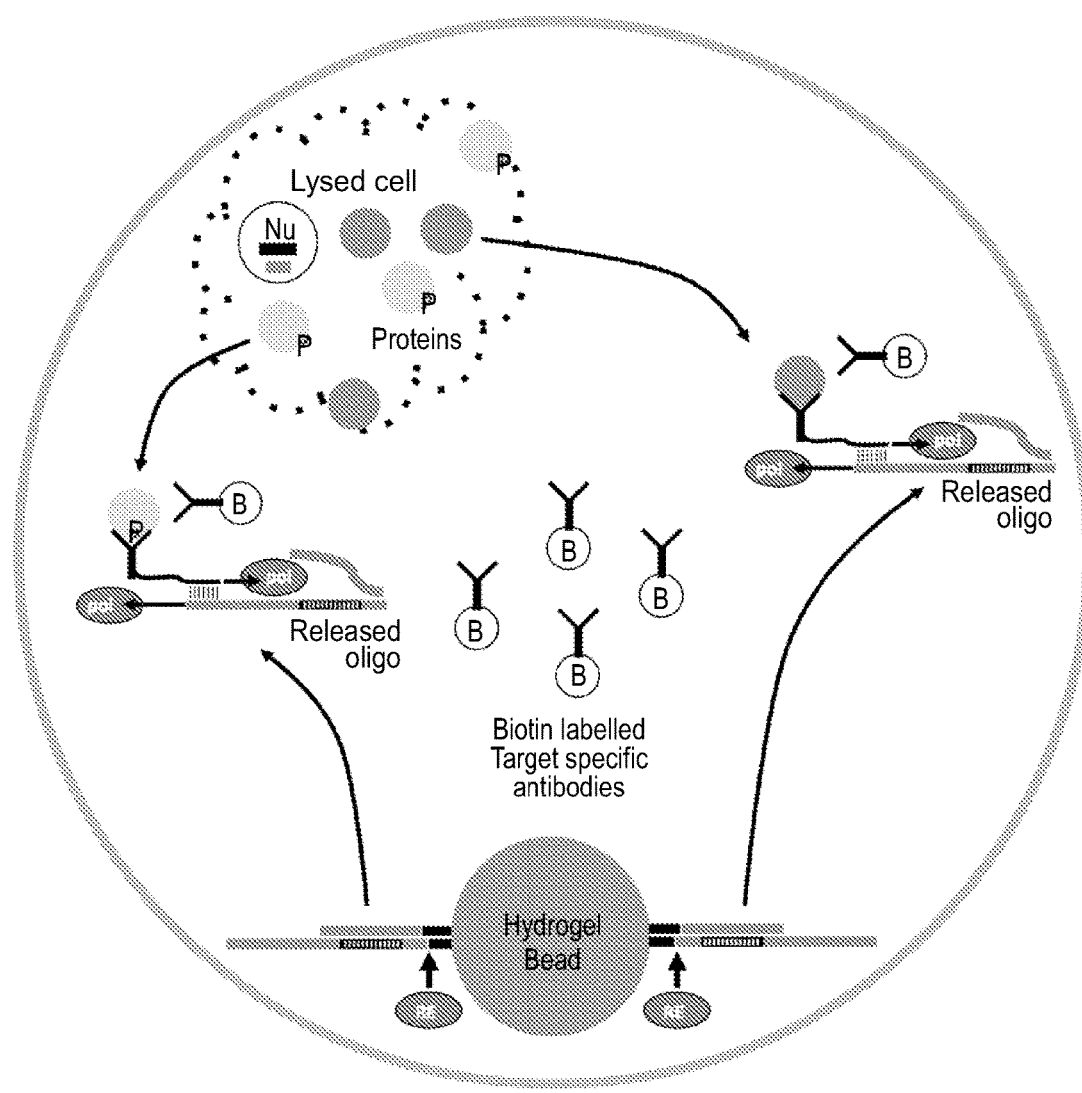
FIG. 23 is a schematic showing MI restriction enzyme cleavage and release of the barcoded oligonucleotides into the whole volume of the drop. At the same time, the cell lyse and the released target proteins will be captured by the labeled antibodies, which will anneal their complementary sequence on the single-stranded part of the hydrogel-bound barcoded DNA and the polymerase will extend the barcoded DNA molecule, copying the DNA tag. These antibody-target complexes are captured by the biotin labelled antibodies. The addition of the DNA barcode to the antibody bound DNA tags gives single cell specificity to these sequences.

The emulsion is then placed at 37° C. for 1 h 30. During this incubation the BclI restriction enzyme cleaves and releases the barcoded oligonucleotides into the whole volume of the drop. At the same time, the cell lyses and the released target proteins are captured by the labeled antibodies, which anneal to their complementary sequence on the single-stranded part of the hydrogel-bound barcoded DNA and the polymerase extends the barcoded DNA molecule, copying the DNA tag. These antibody-target complexes are captured by the biotin labelled antibodies. The addition of the DNA barcode to the antibody bound DNA tags gives single cell specificity to these sequences (FIG. 23).

Figure 24:
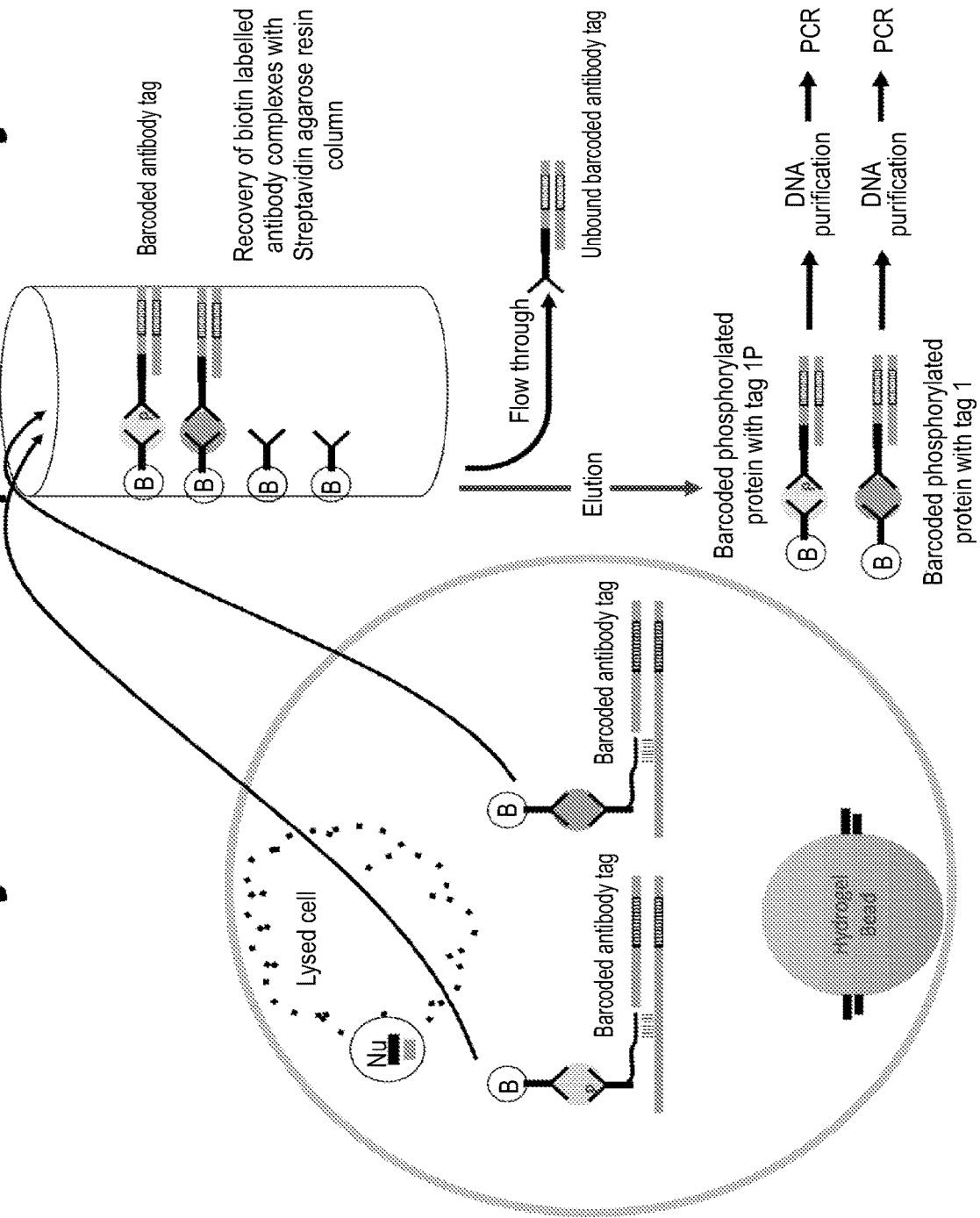
FIG. 24 is a schematic showing the recovery, and separation of phosphorylated from non-phosphorylated target proteins.

Recovery, and Separation of Phosphorylated from Non-Phosphorylated Target Proteins:

The emulsion is placed at 75° C. to inactivate the polymerase enzyme, then the emulsion is broken and the aqueous phase is recovered. Phosphorylated and non-phosphorylated proteins, together with attached antibodies, DNA tags, and barcodes, are then separated via streptavidin agarose columns (Pierce® Streptavidin Agarose Columns) from unbound DNA tag labeled antibodies (FIG. 24). Alternatively, the complexes can be purified by size exclusion chromatography.

Amplification in Bulk and Sequencing:

The barcoded DNA tags are purified using commercial kits (Agencourt AMPure XP). Barcoded tags are then amplified in separated PCR for tags from phosphorylated and non-phosphorylated proteins. The primers used match the end of the DNA tags, and have 5' extensions containing the sequences necessary for Illumina® sequencing i.e. the anchoring sequences P7 (SEQ ID NO: 11) and P5 (SEQ ID NO: 12).

Single cell level target protein phosphorylation data is to be quantified, and compared with total target protein quantities, via the number of target specific DNA tag reads for each DNA barcode or the number of UMIs.

Example 5

Alternate Protein Phosphorylation Assay

In this example, the target molecules are proteins that undergo phosphorylation post translational modifications. e.g., the tyrosine kinases Epidermal growth factor receptor (EGFR) and Janus kinase 2 (JAK2), and the downstream, kinase phosphorylated transcription factor, signal transducer and activator of transcription 3 (STAT3). This example provides a method for measuring protein phosphorylation levels.

Antibodies specific to the different target proteins are labeled with different double-stranded DNA tags (FIG. 25). Cells of interest are incubated in appropriate media, with or without test agents, such as pharmaceutical agents or potential pharmaceutical agents. The cells are then washed, and encapsulated in ~100 pL droplets with lysis buffer, restriction enzyme BclI, biotin labelled antibodies specific to target domains lacking phosphorylation sites, and a hydrogel bead (Abate, A. R. et al. (2009)) carrying barcoded-primers which are ligated to the DNA tags of the DNA tag labelled target specific antibodies, using a microfluidic device. Labeling of antibodies:

The DNA tag is created by annealing two commercially produced oligonucleotides with the following descriptions. One has a phosphate terminated 4 nucleotide (nt) 5' extension, followed a 30 nt random sequence, then the Illumina® SBS3 sequence (SEQ ID NO: 2), and a 10 nt random sequence. This 4 nt overhang is common to all tags, and allows ligation of the tags to barcoded hydrogel beads. The reverse sequence is terminated at the 5' end by an amino, aldehyde, or NETS-ester modifier depending on the method used to conjugate the tags to antibodies, and has a 10 nt 5' single strand overhang as a flexible linker. Different DNA tags can be generated by this same scheme by changing the 30 nt random sequence. Their sequences will be identical over the nucleotides at both extremities, but the center will be different, providing different tags for different target antibodies.

The annealed, doubled-stranded DNA tags are then conjugated to the target specific antibodies as follows. After Kozlov et al. (Kozlov, I. A. et al.—Efficient strategies for the conjugation of oligonucleotides to antibodies enabling highly sensitive protein detection. *Biopolymers* (2004). 73(5), 621-630. doi:10.1002/bip.20009)), tags with a 5' 4 nt single-stranded overhang, and an aldehyde 5' modification (on the reverse sequence) are conjugated to antibodies via the formation of a hydrazone bond. Antibodies are first incubated in PBS with a 20-fold excess of succinimidyl 4-hydrazinonicotinate acetone hydrazone (SANH; Solulink). They are then purified by size exclusion chromatography in an Illustra NAP-5 column (GE Healthcare), and resuspended in 100 mM citrate buffer at pH 6.0. The antibodies are then incubated with a 10-fold excess of the DNA tag, and again purified by the Illustra (GE Healthcare) size exclusion columns.

The final product is the antibody bound to 5' aldehyde double-stranded DNA tags. The labelled target specific antibodies are mixed in equal ratios before use in the assay.

Hydrogel Bead Production and Barcoded Oligonucleotide Synthesis:

This is performed as in Example 1. However, the last duplex ligated to the newly synthetized barcode is terminated by a 4 nt 5' overhang. This overhang is complementary to the 5' 4 nt overhang common to all target specific DNA tags, allowing their ligation by the T7 DNA ligase to the hydrogel beads. Additionally, UMIs are used to differentiate between sequences originating from different DNA tagged target specific antibodies, rather than from different RT priming events.

Coding Phenotype into DNA:

The hydrogel beads carry a pool of partially double-stranded DNA molecules, all of them sharing the same DNA barcode; this DNA barcode is different on every hydrogel bead, and terminates with a 4 nt 5' overhang. Prior to use in the assay, the DNA tag-labeled antibodies are ligated to the hydrogel beads via a T7 ligase enzyme. This links the target specific tag sequences with the hydrogel bead barcodes. This ligation of DNA tag to DNA barcode gives single cell specificity to the target molecules.

These labeled antibodies are specific to the phosphorylation region of the target proteins. One antibody against the phosphorylated protein and one against the non-phosphorylated are used to encode specific tags for each state. A third antibody, specific to a domain of the protein that does not contain a phosphorylation site, is used to label the bound complexes. This antibody is labeled with biotin, using the methods from the "Labeling of target antibodies" section of Example 4. This antibody does not have a DNA tag, and is encapsulated in all droplets. The biotin label allows later separation of antibody-target complexes from unbound antibodies. Alternatively, the complexes can be purified by size exclusion chromatography, without the use of the third antibody.

Figure 26:
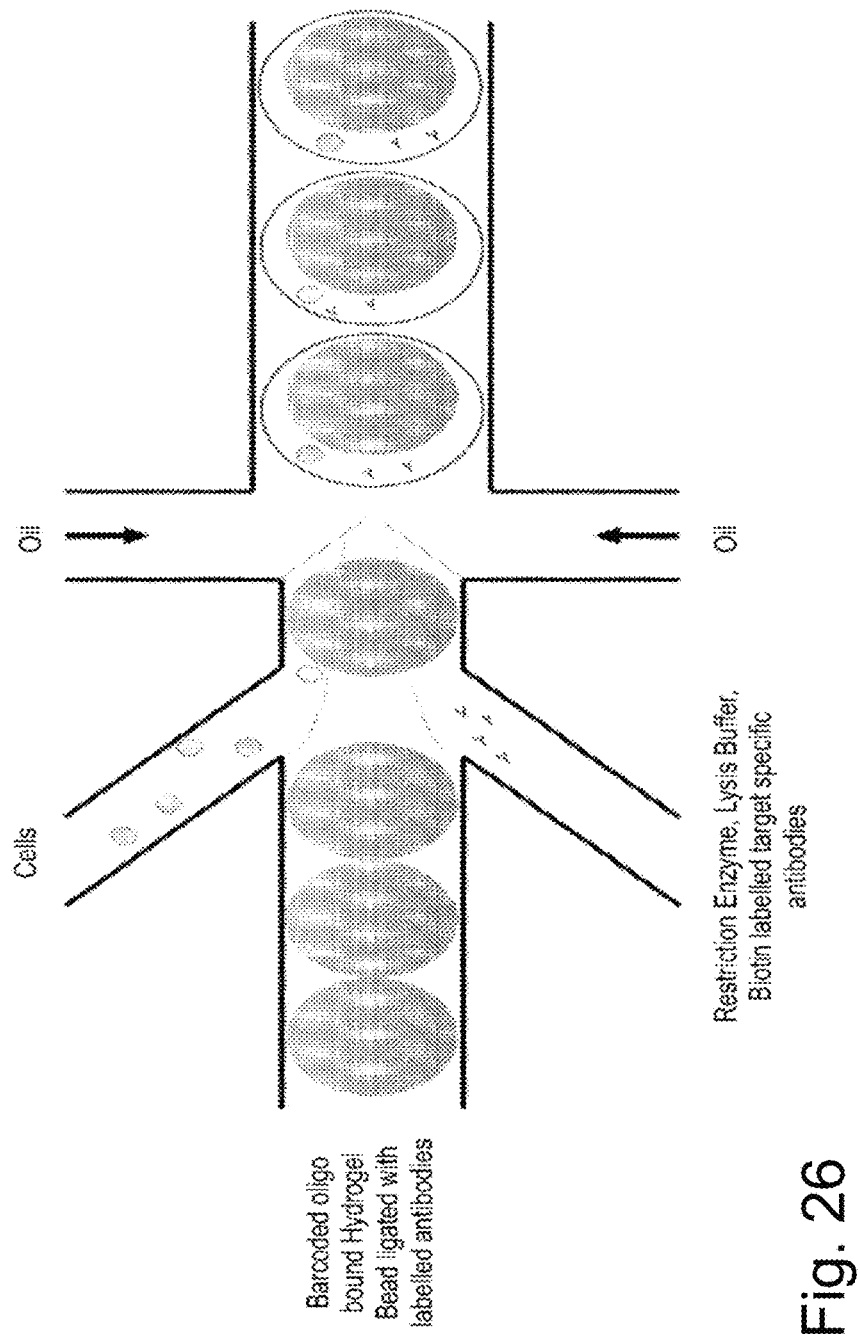
FIG. 26 is a schematic showing the microfluidic encapsulation of single cells together with lysis buffer, the MI restriction enzyme, biotin labeled antibodies, and a hydrogel bead carrying the DNA barcode, which is ligated to the DNA tag labeled antibodies.

Using a microfluidic chip, single cells are encapsulated in droplets together with lysis buffer, the BclI restriction enzyme, biotin labeled antibodies as described above, and a hydrogel bead carrying the DNA barcode, which is ligated to the DNA tag labelled antibodies. Drops are produced with a Poisson distribution for cell encapsulation, and cell concentration is chosen such that the mean number of cells per droplet <1, ensuring that the majority of the drops contain no more than one cell. The deformable hydrogel beads are injected as a closed packed array (Abate, A. R. et al. (2009), ensuring that most drops contain a single bead (FIG. 26).

Figure 27:
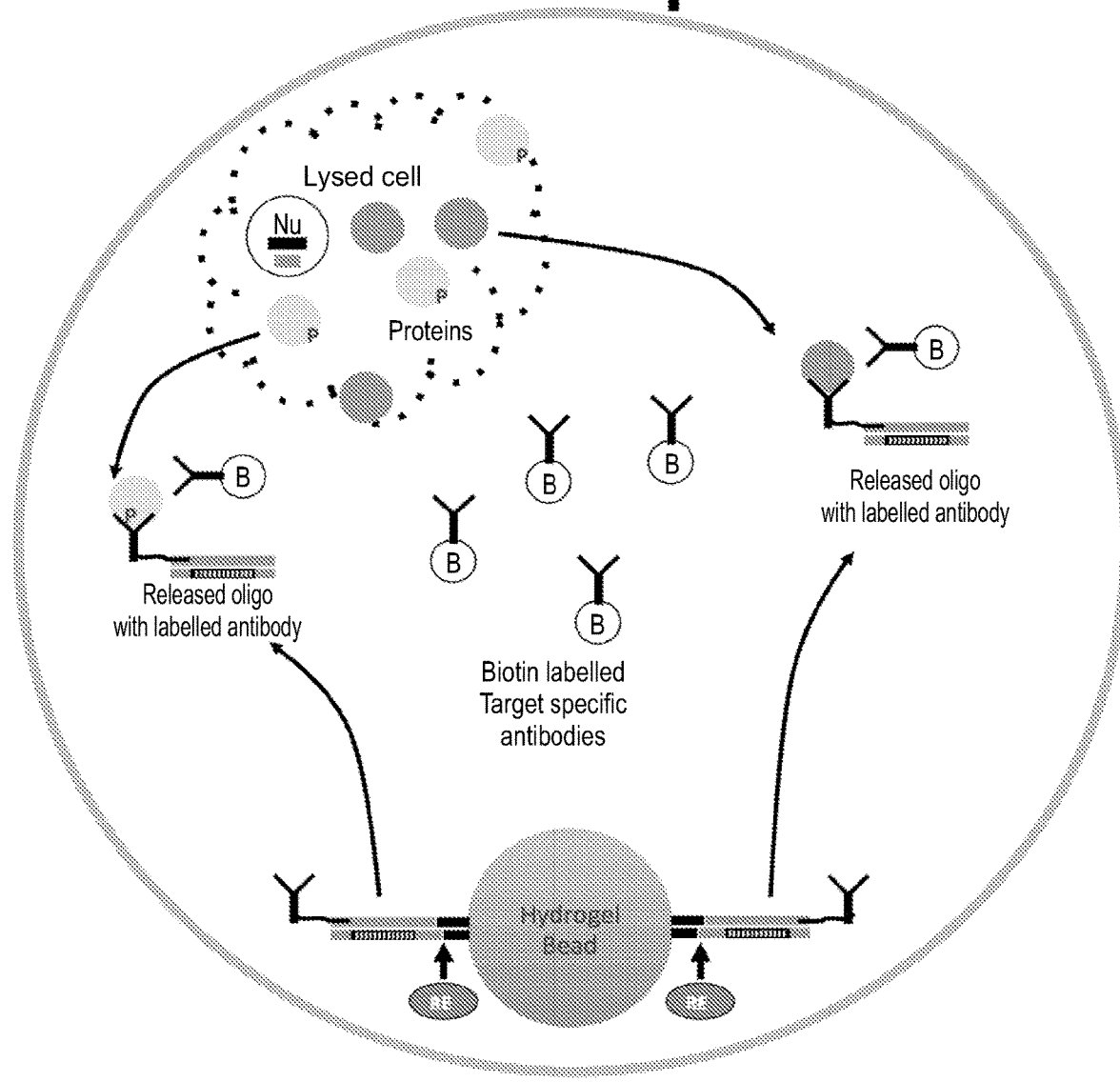
FIG. 27 is a schematic showing protein capture.

The emulsion is then placed at 37° C. for 1 h 30. During this incubation the BclI restriction enzyme is cleaved and releases the barcoded and labeled antibodies into the whole volume of the drop. At the same time, the cells lyse and the released target proteins are captured by these antibodies. These antibody-target complexes are captured by the biotin labeled antibodies (FIG. 27).

Figure 28:
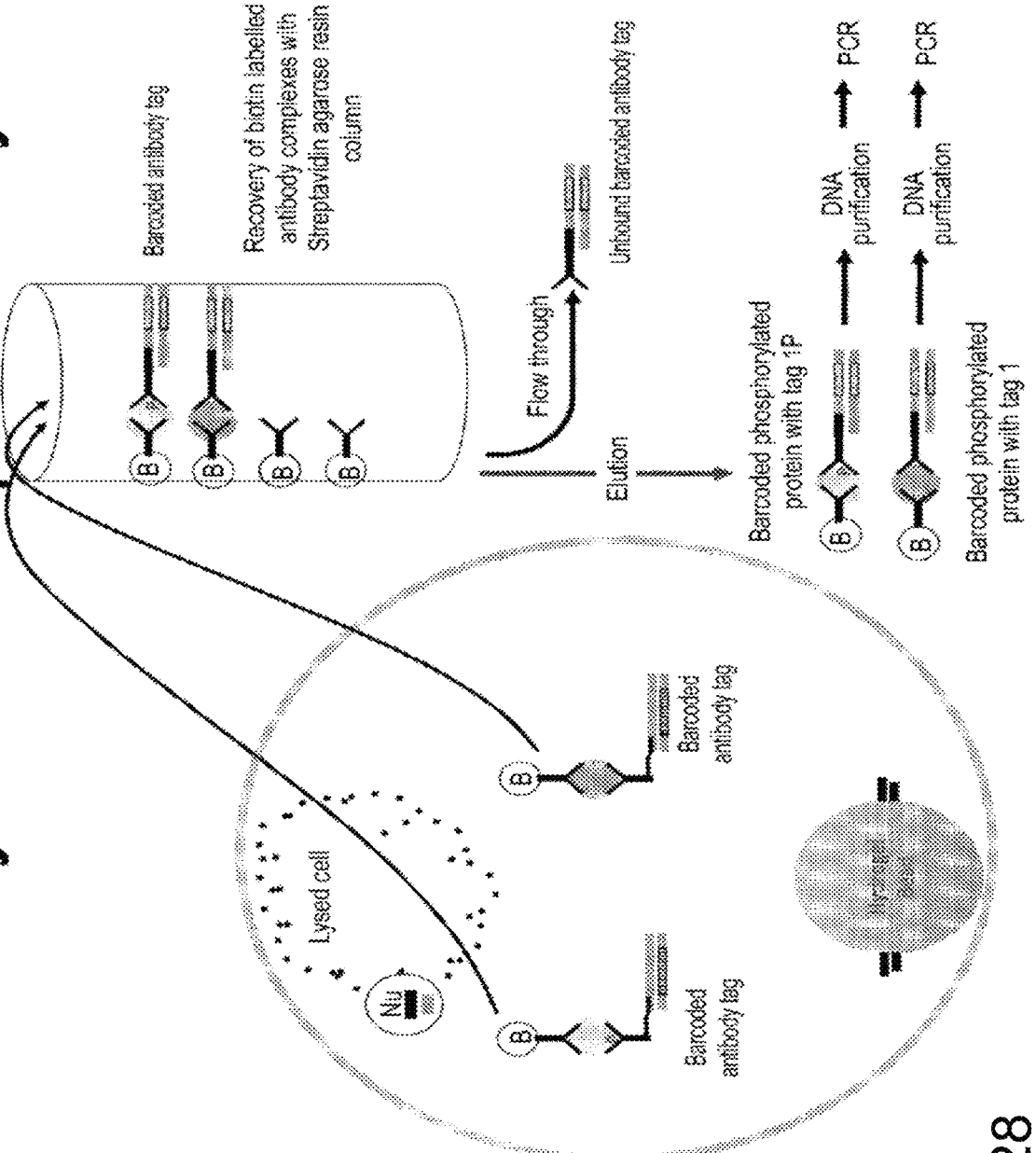
FIG. 28 is a schematic showing antibody-protein complex recovery.

Recovery, and Separation of Phosphorylated from Non-Phosphorylated Target Proteins:

The emulsion is broken and the aqueous phase is recovered. Phosphorylated and non-phosphorylated proteins, together with attached antibodies, DNA tags, and barcodes, are then separated via streptavidin agarose columns (Pierce® Streptavidin Agarose Columns) from unbound DNA tag labeled antibodies (FIG. 28). Alternatively, the complexes can be purified by size exclusion chromatography.

Amplification in Bulk and Sequencing:

The barcoded DNA tags are purified using commercial kits (Agencourt AMPure XP). Barcoded tags are then amplified in separated PCR for tags from phosphorylated and non-phosphorylated proteins. The primers used match the end of the DNA tags, and have 5' extensions containing the sequences necessary for Illumina® sequencing i.e. the anchoring sequences P7 (SEQ ID NO: 11) and P5 (SEQ ID NO: 12).

Single cell level target protein phosphorylation data is to be quantified, and compared with total target protein quantities, via the number of target specific DNA tag reads for each DNA barcode or the number of UMIs.

Example 6

Alternate Protein Phosphorylation Assay

In this example, the target molecules are proteins that undergo phosphorylation post translational modifications. e.g., the tyrosine kinases Epidermal growth factor receptor (EGFR) and Janus kinase 2 (JAK2), and the downstream, kinase phosphorylated transcription factor, Signal transducer and activator of transcription 3 (STAT3). This example provides a method for simultaneously measuring protein phosphorylation levels, and targeted sequencing of mRNA for determination of target sequence and degree of expression.

Antibodies specific to the different target proteins are labeled with different single-stranded DNA tags. Cells of interest are incubated in appropriate media, with or without test agents, such as pharmaceutical agents or potential pharmaceutical agents. The cells are then washed, and encapsulated in ~100 pL droplets with the DNA tag labelled target specific antibodies, reverse-transcription buffer and enzymes (reverse transcriptase, DNA polymerase and restriction enzyme BclI biotin labelled antibodies specific to target domains lacking phosphorylation sites, and a hydrogel bead (Abate, A. R. et al. (2009)) carrying a mix of barcoded-primers complementary to the DNA tags of the labelled target specific antibodies and to the targeted mRNA, using a microfluidic device.

Labeling of antibodieThe DNA tags are created as in Example 4.

Hydrogel Bead Production and Barcoded Oligonucleotide Synthesis:

This is performed as for Example 1, with this example's UMIs differentiating between sequences originating from different DNA tagged target specific antibodies, and from different RT priming events.

Coding Phenotype into DNA—DNA Polymerization and RT in Drops:

The DNA tag labelled target specific antibodies are specific to the phosphorylation region of the target proteins. One antibody against the phosphorylated protein and one against the non-phosphorylated are used to encode specific tags for each state (see e.g. FIG. 29). A third antibody, specific to a domain of the protein that does not contain a phosphorylation site, is used to label the bound complexes. This antibody is labeled with biotin, using the methods from the "Labeling of target molecule" section of Example 4. This antibody does not have a DNA tag, and is encapsulated in all droplets. The biotin label allows later separation of antibody-target complexes from unbound antibodies. Alternatively, the complexes can be purified by size exclusion chromatography, without the use of the third antibody.

Figure 29:
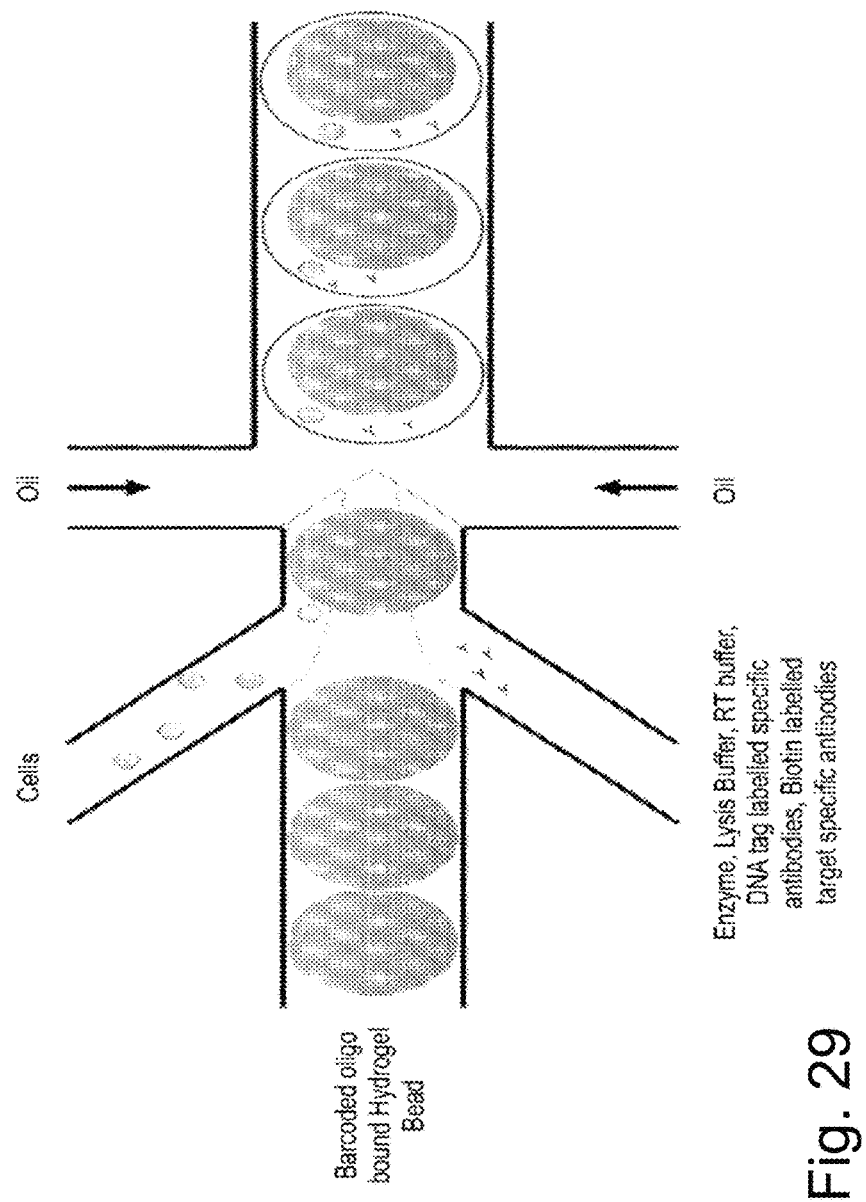
FIG. 29 is a schematic showing the microfluidic encapsulation of single cells together with the DNA tag labeled target specific antibodies, lysis buffer, reverse transcription enzyme and its buffer, a DNA polymerase, the BclI restriction enzyme, biotin labeled antibodies as described above, and a hydrogel bead carrying a pool of partially double-stranded DNA molecules, all of them sharing the same 96 base pair DNA barcode; this DNA barcode is different on every hydrogel bead.

Using a microfluidic chip, single cells are encapsulated in droplets together with the DNA tag labelled target specific antibodies, lysis buffer, reverse transcription enzyme and its buffer, a DNA polymerase, the BclI restriction enzyme, biotin labelled antibodies as described above, and a hydrogel bead carrying a pool of partially double-stranded DNA molecules, all of them sharing the same DNA barcode; this DNA barcode is different on every hydrogel bead. The single-stranded part of the hydrogel bead-bound DNA molecules consists of a DNA linker sequence, followed by a sequence that is antisense to the 3' end of the DNA tag or the targeted mRNA sequence, JAK2. Drops are produced with a Poisson distribution for cell encapsulation, and cell concentration is chosen such that the mean number of cells per droplet <1, ensuring that the majority of the drops contain no more than one cell. The deformable hydrogel beads are injected as a closed packed array (Abate, A. R. et al. (2009)), ensuring that most drops contain a single bead (FIG. 29, 30).

Figure 30:
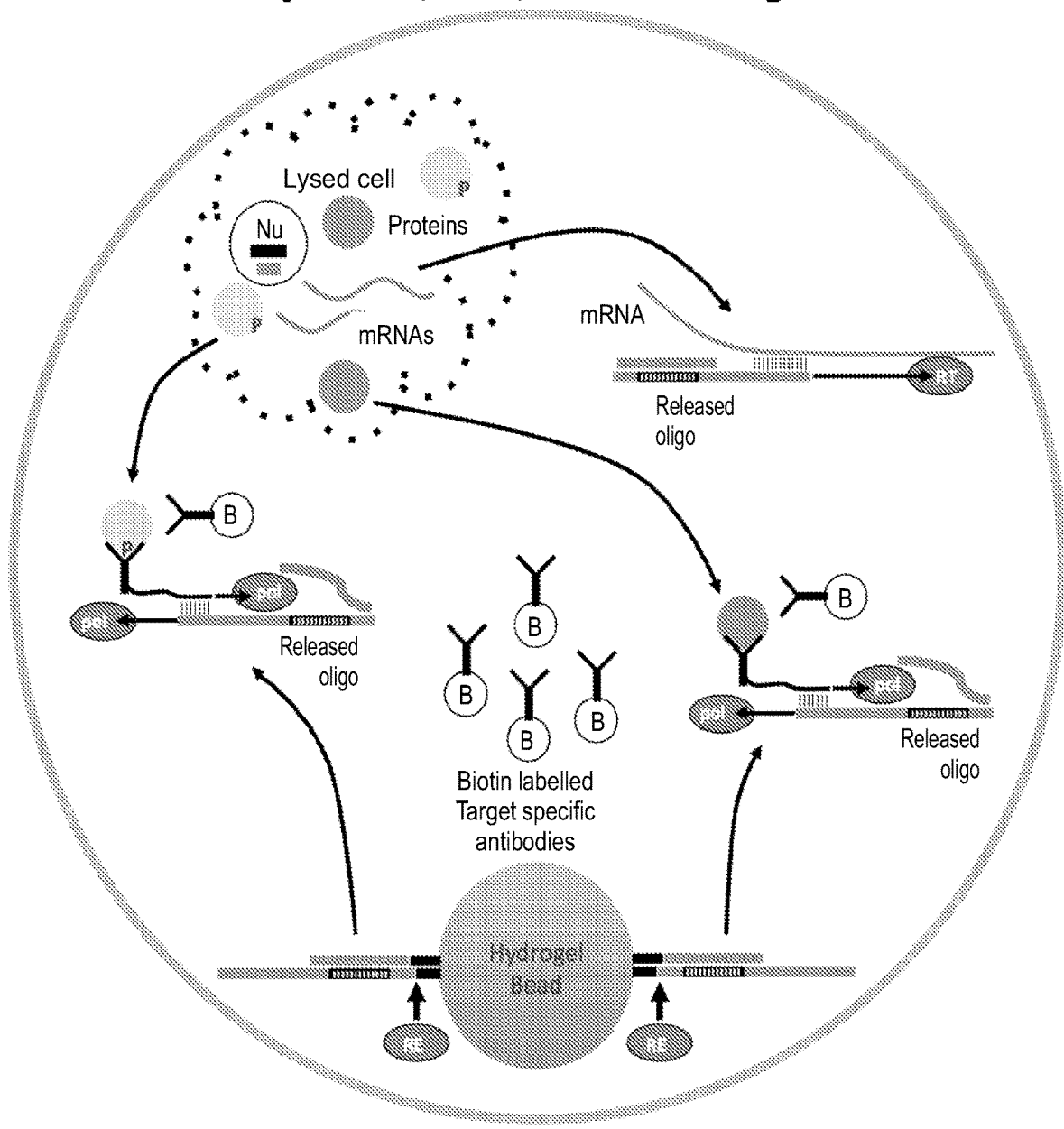
FIG. 30 is a schematic showing protein capture, RT, and DNA polymerization in droplets.

The emulsion is then placed at 55° C. for 1 h 30. During this incubation, The BclI restriction enzyme cleaves and releases the barcoded oligonucleotides into the whole volume of the drop. At the same time, the cell lyses and the released target proteins are captured by the labelled antibodies, which anneal to their complementary sequence on the single-stranded part of the hydrogel-bound barcoded DNA, and the polymerase extends the barcoded DNA molecule, copying the DNA tag. These antibody-target complexes are captured by the biotin labelled antibodies. Meanwhile, the released mRNA anneals to the complementary sequences on the single-stranded part of the corresponding released barcoded oligonucleotides, and the RT enzyme extends the barcoded DNA, copying the sequence of the targeted mRNA. The addition of the DNA barcode to the antibody bound DNA tags gives single cell specificity to these sequences (FIG. 30).

Figure 31:
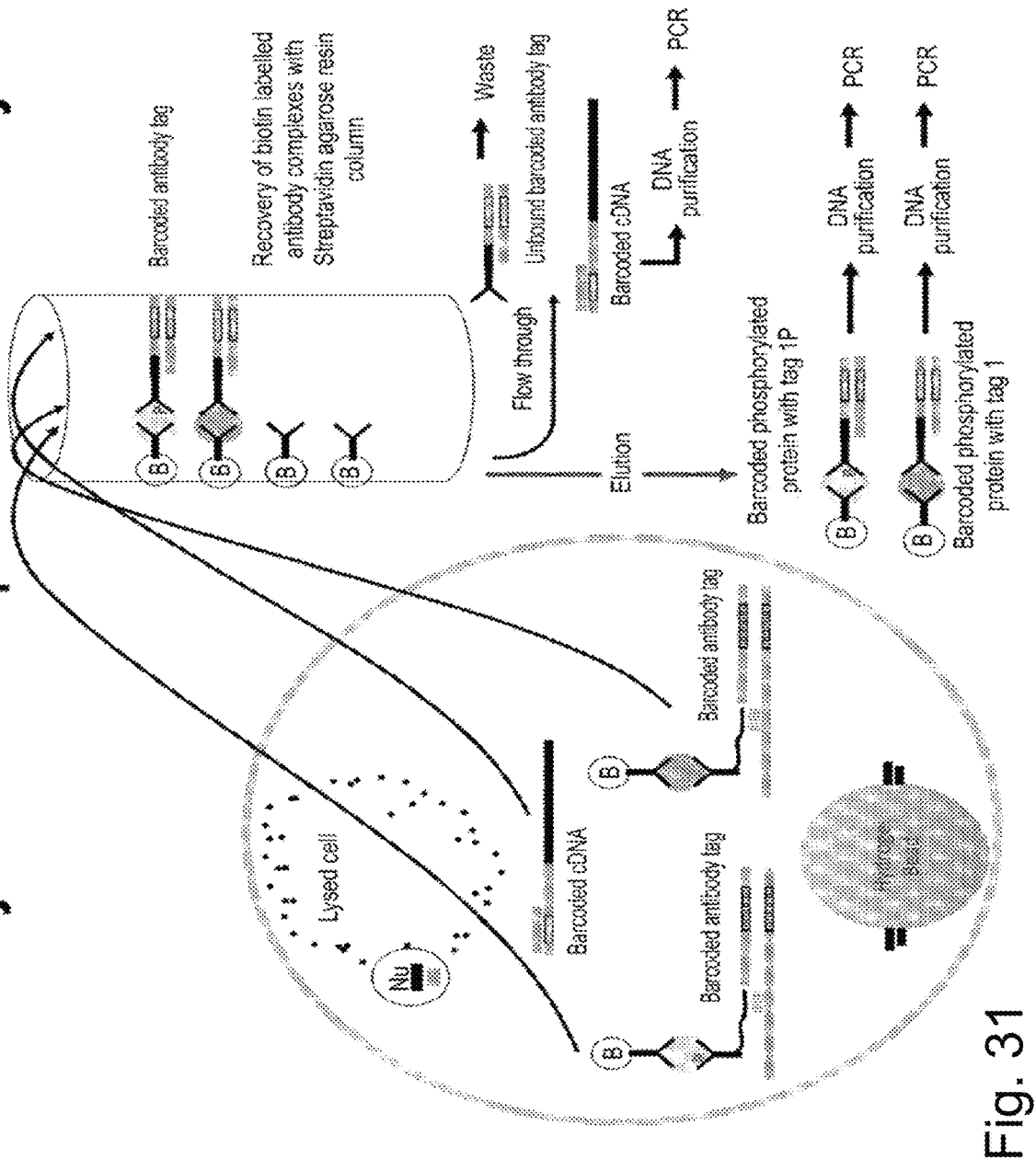
FIG. 31 is a schematic showing antibody-protein complex and cDNA recovery.

Recovery, and Separation of Phosphorylated from Non-Phosphorylated Target Proteins:

The emulsion is placed at 70° C. to inactivate the polymerase enzyme, then the emulsion is broken and the aqueous phase is recovered. Phosphorylated and non-phosphorylated proteins, together with attached antibodies, DNA tags, and barcodes, are then separated via streptavidin agarose columns (Pierce® Streptavidin Agarose Columns) from unbound DNA tag labelled antibodies and barcoded cDNA from the RT (FIG. 31). Alternatively, the complexes can be purified by size exclusion chromatography.

Amplification in Bulk and Sequencing:

The barcoded DNA tags from targeted proteins are purified using commercial kits (Agencourt AMPure XP). The cDNA from the RT DNA is purified using commercial kits (Agencourt RNAClean XP). Barcoded tags are then amplified in separated PCR for tags from phosphorylated and non-phosphorylated proteins, as is the cDNA from RT. The primers used match the end of the DNA tags, and have 5' extensions containing the sequences necessary for Illumina® sequencing i.e. the anchoring sequences P7 (SEQ ID NO: 11) and P5 (SEQ ID NO: 12).

Single cell level target protein phosphorylation data is to be quantified, and compared with total target protein quantities, via the number of target specific DNA tag reads for each DNA barcode or the number of UMIs. Single cell level mRNA expression and sequence information is also available from the sequencing.

Example 7

Antibody Repertoire Sequencing at Single-Cell Level

This example describes the method for sequencing the two mRNA that code the two peptides that compose an antibody and give its specificity. In this example, a mixture of antibody producing cell lines (hybridomas) are encapsulated in ~100 pl droplets that include a mix of culture media, cell-lysis and reverse-transcription reagents, and a hydrogel bead carrying a mix of barcoded-primers complementary to the mRNAs of the heavy and light chain antibody gene using a microfluidic device. After incubation at 55° C. (which enables enzymatic digestion by BclI, RT of the mRNA, and DNA polymerization) the emulsion is chemically broken and the aqueous phase is recovered. cDNA are purified using Solid Phase Reversible Immobilisation (SPRI) beads and amplified by PCR before being sent to sequencing.

Hydrogel Bead Production and Functionalization for Reverse Transcription:

Hydrogel beads are prepared from PEG-DA oligomers in a microfluidic chip, where an aqueous PEG-DA solution is dispersed to form droplets in a fluorinated oil continuous phase by hydrodynamic flow focusing (Anna, S., Bontoux, N., & Stone, H. (2003). Formation of dispersions using "flow focusing" in microchannels. *Applied Physics Letters*, 82(3), 364-366. doi:10.1063/1.1537519). The beads are then crosslinked via a UV activated photoinitiator. 400 µM of a double-stranded DNA oligonucleotide (duplex) called RanA, carrying a 5' acrydite modification on one end and a 4-nt 5' overhang on the other side (top strand: 5'Acrydite-TCTTCACGGAACGA (SEQ ID NO: 4); bottom strand: 5'Phosphate-CAGTTCGTTCCGTGAAGA (SEQ ID NO: 5)) is added and covalently crosslinked with the hydrogel matrix via acrylate end groups of the PEG-DA oligomers. After polymerization and washing in Tris-HCl pH 7.4 20 mM; NaCl 50 mM; Tween 0.01%; EDTA 1 mM, a first duplex with a 4-nt 5' overhang compatible with the overhang of the acrydite duplex on one side and another 4-nt 5' overhang compatible with downstream ligation on the other side is ligated using T7 DNA ligase. In its double-stranded part, this first duplex, called RanB, has for sequence the BclI restriction site (TGATCA (SEQ ID NO: 13), followed by a shorter version of Illumina® Read2 sequence (GTGTGCTCTTCCGATCT (SEQ ID NO: 14)).

After ligation and washing, the barcode is synthesized by four consecutive ligations, mediated by T7 DNA ligase, of 20-nt DNA duplexes with a 4-nt overhang at both 5' ends. The use of different 4-nt overhangs in each ligation step ensures that the 4 indices can only assemble in the correct order. In order to create a wide diversity of barcodes, the hydrogel bead batch is equally distributed in the wells of a 96 well plate. Each well contains duplex with a unique 20-nt sequence (an index) that is designed to remain unambiguous with up to three errors, plus ligation buffer and enzyme. After the ligation incubation, reaction volumes of the whole plate are pooled in one tube and washed. The next ligation steps are performed in the same way: the pooled batch is equally distributed in a new plate containing another set of 96 different duplexes together with ligation buffer and enzyme. The combinatory diversity of this split-pool synthesis is 96$^4$ (over 84 million). Finally, the last duplex ligated to the newly synthesized barcode is partially double-stranded, to allow ligation by the T7 DNA ligase, and terminated by a long single-strand 3' end (see e.g. FIGS. 9 and 10). The double-stranded region is a defined linker sequence (TACGCTACGGAACGA (SEQ ID NO: 15). The single-stranded region consists of a randomized 5-nt sequence (NNNNN (SEQ ID NO: 16), followed by the complementary sequence of the targeted genes. In this example, we used two slightly degenerated sequences: HyLRT1 (TTGATTTCCAGCTTGGTCCC (SEQ ID NO: 17)) to target light-chain mRNA from every hybridoma cell and HyHRT1 (GGCCAGTGGATAGACYGATG (SEQ ID NO: 18)) to target heavy-chain mRNA from every hybridoma cell. Note that any published cocktail of primers design to target the largest diversity of light-chain and heavy-chain mRNAs can be used. The 5-nt random sequences serve as unique molecular identifiers (UMIs): they allow sequences originating from different RT priming events to be distinguished (with different UMIs) from sequences originating from PCR amplification of the same cDNA (with the same UMIs) (Shiroguchi, K., Jia, T. Z., Sims, P. A., & Xie, X. S. (2012). Digital RNA sequencing minimizes sequence-dependent bias and amplification noise with optimized single-molecule barcodes. *Proceedings of the National Academy of Sciences*, 109(4), 1347-1352. doi: 10.1073/pnas.1118018109).

The release of the oligo, here by restriction enzyme cleavage, can be performed by replacing this sequence with any cleavable chemical group that can be attach to nucleic acids, such as photocleavable or pH-sensitive moieties.

Coding Phenotype into DNA in Drops:

Using a microfluidic chip, 50 000 cells are encapsulated in droplets, following a Poisson distribution with a lambda=0.04 (0,008% of double, or more, encapsulation event). The cell population consists of a 1:1:1 mixture of hybridoma cell lines of known sequence.

The triple flow design of the chip brings together the cells with RT enzyme, the BclI restriction enzyme and a hydrogel bead carrying a pool of partially double-stranded DNA molecules (FIG. 1) at the nozzle where it is dispersed in 100 pl drops. The single-stranded part of the hydrogel bead-bound DNA consists of a UMI sequence (SEQ ID NO: 10), followed by a sequence that is antisense to the 3' end of the target mRNAs.

Figure 32:
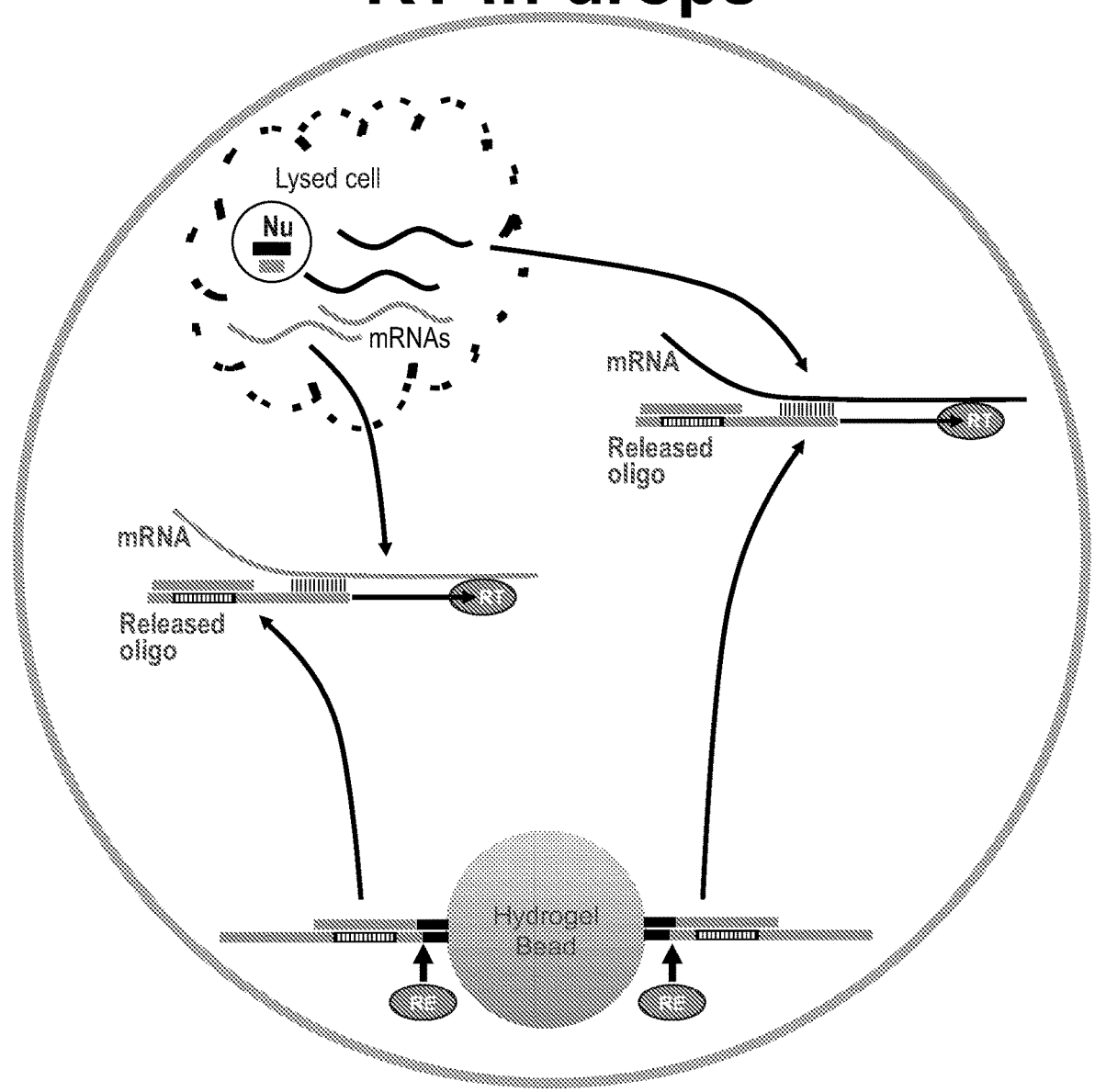
FIG. 32 is a schematic showing BclI restriction enzyme cleavage and release of the barcoded oligonucleotides into the whole volume of the drop. At the same time, the cell lyse and the released mRNA will be captured by annealing to the single-stranded part of the release barcoded DNA and the reverse transcription enzyme will extend the barcoded DNA molecule, copying the mRNA sequence. The linkage of the DNA barcode to the cDNA sequence gives single cell specificity to these cDNA sequences.

The emulsion is then placed at 55° C. for 1 h 30. During this incubation, The BclI restriction enzyme releases the barcoded oligonucleotides into the whole volume of the drop where it will meet mRNAs released from the lysed cell. These two structures anneal on their complementary sequence and the RT enzyme extends the barcoded DNA molecule, copying the mRNA sequence (FIG. 32). The DNA barcode link to the cDNA gives single cell specificity to these sequences.

Purification and Amplification in Bulk and Sequencing:

The emulsion is then placed at 70° C. to inactivate the RT enzyme. After cooling down on ice, the emulsion is broken and the aqueous phase is recovered and DNA purified using Agencourt's RNAClean XP SPRI.

Figure 33:
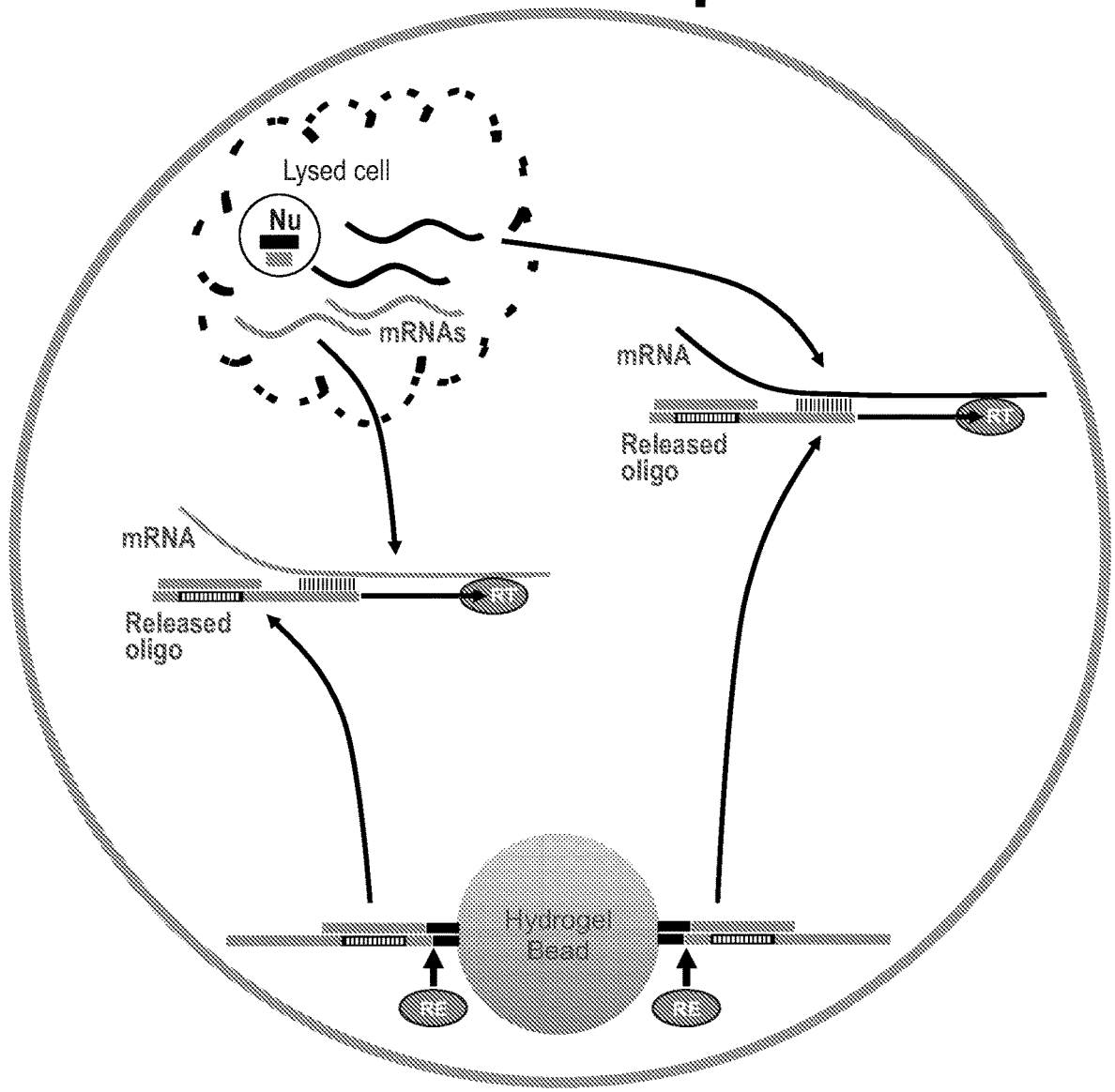
FIG. 33 is a schematic showing the result of the RT activity and the subsequent purification and amplification steps.
Figure 34:
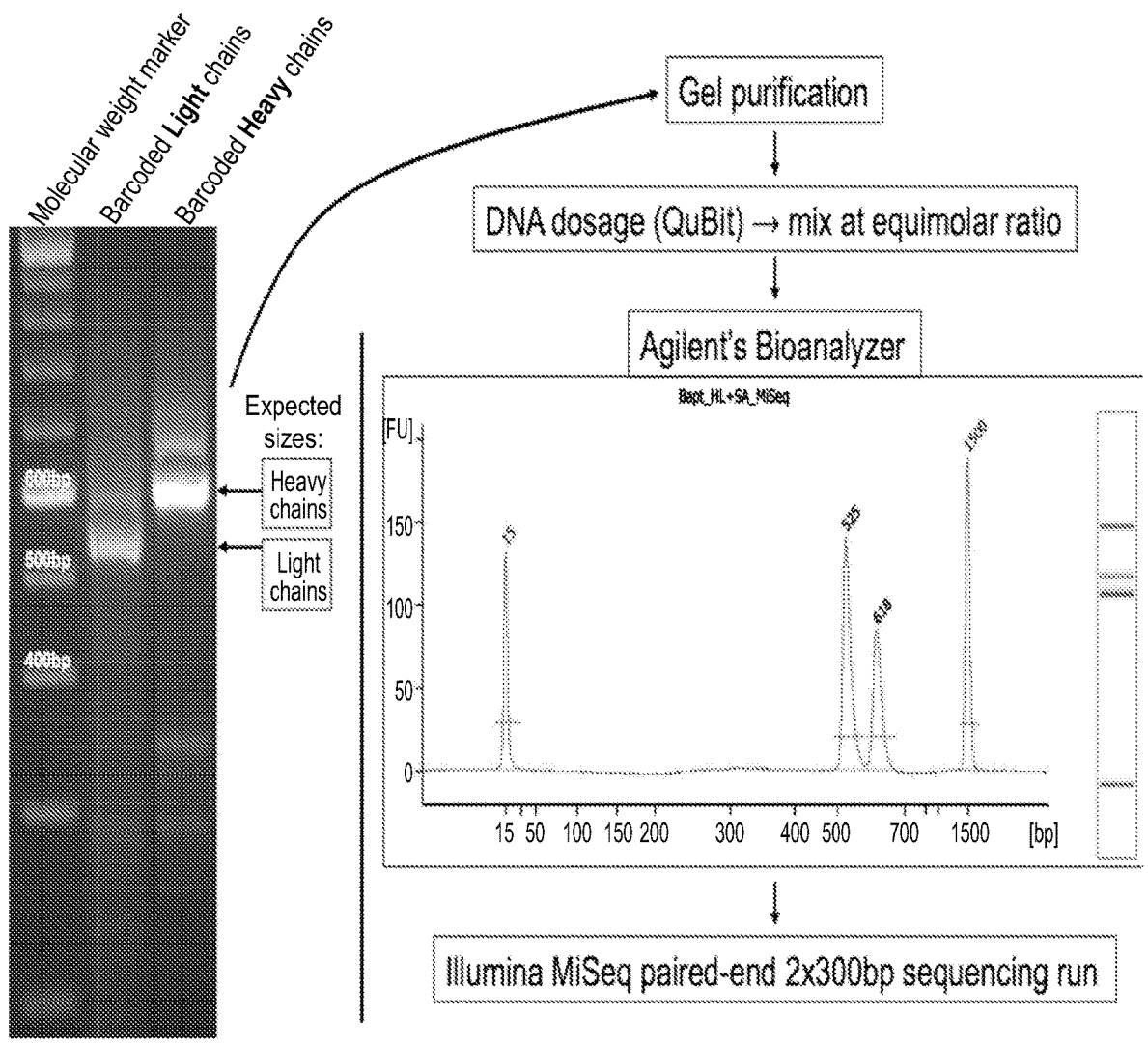
FIG. 34 shows the agarose gel with the amplified RT-in-drops product and the quality control analysis on Agilent's bioanalyzer made before sequencing.

Barcoded cDNA are then amplified by PCR: A first 15-cycle PCR is performed on 40% of the cDNA preparation using primers matching the 2 ends of the cDNA and carrying 5' extensions that introduce Illumina's read1 and completes read2 sequences. The PCR is purified using Agencourt's AMPure XP SPRI and the whole product is put in for another 10-cycle PCR with primers P7-read2 (CAAGCAGAAGACGGCATACGAGATGTGACTG-GAGTTCAGACGTGTGCTC TTCCGATCT (SEQ ID NO: 19)) and P5-read1 (AATGATACGGCGAC-CACCGAGATCTACACTCTTTCCCTACACGACGCTCT TCCGATCT (SEQ ID NO: 20) (FIG. 33). The result is once again purified with Agencourt's AMPure XP SPRI and eluted in a small volume (10 to 20 µl) and deposited on 1.5% agarose gel. The bands with the expected size (about 420 bp for the light chain cDNA and about 500 bp of the heavy chains) are purified from the gel, and mix in an equimolar ratio. This final DNA preparation is check for size purity on an Agilent Bioanalyzer and to in an Illumina's MiSeq machine (FIG. 34).

Next Generation Sequencing (NGS) and Bioinformatics Analysis of the Data:

The run operated on the sample is a paired-end 2×300 bp: each molecule processed is sequenced from both extremities and is read for 300 nucleotides inwards. Given the size of our product, there is a 50- to 100-nucleotide overlap between reads for the two extremities.

A custom-made program analyzes the data by clustering similar barcodes together, extracts the cDNA sequences associated, and computes the nature and the frequency of the associated sequences (FIG. 35). With a stringent threshold of 40 reads for each chain, 5102 pairs were obtained with 96.4% of them being correct (i.e. the heavy and the light chain corresponds to one of the three possible association present in our three cell lines).

Example 8

Simultaneous Single-Cell Phenotype and Transcriptional Levels Recovery

CytoSeq & RNAseq on B-Cells and T-Cells

The following example demonstrates the recovery of transcriptional and phenotype information, at the single-cell level, with the methods set forth herein.

In this example, cells are labeled using antibodies tagged with short RNA (or DNA) tags (Ab-tags). The Ab-tags on each antibody will carry a unique sequence to indicate the antigen-specificity of the antibody. After washing, labeled cells will be compartmentalized in droplets in a microfluidic system together with hydrogel beads carrying barcoded primers, cell lysis reagent, reverse transcriptase (RT) and dNTPs. Most droplets will contain no more than one cell, and most droplets containing single cells will also contain a single hydrogel bead, carrying primers with a unique barcode. The barcoded primers will be released from the beads using a restriction enzyme (RE) and used to prime cDNA synthesis using the Ab-tags as template. The emulsion will then be broken, the contents of the droplets pooled and the cDNAs purified to remove unincorporated primers. The barcoded cDNA will then be amplified by PCR to append Illumina sequencing primer sites and sequenced using a NextSeq or HiSeq 150 nt run to quantify the Ab-tags associated with each cell.

The tags can be RNA, DNA or a hybrid alternation of RNA and DNA nucleotides; all of those structures can be used as template by RT enzymes. Whether the template used is RNA, DNA, or a hybrid, the elongated primers resulting of the RT enzyme activity is consistently called cDNA throughout the whole document. Note that for this example, any DNA polymerase could be used in place of the RT enzyme.

Here is described the simultaneous recovery of phenotypic information (CytoSeq) and RNAseq method used to analyze, at the single-cell level, the transcription levels of 40 genes and the surface makers of a 50:50 mixture of B lymphocytes, taken from the human Ramos cell line (ATCC CRL-1596), and T lymphocytes, taken from the human Jurkatt cell line (ATCC TIB-152). Four cell-marker antibodies (CD1A, CD3D, CD72 and CD79B) will each be coupled to fluorescent antibody-specific oligonucleotides. T cells are labels much preferentially by CD1A and CD3D and B cells by CD52 and CD79B. In this test each barcode should associate entirely with either T cells profiles (i.e the combination of specific nucleotide sequence of each antibody type) or B cells profiles; only two-cell events would lead to the appearance of barcodes with mixed profiles.

Antibody-Oligonucleotide Conjugation:

Using dedicated kits (e.g. Innova Bioscience Thunder-Link® oligo conjugation system) antibodies can be covalently link to DNA or RNA oligo nucleotide. In brief, the linking chemistry is based on one hand of the modification of the antibody lysine residues, and on the other hand of the activation of an amine moiety placed on the oligo. Modified antibody and activated oligo can react with each other to form a covalent bond (conjugation).

Figure 36:
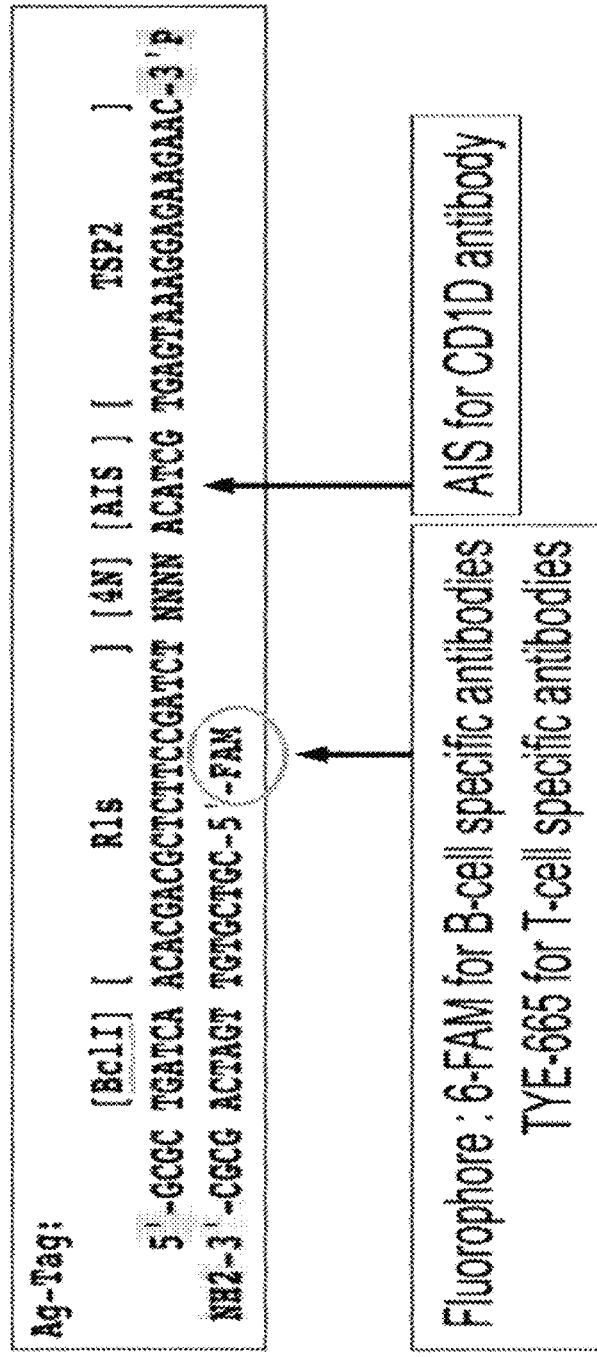
FIG. 36 is a schematic showing the sequence and the structure of the antibody tag (Ab-tag) before conjugation. (SEQ ID NO: 58-59)

A double-stranded RNA oligonucleotide (duplex) with a few modifications selected especially for CytoSeq has been design (FIG. 36): The top strand sequence contains by the BclI restriction site followed by a short version of Illumina® Read1 sequence (ACACGACGCTCTTCCGATCT (SEQ ID NO: 21)), followed by a 4 nt UMI, followed by a 6-nt sequence that will be different for every antibody (Antibody Identifying Sequence (AIS)), followed by 18-nt sequence, called TSP2, common to every top strand (TGAGTAAAGGAGAAGAAC (SEQ ID NO: 22)). Four different top strands were synthetized each with their own AIS: ACATCG; GATCTT; CTGAGC and TGCGAA to identify CD1A, CD3D, CD72 and CD79B antibodies, respectively. The bottom strand has for sequence the reverse complementary of the top strand on the BclI site and part of the short of Illumina® Read1 sequence. It carries a 3' amine modification necessary for conjugation with antibodies, fluorophore linked to its 5' end, and contains a BclI restriction site. Two different version of this bottom strand was order, one with fluorophore 6-FAM (excitation at 495 nm) and the other with fluorophore TYE-655 (excitation 665 nm).

Prior to conjugation, top strands aimed to be linked to B-cell specific antibodies (CD72 and CD79B) were anneal with the 6-FAM bottom strand and T-cell specific antibodies (CD1A and CD3D) were anneal with the TYE-665 bottom strand. Conjugation efficiencies are verified on SDS-PAGE and cell-labeling efficacy checked on a cytometer.

Cell Labeling:

Prior to encapsulation in drops a mixture of B and T lymphocytes is labeled with the 4 tagged-antibodies cocktail following standard labeling protocols: $10^6$-$10^7$ cells are washed in staining buffer (PBS, 0.5% bovine serum albumin (BSA), 2 mM EDTA), incubated in 100 µl for 10 minutes in the dark and at 4° C. with 4 µg of tagged-antibodies and finally washed twice with 1 ml of staining buffer.

Hydrogel bead production and functionalization for reverse transcription:

Hydrogel beads are prepared from PEG-DA oligomers in a microfluidic chip, where an aqueous PEG-DA solution is dispersed to form droplets in a fluorinated oil continuous phase by hydrodynamic flow focusing (Anna, S., Bontoux, N., & Stone, H. (2003). Formation of dispersions using "flow focusing" in microchannels. *Applied Physics Letters*, 82(3), 364-366. doi:10.1063/1.1537519). The beads are then crosslinked via a UV activated photoinitiator. 400 µM of a double-stranded DNA oligonucleotide (duplex) called RanA, carrying a 5' acrydite modification on one end and a 4-nt 5' overhang on the other side (top strand: 5'Acrydite-TCTTCACGGAACGA (SEQ ID NO: 4); bottom strand: 5'Phosphate-CAGTTCGTTCCGTGAAGA (SEQ ID NO: 5)) is added and covalently crosslinked with the hydrogel matrix via acrylate end groups of the PEG-DA oligomers. After polymerization and washing in Tris-HCl pH 7.4 20 mM; NaCl 50 mM; Tween 0.01%; EDTA 1 mM, a first duplex with a 4-nt 5' overhang compatible with the overhang of the acrydite duplex on one side and another 4-nt 5' overhang compatible with downstream ligation on the other side is ligated using T7 DNA ligase. In its double-stranded part, this first duplex, called RanB, has for sequence the BclI restriction site (TGATCA (SEQ ID NO: 7), followed by a shorter version of Illumina® Read2 sequence (GTGTGCTCTTCCGATCT (SEQ ID NO: 23)).

After ligation and washing, the barcode is synthesized by four consecutive ligations, mediated by T7 DNA ligase, of 20-nt DNA duplexes with a 4-nt overhang at both 5' ends. The use of different 4-nt overhangs in each ligation step ensures that the 4 indices can only assemble in the correct order. In order to create a wide diversity of barcodes, the hydrogel bead batch is equally distributed in the wells of a 96 well plate. Each well contains duplex with a unique 20-nt sequence (an index) that is designed to remain unambiguous with up to three errors, plus ligation buffer and enzyme. After the ligation incubation, reaction volumes of the whole plate are pooled in one tube and washed. The next ligation steps are performed in the same way: the pooled batch is equally distributed in a new plate containing another set of 96 different duplexes together with ligation buffer and enzyme. The combinatory diversity of this split-pool synthesis is $96^4$ (over 84 million). Finally, the last duplex ligated to the newly synthesized barcode is partially double-stranded, to allow ligation by the T7 DNA ligase, and terminated by a long single-strand 3' end (see e.g. FIGS. 9 and 10). The double-stranded region is a defined linker sequence (TACGCTACGGAACGA (SEQ ID NO: 9). The single-stranded region consists of a randomized 5-nt sequence (SEQ ID NO: 24), followed by the antisense sequence of ASP2 (GTTCTTCTCCTTTACTCA (SEQ ID NO: 25)) to prime RT (with Ab-tags as templates). The 5-nt random sequences serve as unique molecular identifiers (UMIs): they allow sequences originating from different RT priming event to be distinguished (with different UMIs) from sequences originating from PCR amplification of the same cDNA (with the same UMIs) (Shiroguchi, K., Jia, T. Z., Sims, P. A., & Xie, X. S. (2012). Digital RNA sequencing minimizes sequence-dependent bias and amplification noise with optimized single-molecule barcodes. *Proceedings of the National Academy of Sciences*, 109(4), 1347-1352. doi: 10.1073/pnas.1118018109).

The release of the oligo, here by restriction enzyme cleavage, can be performed by replacing this sequence with any cleavable chemical group that can be attach to nucleic acids, such as photocleavable or pH-sensitive moieties.

Coding Phenotype into DNA in Drops:

Using a microfluidic chip, labeled cells are encapsulated in droplets together with RT enzyme, the MI restriction enzyme and a hydrogel bead carrying a pool of partially double-stranded DNA molecules (FIG. 18). The single-stranded part of the hydrogel bead-bound DNA consists of a UMI sequence (SEQ ID NO: 10), followed by a sequence that is antisense to the 3' end of the Ab-tag.

The emulsion is then placed at 55° C. for 1 h 30. During this incubation, The BclI restriction enzyme is cleaved and releases the barcoded oligonucleotides and the Ab-tags into the whole volume of the drop. These two structures anneal on their complementary sequence (TSP2 sense and antisense) and the RT enzyme extends the barcoded DNA molecule, copying the Ab-tags (FIG. 19). The DNA barcode link to the Ab-tags gives single cell specificity to these sequences.

Purification and Amplification in Bulk and Sequencing:

The emulsion is then placed at 70° C. to inactivate the RT enzyme. After cooling down on ice, the emulsion is broken and the aqueous phase is recovered and DNA purified using commercial kits (Agencourt RNAClean XP).

Figure 37:
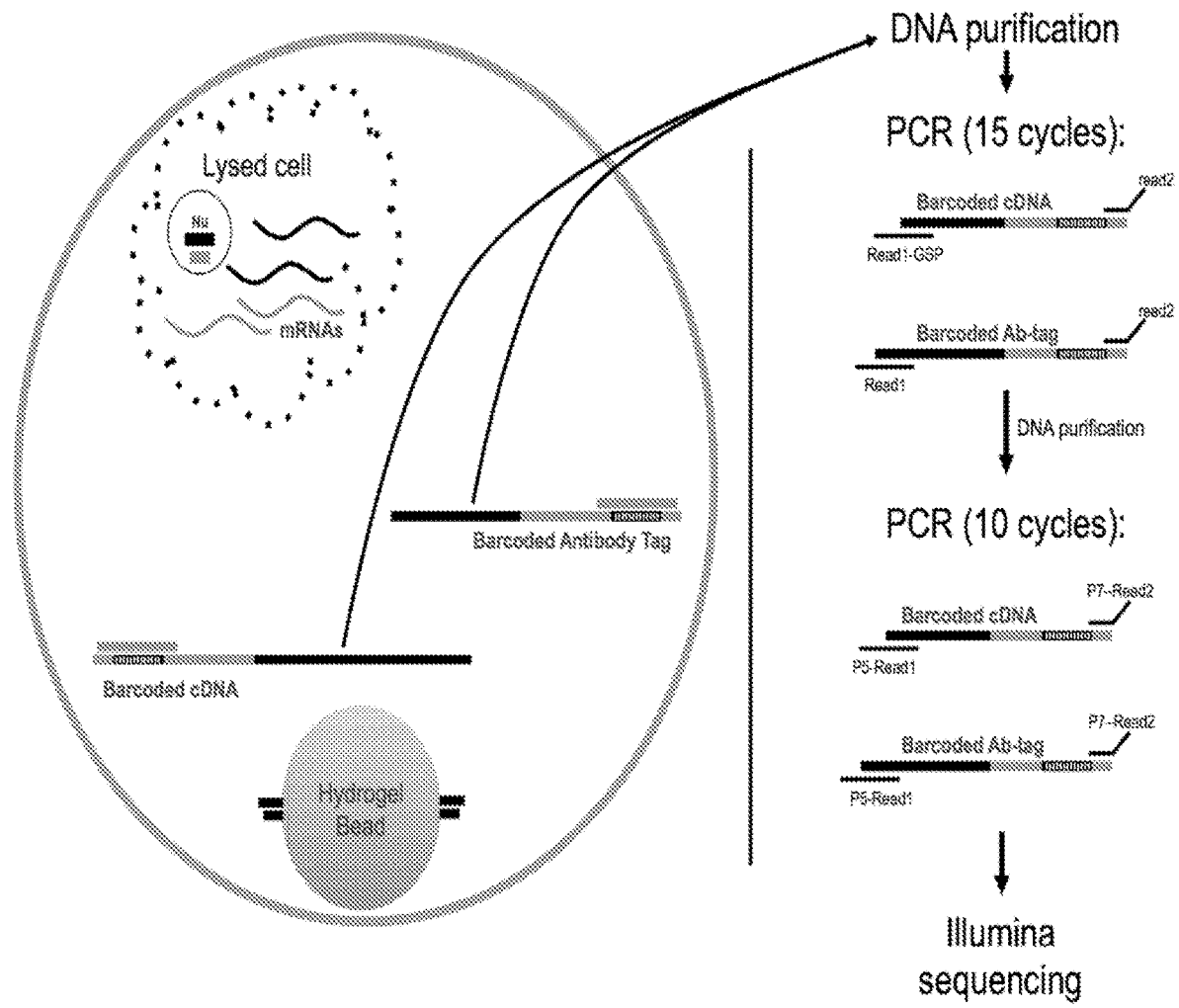
FIG. 37 is a schematic showing the result of the RT activity and the subsequent purification and amplification steps.

Barcoded tags are then amplified by PCR. The primers used match the end of the tags and have 5' extensions containing the sequences necessary for Illumina® sequencing i.e. anchoring sequences P7 (SEQ ID NO: 11) and P5 (SEQ ID NO: 12) (FIG. 37).

Figure 39:
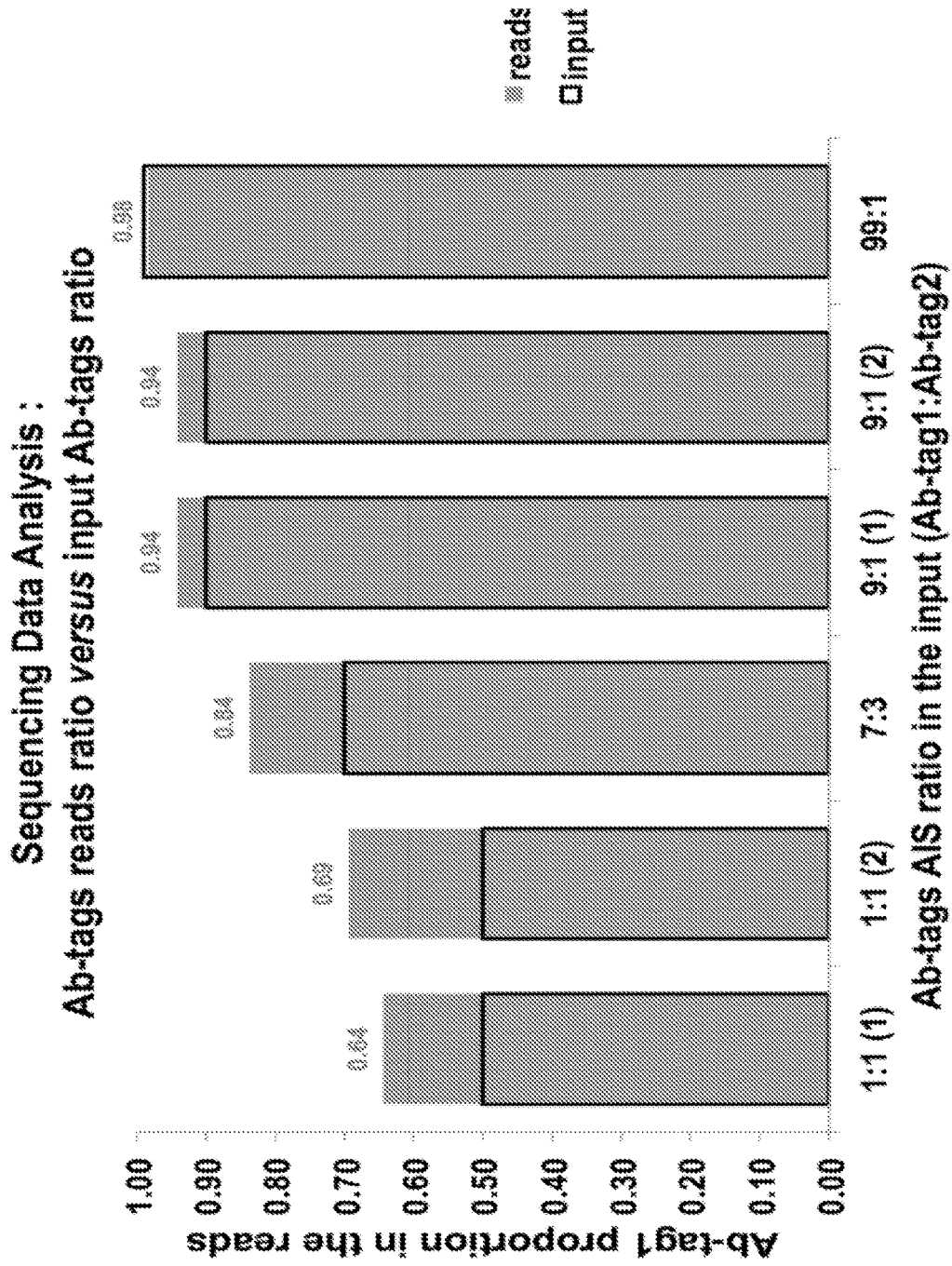
FIG. 39 is a graph showing the results for the analysis of the sequencing data. Expected proportion of Ab-tag1 (those in the input) is shown with empty black outlined bars. Grey bars show the proportion of Ab-tag1 in the reads.

Sensibility of the Method:

This method has been carried out using free soluble Ab-tags instead of labeled cells. The concentration of Ab-tags in the drop was 100 pM, which corresponds to about 6000 Ab-tag molecules in each drop. The Ab-tags solutions brought into the drops were mixtures of two different Ab-tag (Ab-tag1 and Ab-tag2 with different AIS) at various ratios (1:1 (twice); 7:3; 9:1 (twice) or 99:1). Amplified PCR product were purified on 2% agarose gels, checked for size purity on an Agilent Bioanalyzer (FIG. 38), and put in an Illumina's NextSeq machine. The run operated on the sample is a single-read 150 bp, which covers the whole barcode and the AIS. The results showed good correlation between the Ab-tag ratio in the input (before encapsulation) and in the NGS data (distribution of reads) (FIG. 39). Notably, we are able to detect both Ab-tags species in the data coming from the 99:1 ratio. This corresponds to a sensitivity of to less than 70 molecules.

All publications, patents, and patent applications mentioned herein are incorporated by reference to the same extent as if each individual publication, patent or patent application was specifically and individually indicated to be incorporated by reference in its entirety. In the event of there being a difference between definitions set forth in this application and those in documents incorporated herein by reference, the definitions set forth herein control. Various modifications and variations of the described methods, pharmaceutical compositions, and kits of the disclosure will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

We claim:

1. A method of identifying whether a target mRNA and a target polypeptide in individual compartments are from the same compartment, comprising:

generating subsamples by segregating a sample, or a portion thereof, into individual compartments, the sample comprising a cell, a population of cells, or an acellular system, wherein each of the individual compartments further comprise:

a first oligonucleotide comprising an origin specific barcode sequence, a unique molecular identifier sequence unique to a target mRNA from the subsamples, and a sequence for binding the target mRNA;

a second oligonucleotide comprising an origin specific barcode sequence and a unique molecular identifier sequence unique to a target polypeptide from the subsamples, and a molecule for capturing the target polypeptide; and wherein the origin specific barcode sequence of the first oligonucleotide and the origin specific barcode sequence of the second oligonucleotide are the same in each of the individual compartments but differ among the individual compartments;

labeling the target mRNA and the target polypeptide in each of the individual compartments by binding of the first oligonucleotide to the target mRNA and binding of the second oligonucleotide to the target polypeptide, wherein the target mRNA and the target polypeptide in each of the individual compartments are from the acellular system of the subsample or a lysed cell or lysed population of cells of the subsamples within the individual compartments prior to the labeling step;

generating a cDNA product in each of the individual compartments from all or a portion of the labeled target mRNA by introducing reagents for generating the cDNA product into each of the individual compartments such that the origin specific barcode sequence of the first oligonucleotide and the unique molecular identifier sequence unique to the target mRNA is incorporated into the cDNA product;

producing pooled cDNAs by pooling the cDNA product from each of the individual compartments and generating different amplicons comprising the origin specific barcode sequence of the first oligonucleotide and the unique molecular identifier sequence unique to the target mRNA by amplifying the pooled cDNAs, wherein the origin specific barcode sequence of the first oligonucleotide in each of the different amplicons is different;

isolating the labeled target polypeptide labeled in the labeling step from each of the individual compartments and obtaining different cleaved products comprising the origin specific barcode sequence of the second oligonucleotide and the unique molecular identifier sequence unique to the target polypeptide by cleaving the labeled target polypeptide from each of the individual compartments; and identifying whether a target mRNA and a target polypeptide in the individual compartments are from the same compartment by sequencing of the origin specific barcode sequence of the first oligonucleotide and unique molecular identifier sequence unique to the target mRNA in each of different amplified products and sequencing the origin specific barcode of the second oligonucleotide and unique molecular identifier sequence unique to the target polypeptide in each of the different cleaved products, wherein the origin specific barcode sequence of the first oligonucleotide associated with the target mRNA and the origin specific barcode sequence of the second oligonucleotide associated with target polypeptide are identical indicates that the target mRNA and the target polypeptide in the individual compartments are from the same compartment.

2. The method of claim 1, wherein each of the individual compartments comprises a single cell from the sample.

3. The method of claim 1, wherein the target polypeptide is expressed on the surface of the cell or the population of cells.

4. The method of claim 1, wherein the first oligonucleotide and the second oligonucleotide further comprise one or more primer sequences, a sequencing adaptor, one or more restriction sites, or a capture moiety.

5. The method of claim 4, wherein the primer sequences are universal primer sequences, and/or wherein the origin specific barcode sequence of the first oligonucleotide or the second oligonucleotide comprises RNA, DNA, or a combination of RNA and DNA.

6. The method of claim 1, wherein the first oligonucleotide and the second oligonucleotide are reversibly or irreversibly attached to a solid substrate in each of the individual compartments.

7. The method of claim 6, wherein each of the first oligonucleotide and the second oligonucleotide is attached to the solid substrate by an adapter binding sequence located on each of the first oligonucleotide and second oligonucleotide that binds to an adapter nucleotide sequence on the solid substrate.

8. The method of claim 6, wherein the solid substrate is a hydrogel bead.

9. The method of claim 6, wherein the first oligonucleotide and the second oligonucleotide are released from the solid substrate prior to the labeling step.

10. The method of claim 9, wherein the first oligonucleotide and the second oligonucleotide are released from the solid substrate by breaking down of the solid substrate, or by chemical cleavage, photocleavage, or enzymatic cleavage of the first oligonucleotide and the second oligonucleotide.

11. The method of claim 1, wherein the molecule for capturing the target polypeptide comprises a small molecule, an antigen, an antibody, a protein binding domain, a nucleic acid, or a polysaccharide.

12. The method of claim 11, wherein the target polypeptide is a target polypeptide having a post-translational modification and the molecule for capturing the target polypeptide is an antibody specifically binding to the target polypeptide having the post-translational modification.

13. The method of claim 1, wherein the molecule for capturing the target polypeptide is an antibody specifically binding to the target polypeptide.

14. The method of claim 1, wherein the target polypeptides is located on a surface of the cell or one or more cells of the cell population, and the molecule for capturing the target polypeptide is a binding partner of the target polypeptide, or wherein the target polypeptide is an antibody expressed by the cell or one or more cells of the population of cells and the molecule for capturing the target polypeptide is an antigen of the antibody, or wherein the target polypeptide is a cell surface receptor and the target mRNA is a mRNA encoding the cell surface receptor.

15. The method of claim 1, wherein the target mRNA encodes an antibody light chain, an antibody heavy chain, or a complementarity determining region (CDR).

16. The method of claim 15, wherein the cell is a B cell, a T cell, a plasmablast or a plasma cell.

17. The method of claim 1, wherein the molecule for capturing the target polypeptide is not attached directly to the second oligonucleotide and comprises an oligonucleotide tag, and wherein the second oligonucleotide further comprises a sequence capable of hybridizing to the oligonucleotide tag.

18. The method of claim 17, wherein the molecule for capturing the target polypeptide is bound to a first member of a binding pair and the oligonucleotide tag is bound to a second member of the binding pair.

19. The method of claim 18, wherein the binding pair is streptavidin-biotin pair.

20. The method of claim 17, wherein the molecule for capturing the target polypeptide and the oligonucleotide tag are biotinylated and bound to a linking streptavidin substrate.

21. The method of claim 20, wherein multiple copies of the oligonucleotide tag are bound to the molecule for capturing the target polypeptide via the linking streptavidin substrate.

22. The method of claim 1, wherein each of the individual compartments comprises a single droplet generated on a microfluidic device.

23. The method of claim 22, wherein the single droplet is formed by merging a first droplet comprising the cell, the population of cells, or the acellular system with a second droplet comprising the first oligonucleotide and the second oligonucleotide.

24. The method of claim 22, wherein the first oligonucleotide and the second oligonucleotide in the second droplet are bound to a single solid substrate.

25. The method of claim 22, further comprising merging the single droplet with a third droplet comprising additional reagents.

26. The method of claim 25, wherein the additional reagents comprises cell lysis reagents or one or more of reverse transcription reagents, restriction enzymes, dNTPS, and DNA polymerases.

27. The method of claim 22, further comprising injecting additional reagents into the single droplet.

28. The method of claim 27, wherein the additional reagents are cell lysis reagents or one or more of reverse transcription reagents, restriction enzymes, dNTPS, and DNA polymerases.

29. The method of claim 1, further comprising introducing a target polypeptide capture molecule into each of the individual compartments, the target polypeptide capture molecule and the molecule for capturing the target polypeptide having the same binding affinity for the target polypeptide, wherein the target polypeptide capture molecule comprises a capture moiety and binds the target polypeptide such that a sandwich complex comprising the target polypeptide capture molecule, the target polypeptide, and the molecule for capturing the target polypeptide is formed, and wherein the sandwich complex is purified from each of the individual compartments by the capture moiety after the labeling step.

30. The method of claim 1, wherein each of the sub-samples comprises a single cell from the sample.

* * * * *